(12) United States Patent
Alexander et al.

(10) Patent No.: US 11,813,445 B2
(45) Date of Patent: Nov. 14, 2023

(54) MECHANICAL CIRCULATORY SUPPORT DEVICE WITH CENTRIFUGAL IMPELLER DESIGNED FOR IMPLANTATION IN THE DESCENDING AORTA

(71) Applicant: Queen Mary University of London, London (GB)

(72) Inventors: Theodosios Alexander, Venice, FL (US); Martin T. Rothman, Santa Rosa, CA (US)

(*) Notice: Subject to any disclaimer, the term of this patent is extended or adjusted under 35 U.S.C. 154(b) by 23 days.

(21) Appl. No.: 17/109,612

(22) Filed: Dec. 2, 2020

(65) Prior Publication Data

US 2021/0154463 A1   May 27, 2021

Related U.S. Application Data

(63) Continuation of application No. 15/619,335, filed on Jun. 9, 2017, now Pat. No. 10,857,274, which is a
(Continued)

(30) Foreign Application Priority Data

Nov. 6, 2012 (GB) ..................................... 1219958

(51) Int. Cl.
*A61M 60/422* (2021.01)
*A61M 60/148* (2021.01)
(Continued)

(52) U.S. Cl.
CPC ........ *A61M 60/422* (2021.01); *A61M 60/139* (2021.01); *A61M 60/148* (2021.01);
(Continued)

(58) Field of Classification Search
CPC .. A61M 60/40; A61M 60/122; A61M 60/148; A61M 60/422; A61M 60/857;
(Continued)

(56) References Cited

U.S. PATENT DOCUMENTS 3,174,851 A   3/1965 Buehler et al.
5,267,940 A   12/1993 Moulder
(Continued)

FOREIGN PATENT DOCUMENTS

EP   3519008   8/2019
EP   3630218   4/2020
(Continued)

OTHER PUBLICATIONS

Extended European Search Report for EP 18809622.6 dated Apr. 14, 2021 in 18 pages.
(Continued)

*Primary Examiner* — Paula J Stice
(74) *Attorney, Agent, or Firm* — Knobbe, Martens, Olson & Bear, LLP

(57) ABSTRACT

Mechanical circulatory supports configured to operate in series with the native heart are disclosed. In an embodiment, a centrifugal pump is used. In an embodiment, inlet and outlet ports are connected into the aorta and blood flow is diverted through a lumen and a centrifugal pump between the inlet and outlet ports. The supports may create a pressure rise between about 40-80 mmHg, and maintain a flow rate of about 5 L/min. The support may be configured to be inserted in a collinear manner with the descending aorta. The support may be optimized to replicate naturally occurring vortex formation within the aorta. Diffusers of different dimensions and configurations, such as helical configuration, and/or the orientation of installation may be used to optimize vortex formation. The support may use an impeller which is electromagnetically suspended, stabilized, and rotated to pump blood.

17 Claims, 32 Drawing Sheets

Related U.S. Application Data continuation-in-part of application No. 14/440,848, filed as application No. PCT/GB2013/052889 on Nov. 5, 2013, now abandoned.

(60) Provisional application No. 62/513,927, filed on Jun. 1, 2017, provisional application No. 62/403,428, filed on Oct. 3, 2016.

(51) Int. Cl.

| | | |
|---|---|---|
| *A61M 60/274* | (2021.01) | |
| *A61M 60/876* | (2021.01) | |
| *A61M 60/531* | (2021.01) | |
| *A61M 60/546* | (2021.01) | |
| *A61M 60/30* | (2021.01) | |
| *A61M 60/139* | (2021.01) | |
| *A61M 60/237* | (2021.01) | |
| *A61M 60/221* | (2021.01) | |
| *A61M 60/232* | (2021.01) | |
| *A61F 2/06* | (2013.01) | |
| *A61M 60/562* | (2021.01) | |
| *A61M 60/896* | (2021.01) | |

(52) U.S. Cl.
CPC ........ *A61M 60/221* (2021.01); *A61M 60/232* (2021.01); *A61M 60/237* (2021.01); *A61M 60/274* (2021.01); *A61M 60/30* (2021.01); *A61M 60/531* (2021.01); *A61M 60/546* (2021.01); *A61M 60/876* (2021.01); *A61F 2/06* (2013.01); *A61M 60/562* (2021.01); *A61M 60/896* (2021.01)

(58) Field of Classification Search
CPC .............. A61M 60/871; A61M 60/135; A61M 60/205; A61M 60/50; A61M 60/562; A61F 2/06

See application file for complete search history.

(56) References Cited

U.S. PATENT DOCUMENTS

| | | |
|---|---|---|
| 6,171,078 B1 | 1/2001 | Schob |
| 6,575,717 B2 | 6/2003 | Ozaki et al. |
| 6,716,157 B2 | 4/2004 | Goldowsky |
| 7,240,677 B2 | 7/2007 | Fox |
| 7,841,976 B2 | 11/2010 | McBride et al. |
| 7,976,271 B2 | 7/2011 | Larose et al. |
| 8,177,703 B2 | 5/2012 | Smith et al. |
| 8,449,443 B2 | 5/2013 | Rodefeld et al. |
| 8,684,904 B2 | 4/2014 | Campbell et al. |
| 8,690,749 B1 | 4/2014 | Nunez |
| 8,727,959 B2 | 5/2014 | Reitan et al. |
| 8,992,163 B2 | 3/2015 | McBride et al. |
| 9,211,368 B2 | 12/2015 | Wampler |
| 9,308,302 B2 | 4/2016 | Zeng |
| 9,327,067 B2 | 5/2016 | Zeng et al. |
| 9,358,329 B2 | 6/2016 | Fitzgerald et al. |
| 9,364,592 B2 | 6/2016 | McBride et al. |
| 9,364,593 B2 | 6/2016 | McBride et al. |
| 9,394,612 B2 | 7/2016 | Bayer et al. |
| 9,638,202 B2 | 5/2017 | Ozaki et al. |
| 9,717,833 B2 | 8/2017 | McBride et al. |
| 9,737,651 B2 | 8/2017 | Wampler |
| 9,872,948 B2 | 1/2018 | Siess |
| 9,913,937 B2 | 3/2018 | Schwammenthal et al. |
| 9,962,258 B2 | 5/2018 | Seguin et al. |
| 10,027,114 B2 | 7/2018 | Potharaju et al. |
| 10,039,874 B2 | 8/2018 | Schwammenthal et al. |
| 10,179,197 B2 | 1/2019 | Kaiser et al. |
| 10,215,187 B2 | 2/2019 | McBride et al. |
| 10,219,901 B2 | 3/2019 | Seguin et al. |
| 10,285,686 B2 | 5/2019 | Gammie et al. |
| 10,299,918 B2 | 5/2019 | Tuval |
| 10,350,341 B2 | 7/2019 | Throckmorton et al. |
| 10,363,350 B2 | 7/2019 | Schwammenthal et al. |
| 10,478,540 B2 | 11/2019 | Scheckel et al. |
| 10,478,542 B2 | 11/2019 | Jahangir |
| 10,500,323 B2 | 12/2019 | Heuring et al. |
| 10,583,231 B2 | 3/2020 | Schwammenthal et al. |
| 10,667,821 B2 | 6/2020 | Dehdashtian et al. |
| 10,695,114 B2 | 6/2020 | Fox |
| 10,722,631 B2 | 7/2020 | Salahieh et al. |
| 10,792,413 B2 | 10/2020 | Dann et al. |
| 10,808,704 B2 | 10/2020 | Siess et al. |
| 10,842,921 B2 | 11/2020 | Siess et al. |
| 10,856,979 B2 | 12/2020 | Tuval et al. |
| 10,857,274 B2 | 12/2020 | Alexander et al. |
| 10,864,309 B2 | 12/2020 | McBride et al. |
| 10,864,310 B2 | 12/2020 | Schwammenthal et al. |
| 10,881,770 B2 | 1/2021 | Tuval et al. |
| 10,893,927 B2 | 1/2021 | Sohn |
| 10,898,320 B2 | 1/2021 | Spence et al. |
| 10,898,625 B2 | 1/2021 | Toellner et al. |
| 10,905,808 B2 | 2/2021 | Tuval et al. |
| 10,907,646 B2 | 2/2021 | Bredenbreuker et al. |
| 10,918,773 B2 | 2/2021 | Guo et al. |
| 10,918,774 B2 | 2/2021 | Stanfield et al. |
| 10,960,116 B2 | 3/2021 | Campbell et al. |
| 10,980,927 B2 | 4/2021 | Pfeffer et al. |
| 10,993,805 B2 | 5/2021 | Staubinger et al. |
| 10,993,824 B2 | 5/2021 | Longo |
| 10,994,120 B2 | 5/2021 | Tuval et al. |
| 11,020,582 B2 | 6/2021 | Cambronne et al. |
| 11,020,584 B2 | 6/2021 | Siess et al. |
| 11,033,275 B2 | 6/2021 | Franano et al. |
| 11,033,390 B2 | 6/2021 | Krivoruchko |
| 11,033,727 B2 | 6/2021 | Tuval et al. |
| 11,039,917 B2 | 6/2021 | Bruchman et al. |
| 11,045,316 B2 | 6/2021 | Zhang |
| 11,045,317 B2 | 6/2021 | Nguyen et al. |
| 11,045,338 B2 | 6/2021 | Boyle et al. |
| 11,045,638 B2 | 6/2021 | Keenan et al. |
| 11,051,833 B2 | 7/2021 | Martin et al. |
| 11,051,959 B2 | 7/2021 | Bar et al. |
| 11,058,536 B2 | 7/2021 | Huber |
| 11,058,539 B2 | 7/2021 | Dixon et al. |
| 11,058,563 B2 | 7/2021 | Van Langenhove |
| 11,058,564 B2 | 7/2021 | Carpenter et al. |
| 11,058,565 B2 | 7/2021 | Laramy et al. |
| 11,058,853 B2 | 7/2021 | Rosenberg et al. |
| 11,058,865 B2 | 7/2021 | Fitzgerald et al. |
| 11,060,382 B2 | 7/2021 | Sherman |
| 11,065,007 B2 | 7/2021 | Demeritt |
| 11,065,028 B2 | 7/2021 | Farhangnia et al. |
| 11,065,029 B2 | 7/2021 | Mcmahon et al. |
| 11,065,114 B2 | 7/2021 | Raanani et al. |
| 11,065,115 B2 | 7/2021 | Benichou et al. |
| 11,065,117 B2 | 7/2021 | Zeng |
| 11,065,138 B2 | 7/2021 | Schreck et al. |
| 11,065,140 B2 | 7/2021 | Mcweeney et al. |
| 11,065,141 B2 | 7/2021 | Wood et al. |
| 11,071,533 B2 | 7/2021 | Rothstein et al. |
| 11,072,201 B2 | 7/2021 | Nicastri et al. |
| 11,116,959 B2 | 9/2021 | Alexander et al. |
| 2002/0094281 A1 | 7/2002 | Khanvilkar et al. |
| 2003/0228214 A1 | 12/2003 | McBride |
| 2003/0233143 A1 | 12/2003 | Gharib et al. |
| 2006/0245959 A1 | 11/2006 | Larose et al. |
| 2008/0058146 A1 | 3/2008 | Pizzichil et al. |
| 2008/0300447 A1* | 12/2008 | Lu ....................... A61M 60/869 600/16 |
| 2010/0076247 A1 | 3/2010 | Zilbershlag et al. |
| 2011/0034874 A1 | 2/2011 | Reitan et al. |
| 2011/0152600 A1* | 6/2011 | Scott ..................... A61M 60/00 600/16 |
| 2011/0200451 A1 | 8/2011 | Lehmann et al. |
| 2011/0238172 A1 | 9/2011 | Akdis |
| 2011/0239693 A1 | 10/2011 | Fujisaku et al. |
| 2012/0253103 A1 | 10/2012 | Robert |
| 2012/0277520 A1 | 11/2012 | Duncan |

(56) References Cited

U.S. PATENT DOCUMENTS

| | | | |
|---|---|---|---|
| 2012/0310036 A1* | 12/2012 | Peters .................. | A61M 60/82 |
| | | | 600/16 |
| 2013/0030240 A1* | 1/2013 | Schima ................ | A61M 60/50 |
| | | | 600/16 |
| 2013/0281762 A1 | 10/2013 | Mi-Vad | |
| 2014/0051908 A1 | 2/2014 | Hridaya | |
| 2014/0275726 A1 | 9/2014 | Zeng | |
| 2015/0297813 A1 | 10/2015 | Korakianitis et al. | |
| 2016/0089482 A1 | 3/2016 | Siegenthaler | |
| 2016/0271309 A1 | 9/2016 | Throckmorten et al. | |
| 2017/0274128 A1 | 9/2017 | Tamburino et al. | |
| 2017/0340788 A1 | 11/2017 | Korakianitis et al. | |
| 2018/0169313 A1 | 6/2018 | Schwammenthal et al. | |
| 2019/0321529 A1 | 10/2019 | Korakianitis et al. | |
| 2020/0015987 A1 | 1/2020 | Einav et al. | |
| 2021/0077687 A1 | 3/2021 | Leonhardt | |
| 2021/0154463 A1 | 5/2021 | Alexander et al. | |
| 2021/0260358 A1 | 8/2021 | Alexander et al. | |
| 2022/0040470 A1 | 2/2022 | Alexander et al. | |

FOREIGN PATENT DOCUMENTS

| | | |
|---|---|---|
| WO | WO 2006/020942 | 2/2006 |
| WO | WO 2016/097976 | 6/2016 |
| WO | WO 2016/185473 | 11/2016 |
| WO | WO 2018/067410 | 4/2018 |
| WO | WO 2018/209191 | 11/2018 |
| WO | WO 2018/223060 | 12/2018 |
| WO | WO 2019/195480 | 10/2019 |
| WO | WO 2020/264417 | 12/2020 |

OTHER PUBLICATIONS

U.S. Appl. No. 16/338,961, filed Apr. 2, 2019, Korakianitis et al.
U.S. Appl. No. 15/720,592, filed Sep. 29, 2017, Korakianitis et al.
U.S. Appl. No. 16/914,019, filed Jun. 26, 2020, Korakianitis et al.
Search Report and Written Opinion for PCT/US2017/054573 dated Dec. 15, 2017 in 14 pages.
Extended European Search Report for EP 17858942.0 dated Jul. 23, 2020 in 14 pages.
Partial Supplementary European Search Report for EP 17858942.0 dated Apr. 22, 2020 in 18 pages.
Search Report and Written Opinion for PCT/US2018/035694 dated Nov. 5, 2018 in 12 pages.
Search Report and Written Opinion for PCT/US2019/025667 dated Jul. 29, 2019 in 19 pages.
Search Report and Written Opinion for PCT/US2020/039978 dated Nov. 20, 2020 in 25 pages.
Invitation to Pay Additional Fees for PCT/US20/39978 dated Sep. 15, 2020.
Partial Supplementary European Search Report for EP 18809622.6 dated Jan. 12, 2021 in 22 pages.
Office Action for IN 202017047035 dated Sep. 23, 2022.
Extended European Search Report for EP 19780961.9 dated Nov. 26, 2021 in 8 pages.
Hosseinipour, M., et al. (2017). Rotary mechanical circulatory support systems. Journal of Rehabilitation and Assistive Technologies Engineering, 2017, vol. 4: 1-24. https://doi.org/10.1177/2055668317725994.
Mieghem et al. (2018). Design and principle of operation of the HeartMate PHP (percutaneous heart pump). EuroIntervention 2018,13,1662-1666 published online Dec. 2016. DOI: 10.4244/EIJ-D-15-00467.
Miller, L., et al. (2019). Use of Ventricular Assist Devices and Heart Transplantation for Advanced Heart Failure. Circulation Research, 2019;124:1658-1678. DOI: 10.1161/CIRCRESAHA.119.313574.
Siess, T., et al (2001). From a Lab Type to a Product: A Retrospective View on Impella's Assist Technology. Artificial Organs, 2001, 25(5):414-421.
Yancy CW, Jessup M, Bozkurt B, et al. 2013 ACCF/AHA guideline for the management of heart failure: a report of the American College of Cardiology Foundation/American Heart Association Task Force on practice guidelines. Circulation. Oct. 15, 2013;128(16):e240-327, also published in J Am Coll Cardiol Oct. 15, 2013;62(16):e147full-text.
Lund LH, Edwards LB, Kucheryavaya AY, Dipchand AI, Benden C, Christie JD, Dobbels F, Kirk R, Rahmel AO, Yusen RD, Stehlik J, International Society for Heart and Lung Transplantation. The Registry of the International Society for Heart and Lung Transplantation: Thirtieth Official Adult Heart Transplant Report—2013; focus theme: age. Journal of Heart and Lung Transplantation Oct. 2013;32(10):951-64.
Lund, L.H., Edwards, L.B., Dipchand, A.I., Goldfarb, S., Kucheryavaya, A.Y., Levvey, B.J., Meiser, B., Rossano, J.W., Yusen, R.D., Stehlik, J. The Registry of the International Society for Heart and Lung Transplantation: Thirty-third Adult Heart Transplantation Report—2016; Focus Theme: Primary Diagnostic Indications for Transplant vol. 35, Issue 10, Oct. 1, 2016, pp. 1158-1169.
Fonarow GC, Abraham WT, Albert N, Gattis W, Gheorghiade M, Greenberg B, O'Connor CM, She L, Yancy CW, Young JB. Organized program to initiate lifesaving treatment in hospitalized patients with heart failure (OPTIMIZE-HF): rationale and design American Heart Journal. vol. 148, Issue 1, Jul. 2004, pp. 43-51 https://doi.org/10.1016/j.ahj.2004.03.004.
Gheorghiade M, Zannad F, Sopko G, Klein L, Pina IL, Konstam MA, et al. Acute heart failure syndromes: current state and framework for future research. Circulation 2005;112(25): 3958-68.
Rangaswami et al. Cardiorenal Syndrome: Classification, Pathophysiology, Diagnosis, and Treatment Strategies: A Scientific Statement from the American Heart Association. Circulation. 2019;139:e840-e878.
Benjamin et al. Heart Disease and Stroke Statistics—2017 Update: A Report From the American Heart Association. Circulation. 2017. (Part 1 of 5).
Benjamin et al. Heart Disease and Stroke Statistics—2017 Update: A Report From the American Heart Association. Circulation. 2017. (Part 2 of 5).
Benjamin et al. Heart Disease and Stroke Statistics—2017 Update: A Report From the American Heart Association. Circulation. 2017. (Part 3 of 5).
Benjamin et al. Heart Disease and Stroke Statistics—2017 Update: A Report From the American Heart Association. Circulation. 2017. (Part 4 of 5).
Benjamin et al. Heart Disease and Stroke Statistics—2017 Update: A Report From the American Heart Association. Circulation. 2017. (Part 5 of 5).
Gheorghiade M. et al., Rehospitalization for heart failure: problems and perspectives. JACC vol. 61, No. 4, 2013: 391-403.
Optimization of Centrifugal Pump Characteristic Dimensions for Mechanical Circulatory Support Devices. ASAIO Journal Korakianitis T., Rezaienia M.A., Paul G., Rahideh, A., Rothman M.T., and Mozafari S. (2016) DOI: 10.1097/MAT.0000000000000393.
In Vitro Cardiovascular System Emulator (Bioreactor) for the Simulation of Normal and Diseased Conditions With and Without Mechanical Circulatory Support Ruiz P., Rezaienia M.A., Rahideh A., Keeble T.R., Rothman M.T., and Korakianitis T. Artificial Organs, vol. 37, No. 6, 2013, p. 549-560, doi:10.1111/aor.12109.
In-vitro investigation of cerebral-perfusion effects of a rotary blood pump installed in the descending aorta Rezaienia M.A., Paul G., Avital E., Rahideh A., Rothman M.T., and Korakianitis T. Journal of Biomechanics, vol. 49, p. 1865-1872, 2016. http://dx.doi.org/10.1016/j.jbiomech.2016.04.027.
In-vitro investigation of the hemodynamic responses of the cerebral, coronary and renal circulations with a rotary blood pump installed in the descending aorta Rezaienia M.A., Paul G., Avital E.J., Mozafari S., Rothman M., and Korakianitis T. Medical Engineering and Physics, vol. 40, pp. 2-10, 2017. http://dx.doi.org/10.1016/j.medengphy.2016.11.006.
Chang B. Y, Keller S. P., Bhavsar S. S., Josephy N. and Edelman E. R. Mechanical circulatory support device—heart hysteretic inter-

(56) References Cited

OTHER PUBLICATIONS action can predict left ventricular end diastolic pressure Sci Transl Med. Feb. 28, 2018; 10(430) 2018 doi:10.1126/scitranslmed.aao2980.

Initial tests with a new cardiac assist device. Reitan O., Ohlin H., Peterzen B., Granfeldt H., Steen S., and Emanuelsson H. ASAIO Journal vol. 45, 317-321, 1999.

Hydrodynamic Properties of a New Percutaneous Intra-aortic Axial Flow Pump. Reitan O., Sternby J., and Ohlin H. ASAIO Journal vol. 46, 323-329, May-Jun. 2000.

Hemodynamic Effects of a New Percutaneous Circulatory Support Device in a Left Ventricular Failure Model Reitan O., Steen S., and Ohlin H. ASAIO Journal Nov.-Dec. 2003, vol. 49, No. 6, 731-736. DOI: 10.1097/01.MAT.0000093964.33468.CA.

An Expandable Percutaneous Catheter Pump for Left Ventricular Support—Proof of Concept Thomas Schmitz-Rode, Jurgen Graf, Joachim G. Pfeffer, Frank Buss, Christoph Brucker, Rolf W. Günther Journal of the American College of Cardiology. vol. 45, No. 11 ,2005 doi:10.1016/j.jacc.2005.02.071.

\* cited by examiner

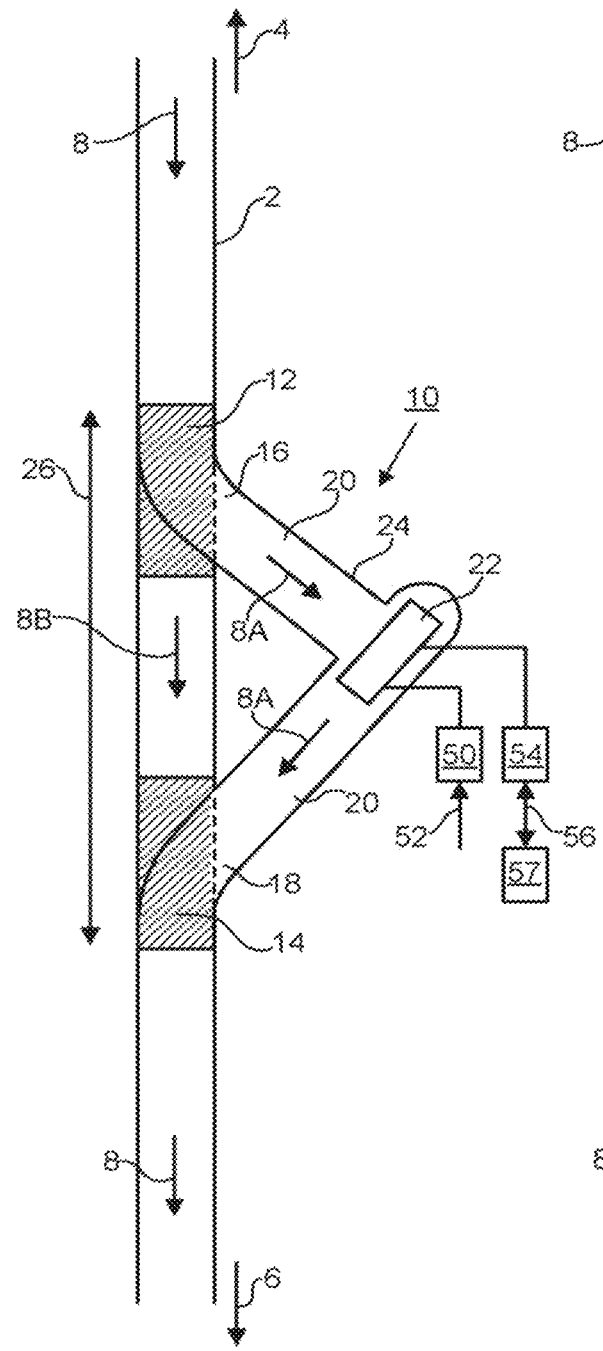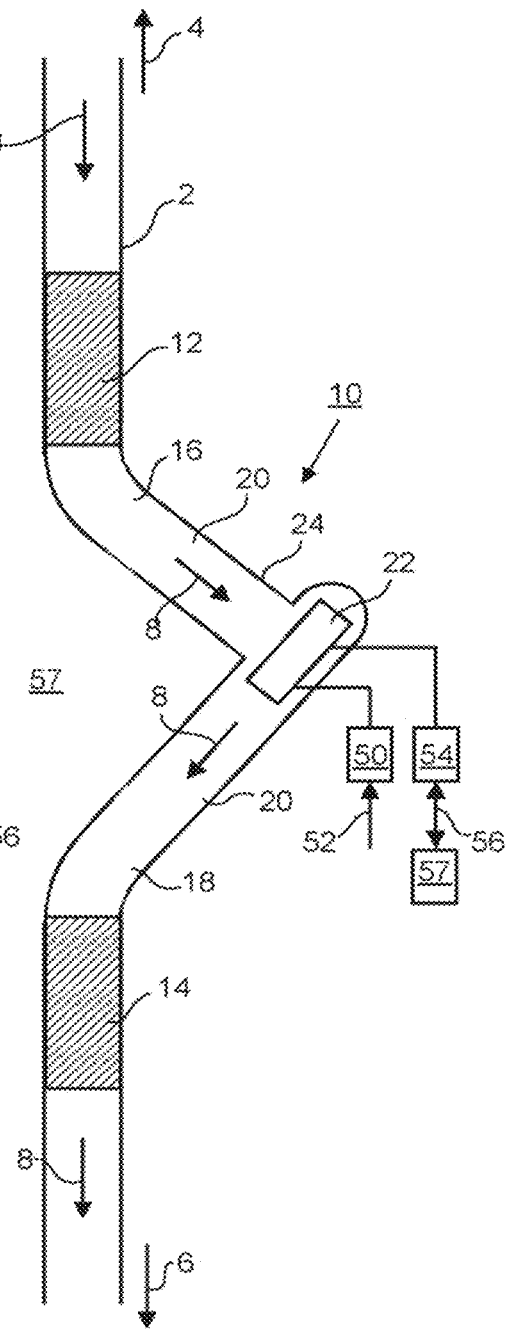

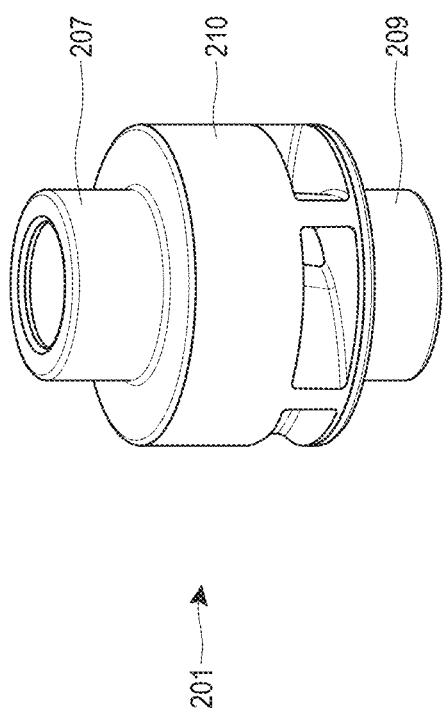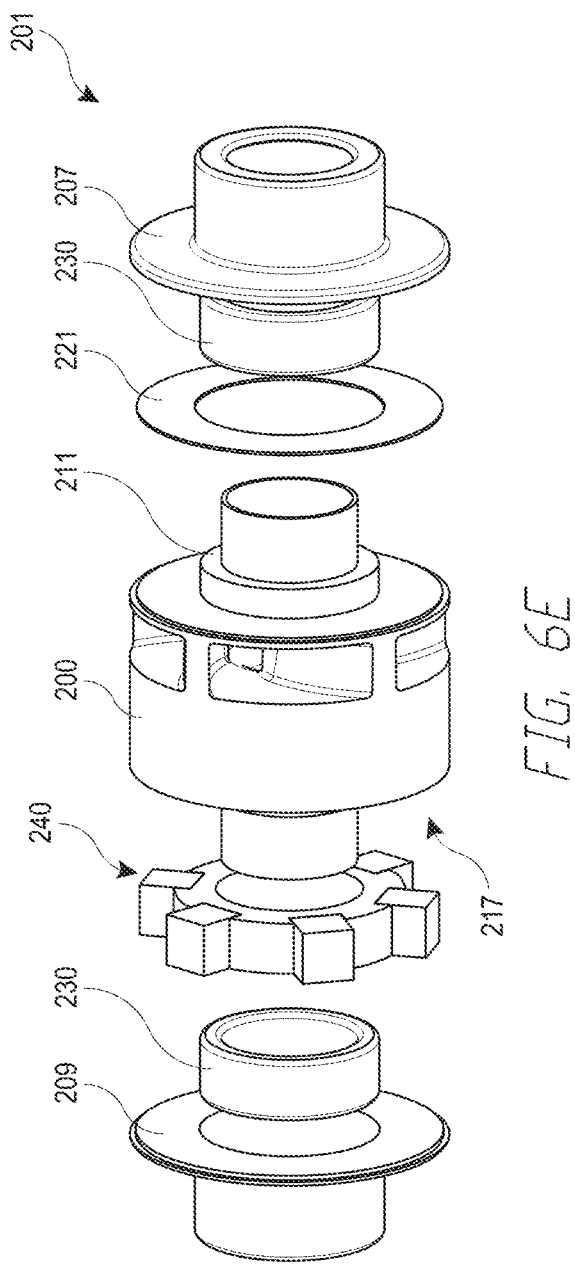

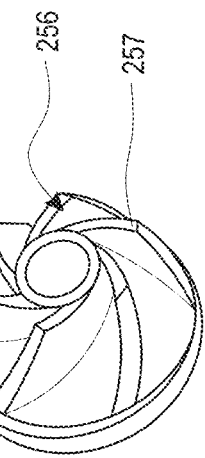
FIG. 7D
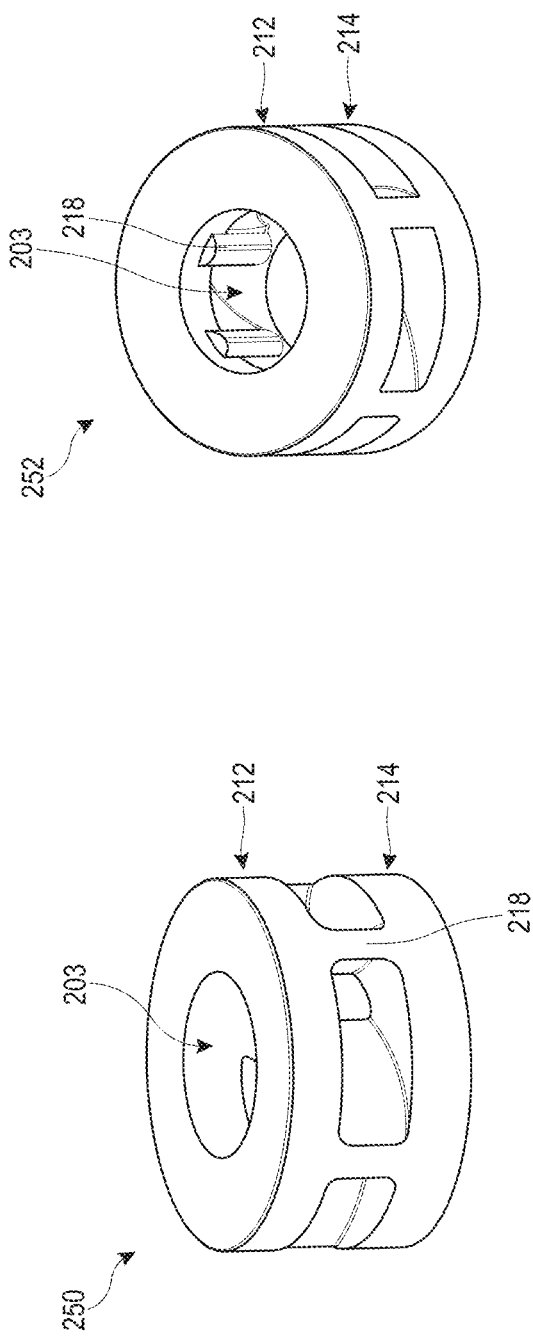
FIG. 7B
FIG. 7C
FIG. 7A
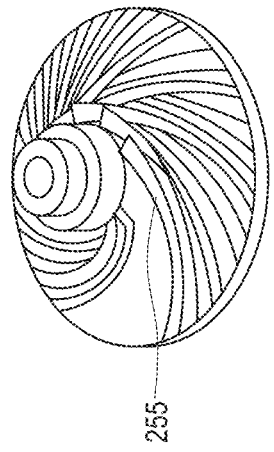

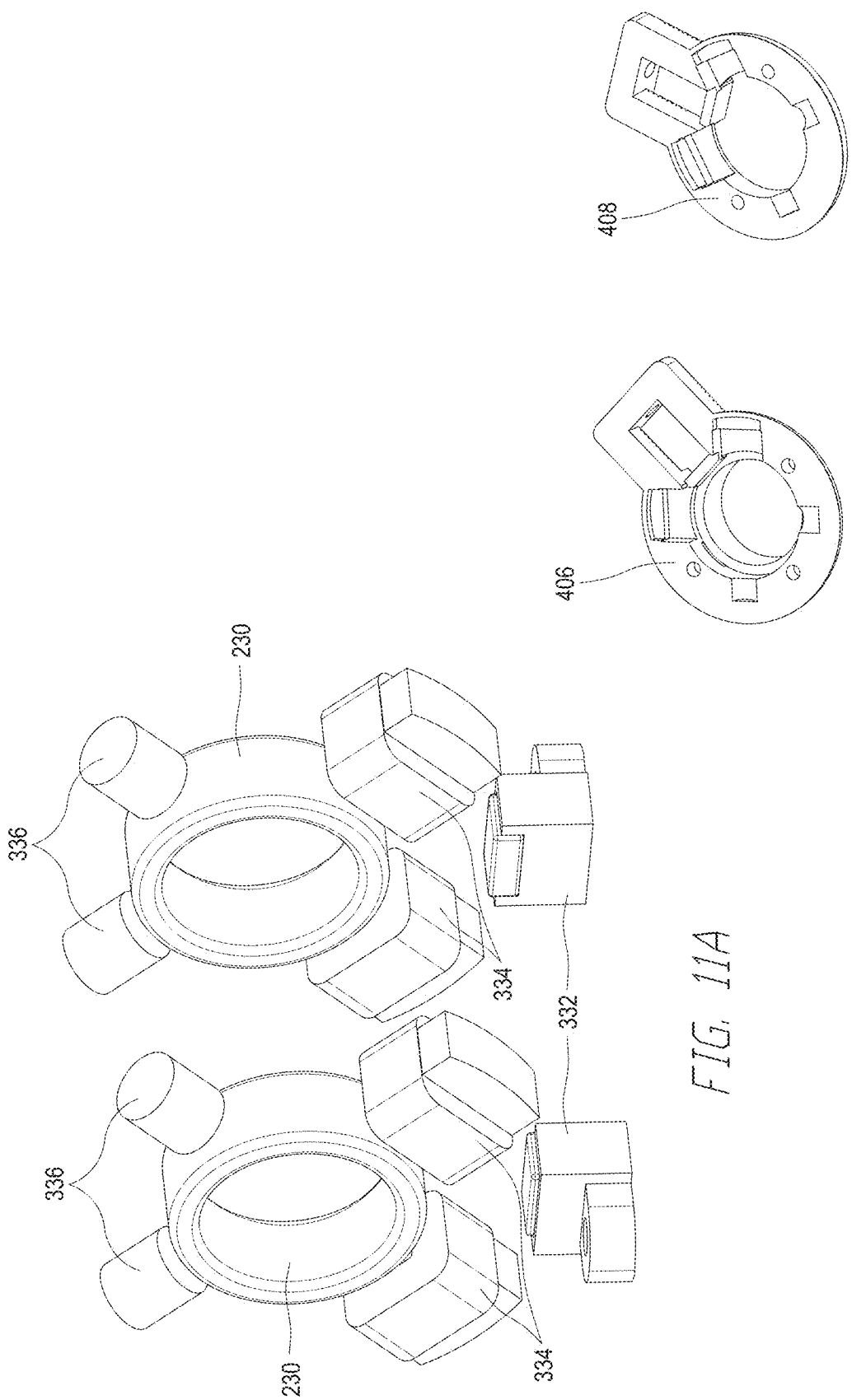
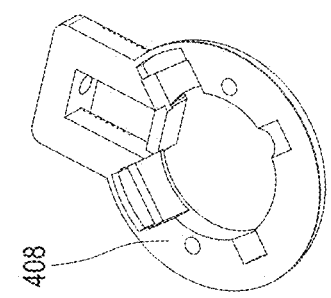
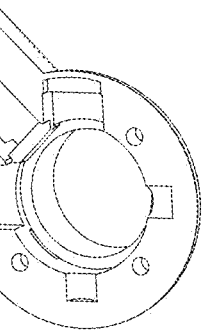
FIG. 11A
FIG. 11B
FIG. 11C

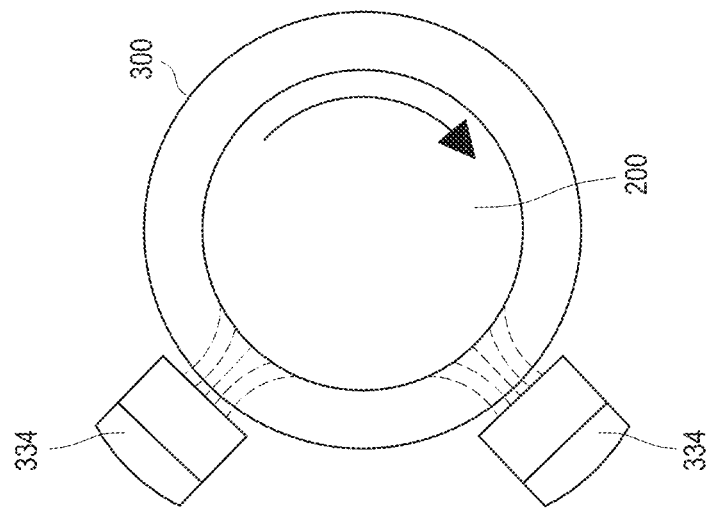
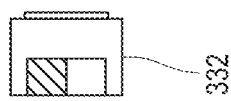
FIG. 12B
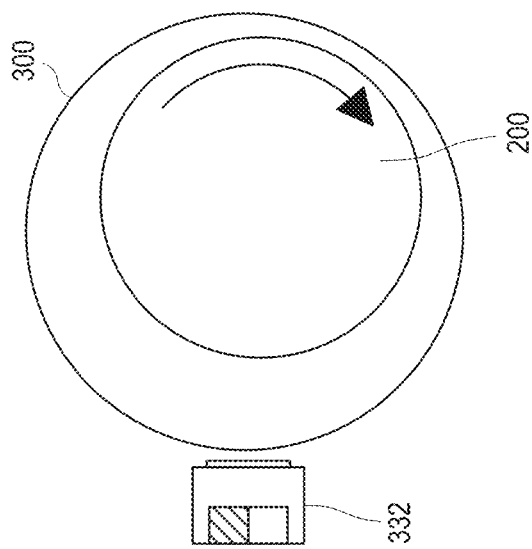
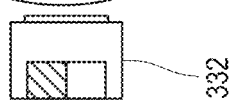
FIG. 12A

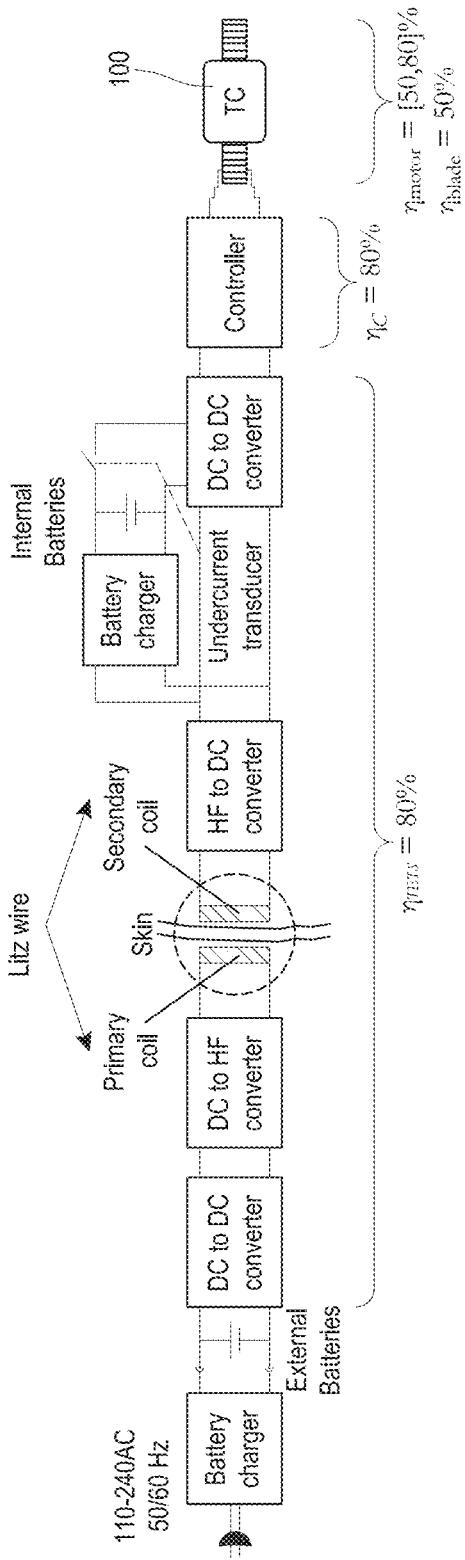
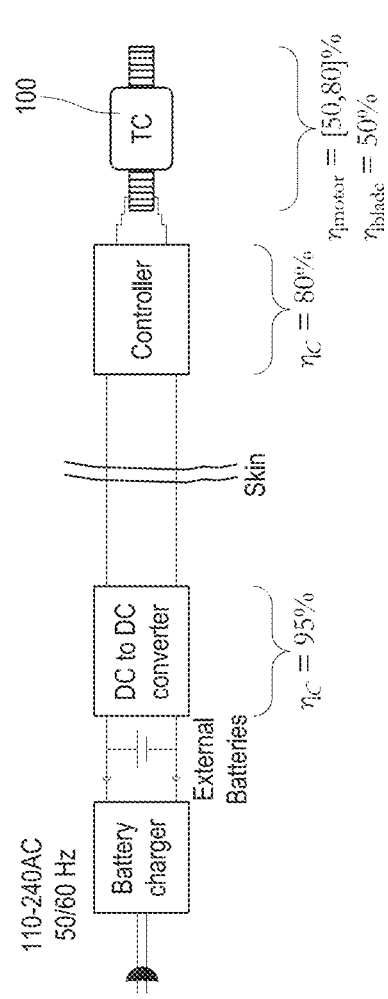
FIG. 16A
FIG. 16B

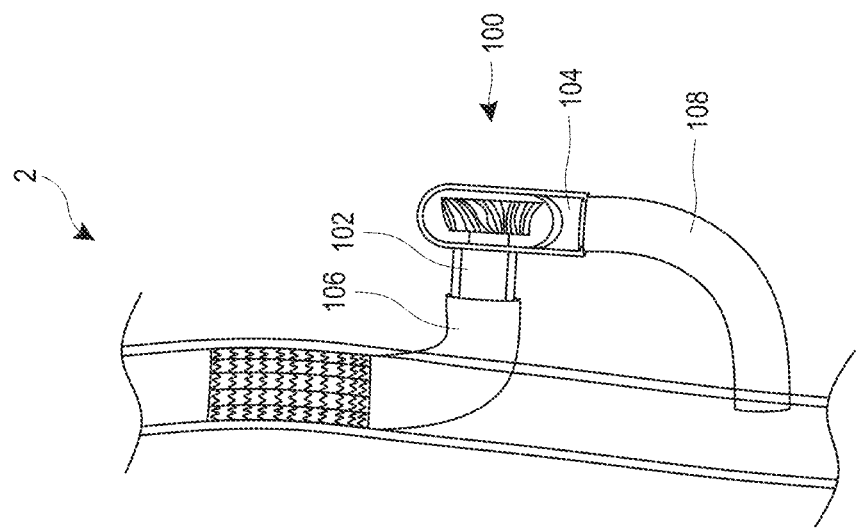
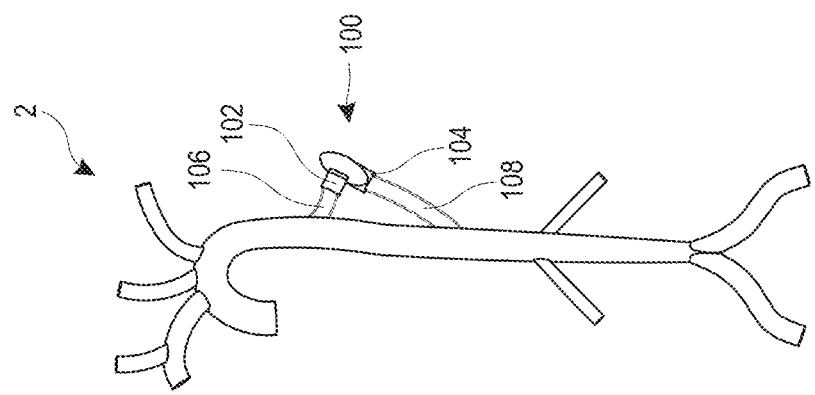
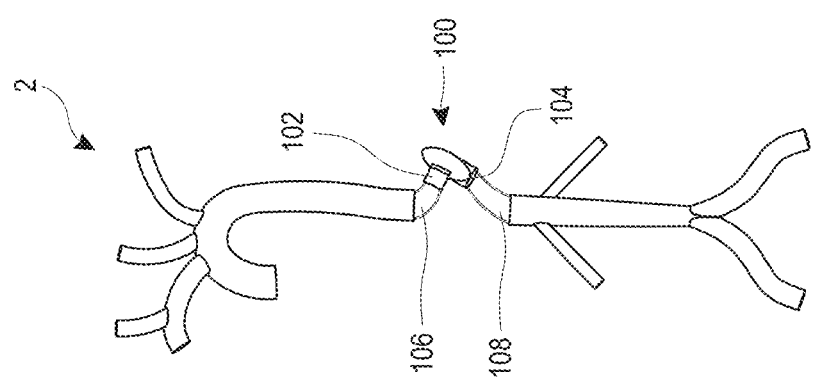

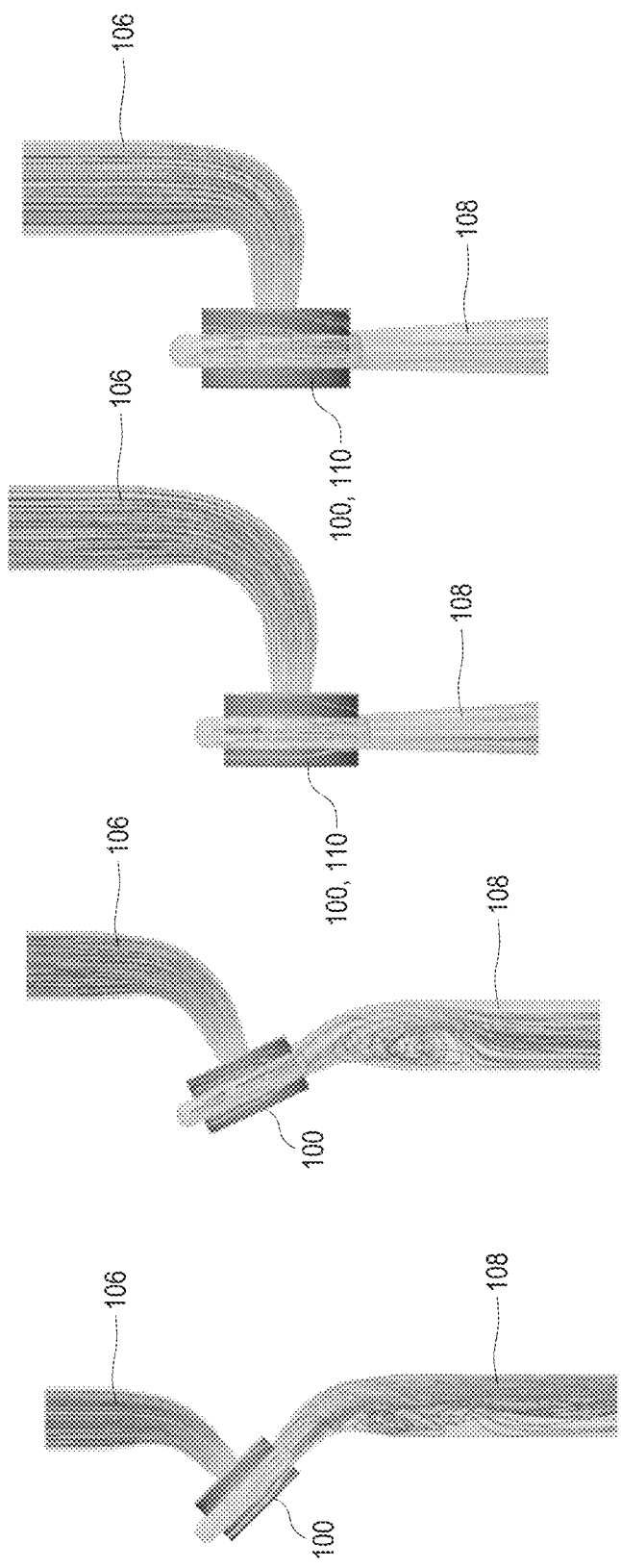

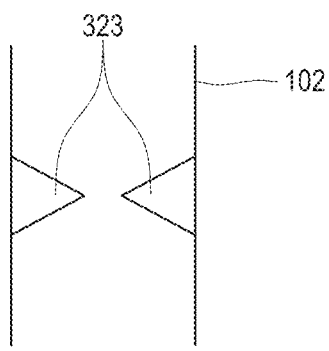
FIG. 23A
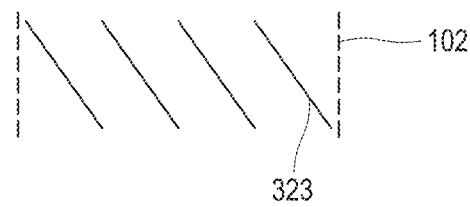
FIG. 23B
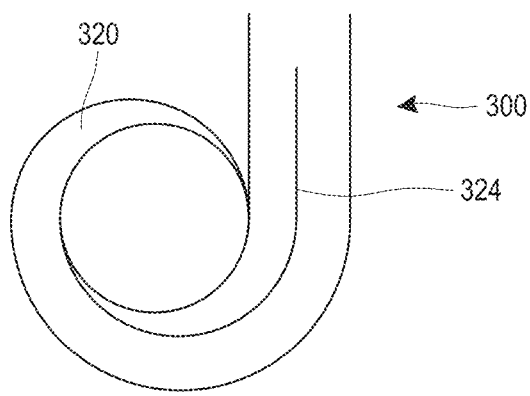
FIG. 23C
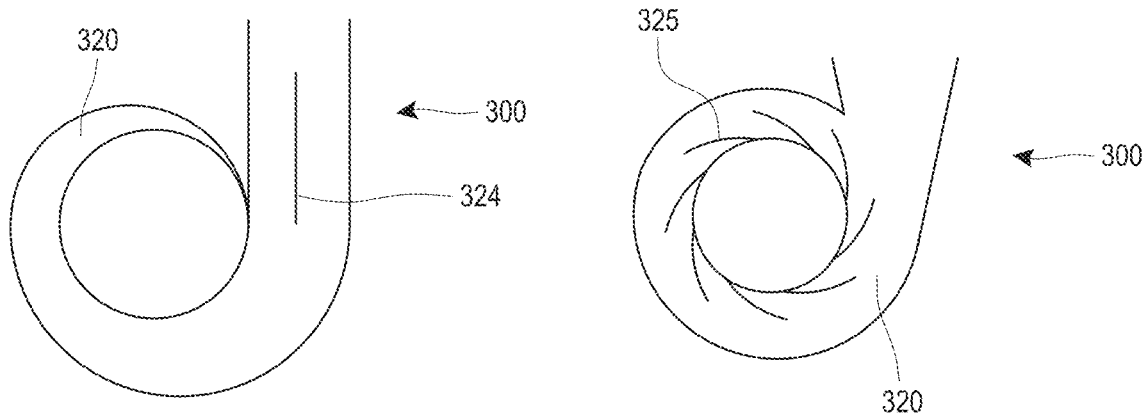
FIG. 23D
FIG. 23E

MECHANICAL CIRCULATORY SUPPORT DEVICE WITH CENTRIFUGAL IMPELLER DESIGNED FOR IMPLANTATION IN THE DESCENDING AORTA

INCORPORATION BY REFERENCE

This application is a continuation of U.S. patent application Ser. No. 15/619,335, filed Jun. 9, 2017 which is a continuation-in-part of U.S. patent application Ser. No. 14/440,848, filed May 5, 2015, which is a U.S. national phase of PCT/GB2013/052889, filed Nov. 5, 2013, which claims priority to GB application No. 1219958.4, filed Nov. 6, 2012, which references are incorporated herein by reference in its entirety for all purposes. U.S. patent application Ser. No. 15/619,335 also claims priority benefit of U.S. Provisional Patent Application No. 62/403,428, filed Oct. 3, 2016, and U.S. Provisional Patent Application No. 62/513,927, filed Jun. 1, 2017, each of which is incorporated herein by reference in its entirety for all purposes. Any and all applications related thereto by way of priority thereto or therefrom are hereby incorporated by reference in their entirety.

BACKGROUND

The present invention relates to a mechanical circulatory support (MCS), otherwise known as a mechanical circulatory support device (MCSD), for assisting or replacing native heart function in cases of congestive heart failure (CHF).

Patients with CHF usually have a low cardiac output state as the native heart functions (pumps) poorly. This in turn leads to poor organ perfusion and the symptoms of heart failure including fatigue, breathlessness and feeling generally unwell. In heart failure the kidneys also suffer with poor perfusion and their function often deteriorates considerably (a condition called "the cardio-renal syndrome"). Poor kidney function means that patients feel more unwell, and important drugs have to be withdrawn as they can further adversely affect kidney function.

CHF is common and is a significant health care burden. It is graded from stage I-IV in severity. Once diagnosed a patient has 4-5 years of progression from stage I to IV and death. Stage IV patients are breathless at rest, candidates for heart transplantation, and medication is considered palliative. Congestive heart failure (CHF) is the main cause of mortality for men and women alike in the western world, affecting about 2% of the population. In the USA alone there are 5.7 million patients suffering from CHF and costs to treat this exceed $37.2 billion/year. In the Western world current supply of donor hearts only meets about 12% of demand. This percentage is higher than the actual number because most potential recipients are not included in the calculation; they are considered not suitable for a transplant because of co-morbidities or lack of a matched donor. This shortfall has resulted in the development of MCS devices as a transplant alternative. MCS devices are expensive and require invasive cardiac surgery (sternotomy or thoracotomy). Implantation carries a significant risk. Not all candidates are suitable for MCS because of co-morbidities.

Most permanent MCS devices assist the ventricle and are attached to it in use. These are called Ventricular Assist Devices (VADs), and are designed to drive a flow of blood that is in parallel with flow within the native heart, between the ventricle and the aorta. In other words, they are designed as left (or right) ventricular assist devices (LVADs or RVADs), pumping devices that directly unload the respective ventricle. Such "in-parallel" configurations involve the device and heart sharing, and therefore competing, for inlet flow, which can disrupt normal functioning of the heart. Regeneration of heart muscle may be impeded and the heart is not able to pump to its best capacity. The inlet of most of these VADs is anastomosed to the apex of the left ventricle of the heart, and therefore their installation requires major sternotomy or thoracotomy and cardiopulmonary bypass (CPB), i.e. stopping of the heart during a prolonged surgical operation, for permanent installation. Survival rates of patients on VADs have been poor.

Due to inefficiencies, existing MCS/VAD devices typically require significantly more input power than is necessary from a theoretical point of view purely to impart the desired momentum to the blood. The excess power is used to overcome the losses. The portion of the power that is used to overcome flow losses is imparted as unnecessary damage to the blood, leading to increased levels of haemolysis and/or thrombus formation that would be avoided with devices having higher fluid dynamic efficiency.

VADs entered clinical use as displacement (or pulsatile flow) devices, which mimic the native left ventricle by providing pulsatile flow taking over the function of the patient's own left ventricle. Most widely used displacement, pulsatile, devices have been extracorporeal devices such as the BVS® 5000 VAD of Abiomed, Inc. (Danvers, Mass., USA) and the Thoratec VAD of Thoratec Corporation (Pleasanton, Calif., USA), and intracoporeal devices such as the Novacorx LVA System of WorldHeart, Inc. (Oakland, Calif., USA), the HeartMate IP and VE/XVE of Thoratec Corporation. Although the large external pneumatic consoles of the first-generation displacement VADs have been replaced by implantable electric systems with a portable controller and power source, the serious problems of device weight (e.g., approximately 1.5 kg for the HeartMate XVE), size, noise, driveline infection and thromboembolism persist. Consequently, newer displacement devices are totally implantable, such as the LionHeart™ VAD of Arrow International, Inc. (Reading, Pa., USA), and the Novacor® LVA System of WorldHeart, Inc. (Oakland, Calif., USA).

Rotary (or continuous flow) devices (second-generation VADs) have been developed to overcome the shortcomings of pulsatile devices. Initial concerns with their pulseless flow are now overcome, provided that the patient's native system still provides some pulsatility, and they have their own relative advantages (e.g., fewer moving parts, lower power required, absence of bioprosthetic valves) and disadvantages (e.g., complex control, high afterload and low preload sensitivity, and haemolysis and thrombosis from unnatural flow patterns). Examples of axial rotary pumps (which operate at 10,000-20,000 rpm) are the DeBakey VAD® of MicroMed Cardiovascular, Inc. (Houston, Tex., USA), the FlowMaker® of Jarvik Heart, Inc. (New York, N.Y., USA), formerly known as Jarvik 2000, the HeartMate II of Thoratec Corporation (Pleasanton, Calif., USA), and the Impella Recover® system of Impella CardioSystems AG (Aachen, Germany) intended for short-term circulatory support for up to seven days. These existing devices attempt to provide total flow and pressure capacity, forcing the pump to operate in inefficient flow regimes.

Centrifugal or radial flow blood pumps are generally somewhat larger than axial flow devices and provide non-pulsatile flow, but the rotational speeds are generally much slower (2,000-10,000 rpm) than axial flow blood pumps. While axial flow blood pumps are the smallest VAD, they are higher speed lower pressure rise devices, while centrifugal VADs are better suited to take over heart function and to provide total pressure rise and flow (about 120 mmHg and 5 L/min). Examples are the Gyro C1E3 of Kyocera Corporation (Kyoto, Japan) which evolved into the NEDO PI-601 pump (animal studies).

Third-generation VADs are those that have replaced the mechanical bearings of second generation ones with hydrodynamic or magnetic-suspension bearings. Examples of axial flow VADS are: the INCOR® LVAD of Berlin Heart AG (Berlin, Germany); the MicroVad currently under development at Helmholtz-Institute for Biomedical Engineering (Aachen, Germany); and the MagneVAD I and II of Gold Medical Technologies, Inc. (Valhalla, N.Y., USA). Examples of centrifugal flow VADs are: the HVAD of HeartWare Ltd (Sydney, NSW, Australia); the EVAHEART™ of Evaheart Medical USA, Inc. (Pittsburgh, Pa., USA); the VentrAssist LVAD of Ventracor Ltd (Chatswood, NSW, Australia); the CorAide™ LVAD of Arrow International (Reading, Pa., USA); the DuraHeart of Terumo Heart, Inc. (Ann Arbor, Mich., USA); the HeartQuest VAD of WorldHeart, Inc. (Oakland, Calif., USA); the HeartMate III of Thoratec Corporation (Pleasanton, Calif., USA); and the MiTiHeart™ LVAD of Mohawk Innovative Technology, Inc. (Albany, N.Y., USA). All the above devices require major sternotomy or otherwise invasive surgery and CPB.

Other examples of previous devices can be found in the following patents, each of which is hereby incorporated by reference: U.S. Pat. Nos. 4,625,712; 4,779,614; 4,846,152; 5,267,940; 6,632,169, 6,866,625; 7,238,151; 7,485,104; 8,075,472; 8,371,997; 8,545,380; 8,562,509; 8,585,572; 8,597,170; 8,684,904; 8,690,749; 8,727,959; 8,734,508; 8,814,933; 8,870,552; 8,900,115; 8,961,389; 9,028,392; 9,107,992; 9,138,518; 9,162,018; 9,211,368; 9,295,550; 9,339,597; 9,364,593; 9,370,613; 9,387,285; 9,474,840; 9,555,175; 9,572,915; 9,579,433; and 9,597,437.

SUMMARY

It is an object of the invention to provide a device that can be installed with less risk to the patient, which reduces disruption to normal functioning of the heart and/or which minimizes damage to the blood.

According to an aspect of the invention, there is provided a mechanical circulatory support, comprising: a body portion defining an internal lumen; an inlet port in fluid communication with the lumen; an outlet port in fluid communication with the lumen; and a pump for driving fluid flow from the inlet port towards the outlet port, wherein: the inlet port is arranged to provide a connection, or is in a state of connection, into the aorta of a human body.

This arrangement does not require any connections to be made directly to the heart and can be installed using minimally invasive surgery, greatly reducing the risks associated with installation relative to arrangements that need to be connected directly to the heart. There is no need to perform a cardiopulmonary bypass for example. The reduced installation risk makes the device more suitable for treatment of earlier stage CHF than existing MCS/VAD devices, for example early stage IV CHF. In some embodiments, the device may be suitable for treating stage III or stage IV CHF. The device may be particularly suited to treat late stage III CHF or early stage IV CHF.

The outlet port may be connected to a downstream position in the aorta so as to be connected in series with the native heart. This type of connection is less disruptive to the normal functioning of the heart than systems which work in parallel with the heart and may help to promote regeneration of the heart muscle. Additionally or alternatively, by allowing the native heart to pump to its best capacity the additional pumping power required by the support may be reduced.

In an embodiment, the series connection is implemented by connecting the support in parallel with a small section of the descending aorta. In an alternative embodiment, the descending aorta is interrupted so that all of the blood flow passes through the support.

In other embodiments, the outlet port is connected at other positions in the vasculature, for example in the ascending aorta. In an embodiment, the support comprises one outlet port in the descending aorta and one outlet port in the ascending aorta. In this way, a proportion of the outflow is provided to the ascending aorta to support coronary flow more directly. In an embodiment, the inlet port is connected to one or more other strategic locations such as the ascending aorta, and the outlet port(s) connected as previously described into the descending aorta, the ascending aorta, or both. The descending aorta outlet has additional advantages for renal, splanchnic, and other organ perfusion without affecting brain flow.

In an embodiment, the pump is a centrifugal pump. The inventors have discovered that such pumps can provide particularly effective impetus to the circulating blood. In particular, unnecessary blood shear and fluid-dynamic diffusion (the effect of pressure rise as flow decelerates along the device passage) and turbulence can be minimized, which in turn minimizes the imposed shear stress to blood cells, thus minimizing blood cell lysis (haemolysis) and thrombus formation. The improved pumping efficiency reduces power requirements, enabling the power supply to be made smaller and more comfortable to carry. In addition, the pump itself can be made more compact. In an alternative embodiment, the pump is a mixed flow pump (e.g. a pump having characteristics intermediate between a centrifugal pump and an axial pump). In a still further embodiment, the pump is a helical pump. In a still further embodiment, the pump is an axial pump.

In an embodiment, the pump is configured to provide a continuous, rather than pulsatile flow. The inventors have realised that it is not necessary for the pump to mimic the pulsatile flow imparted by the native heart, particularly when installed so as to work in series with the heart. The pump can thus interact more smoothly with the blood flow, further minimizing damage to the blood. Additionally, the efficiency of a continuous pump can be optimized further than a pulsatile pump. Acceleration and deceleration of the blood is reduced, which reduces the stresses that need to be applied to the blood as well as the needed power input to the pump. In alternative embodiments the pump is configured to provide a pulsatile flow (synchronous or asynchronous or different fixed phase or variable phase with the heart).

In an embodiment, the support comprises a power receiving member that is configured to receive power for driving the pump transcutaneously, for example by electromagnetic induction. Alternatively or additionally, power can be supplied percutaneously.

According to an aspect of the invention, there is provided a mechanical circulatory support, comprising: a pump configured to be installed, or in a state of installation, in a human body and configured to operate in series with the native heart; and a device for electromagnetically driving the pump that is configured to be mounted to the body. Thus, a support is provided that is suitable for "permanent" installation (e.g. so that the patient can leave the hospital with the support installed and operational) and which provides a pumping action that is in series, rather than in parallel, with the native heart.

MCSs which generate full physiological pressure rises (about 120 mmHg), such as VADs in-parallel with the heart, may impart tremendous damage to the blood (e.g., haemolysis), especially in later stages of CHF. MCSs which are installed in-series with the heart (i.e. the left ventricle) may exploit the existing pressure rise of the native heart and provide an additive pressure rise. Disclosed herein are embodiments of MCSs configured for in-series installation in the aorta, particularly the descending aorta. Installation within the descending aorta advantageously is conducive to installation via minimally invasive surgery (e.g., percutaneous installation or thoracoscopy), which produces better outcomes (e.g., reduced morbidity) and shorter recovery periods for patients, especially those suffering CHF. Additionally, minimally invasive surgical procedures may generally be performed at district hospitals by vascular surgeons, unlike the sternoscopy procedures that are generally necessary for installation of VADs, which usually must be performed by cardiothoracic surgeons in critical care units. Installation within the descending aorta is further advantageous because the MCS intercept location is downstream of the cerebral blood flow, fed by the carotid arteries, reducing the risk of cerebral thromboembolism or stroke. Any blood damaged by an MCS installed in the descending aorta is pumped to the renal inflow arteries and remaining systemic and pulmonary perfusion system prior to reaching the cerebral blood flow. MCSs which are installed in the descending aorta must be careful not to establish such a large pressure rise that upstream blood perfusion to the cerebral blood flow is not suppressed, or stolen, by the suction of the MCS.

MCSs may be designed with operating conditions specifically configured for particular stages of CHF. For instance, a MCS designed for late stage II or early stage III CHF may provide a 20-50 mmHg pressure rise, while a MCS designed for late stage III or early stage IV CHF may provide a 40-80 mmHg pressure rise, to better supplant the failing heart. The reduced pressure requirements of MCSs that are installed in-series with the heart may effectively reduce the load on the heart (afterload reduction) by lowering the resistance to blood flow, which can advantageously provide the heart increased potential for regeneration of diseased tissue. MCSs with less than full physiological pressure rises generally will require less power and will be smaller and lighter weight than MCSs such as VADs which generate larger pressure rises. MCSs installed in series may be configured to maintain the physiological flow rate of a healthy individual of about 5 L/min. The MCSs may pump blood at a continuous flow, while the native heart may maintain pulsatility in total perfusion. In alternative embodiments, the MCS may provide a pulsatile flow. Such pulsatile flow may be established, for example, by axially oscillating the impeller within the MCS casing.

Turbomachines operate efficiently over only a very narrow regime of pressure rise, flow rate and rotational speed specifications, all of which translate into a narrow regime of optimal angles of attack (angle of incoming flow) to turbomachinery airfoils. Therefore, a turbomachine configured, for example, to generate a 120 mmHg pressure rise, such as a VAD designed for in-parallel implantation with the left ventricle, will operate substantially less efficient if instead installed in the descending aorta and operated at a much lower pressure differential (e.g., 70 mm Hg). For instance, operating a turbomachine below its configured pressure differential will: operate at a much different than as-designed pressure rise, flow rate, and rotational speed; operate away from the as-designed optimal condition for angles of attack to turbomachine blades; will not work efficiently; and will create unnecessary blood shear, turbulence, stall and losses. These deviations from optimal as-designed operating conditions will increase blood trauma and reduce device efficiency and efficacy for use in this location.

Disclosed herein are embodiments of MCS devices and systems along with methods of installing and/or using MCS devices to treat CHF. In various embodiments, the MCS is a centrifugal pump, comprising an impeller suspended in a casing, an inlet introducing blood flow from the native vasculature to the impeller in an axial direction, and a diffuser with an entrance positioned along the circumference of the impeller and an outlet returning blood flow to the native vasculature. The impeller may be magnetically suspended in a contactless manner within the casing and rotated using an electromagnetic motor. An external controller implanted within the body may provide power to the MCS and control the electrical operations. The MCS may be powered by internal and/or external batteries. The internal batteries may be recharged and/or power may be delivered from external batteries through transcutaneous or percutaneous energy transfer systems. In various embodiments, the MCS is specifically suited for late stage III and/or early stage IV CHF and generates pressures rises between about 40 to about 80 mmHg and maintains a flow rate of approximately 5 L/min.

BRIEF DESCRIPTION OF THE DRAWINGS

Embodiments of the invention will now be described, by way of example only, with reference to the accompanying drawings in which corresponding reference symbols indicate corresponding parts, and in which:

FIG. 1 depicts a mechanical circulatory support connected to a section of vasculature and configured to drive fluid flow in parallel with a small portion of the native blood vessel.

FIG. 2 depicts an alternative configuration for the mechanical circulatory support of FIG. 1 in which the support drives blood flow that is entirely in series with the native blood vessel, bypassing a short portion of the native blood vessel.

FIG. 5A illustrates a perspective view of an MCS. FIG. 5B depicts a photograph of an MCS prototype. FIG. 5C illustrates a side cross-sectional view of the MCS. FIG. 5D schematically illustrates a simplified side-cross-section of the MCS 100 along with example dimensions (in mm) of various components and spacing.

FIGS. 6A-6E illustrate an example of an impeller. FIG. 6A illustrates a perspective view of an example of an impeller configured to be used with an MCS. FIG. 6B illustrates a side cross section of the impeller. FIG. 6C illustrates a top cross section of the impeller. FIG. 6D illustrates a perspective view of an impeller assembly including a top cap and a bottom cap. FIG. 6E illustrates an exploded view of the impeller assembly in FIG. 6D.

FIGS. 7A-7D illustrate perspective views of further examples of impellers. FIG. 7A illustrates an example of a shrouded impeller. FIG. 7B illustrates another example of a shrouded impeller. FIG. 7C illustrates an example of an unshrouded impeller. FIG. 7D illustrates another example of an unshrouded impeller.

FIG. 8A illustrates an exploded view of an example of an MCS casing. FIG. 8B illustrates a bottom view of the casing upper volute shown in FIG. 8A. FIG. 8C illustrates a perspective view of the casing lower volute shown in FIG. 8A. FIG. 8D illustrates a perspective view of another example of an MCS casing. FIG. 8E illustrates an exploded view of an example of an MCS impeller with inner and outer casings.

FIG. 10A illustrates an example of the relative positioning of axial-suspension magnets. FIG. 10B illustrates an example of an upper axial magnet holder.

FIG. 10C illustrates an example of a lower axial magnet holder. FIG. 10D schematically illustrates the adjustability of the axial magnet holders relative to the ring magnets positioned on an MCS impeller.

FIGS. 11A-11E illustrate example components of an MCS magnetic radial suspension system. FIG. 11A illustrates an example of the relative positioning of radial suspension magnets and eddy current sensors. FIG. 11B illustrates an example of a top radial magnet holder. FIG. 11C illustrates an example of a bottom radial magnet holder.

FIG. 11D illustrates an example of the upper radial suspension components seated on an MCS casing lid. FIG. 11E illustrates an example of the lower radial suspension components seated on an MCS casing lower volute.

FIGS. 12A-12B schematically illustrate two modes of stabilizing an impeller within the casing of an MCS. FIG. 12A illustrates stabilization using a passive magnet and hydrodynamic journal bearing force. FIG. 12B illustrates stabilization using passive and active magnets.

FIG. 13A schematically illustrates a block diagram depicting the electrical operation of an electromagnetic stabilization system. FIG. 13B schematically illustrates an example of a circuit that may be used according to the flow chart depicted in FIG. 13A to operate the electromagnetic stabilization system.

FIG. 14A illustrates a top view of the rotor. FIG. 14B illustrates a perspective view of the rotor installed within the impeller of an MCS.

FIG. 15A illustrates a top view of the stator. FIG. 15B illustrates the positioning of the stator around an impeller as well as the relative positioning of the lower axial and radial suspension components.

FIGS. 16A-16F illustrate examples of MCS power systems and operating parameters. FIG. 16A schematically illustrates an example of a transcutaneous energy transfer system. FIG. 16B schematically illustrates an example of a percutaneous energy transfer system. FIG. 16C schematically illustrates an example of motor driving circuit.

FIG. 16D schematically illustrates an example of a battery charging circuit. FIG. 16E schematically illustrates an example of a power conditioning circuit. FIG. 16F depicts computational results of haemolysis simulations relative to other devices.

FIG. 17 schematically illustrates an example of an MCS installed in-series with a portion of the descending aorta in an angled configuration.

FIGS. 18A-18B schematically illustrate examples of an MCS installed in-parallel with a portion of the descending aorta in angled configurations. FIG. 18A shows an MCS installed using straight grafts. FIG. 18B shows an MCS installed using two curved grafts.

FIGS. 21A-21D schematically depicts simulated blood flow through various MCS configurations. FIG. 21A illustrates a MCS installed in an angled configuration with approximately 45 degree inlet and outlet angles relative to the aorta.

FIG. 21B shows a MCS installed in an angled configuration with an approximately 65 degree inlet angle and an approximately 25 degree outlet angle relative to the aorta. FIGS. 21C and 21D show coaxial MCSs with 25 mm and 15 mm inlet radii, respectively, or MCSs installed in angled configurations with an approximately 90 degree inlet angle and an approximately collinear (0 degree) outlet relative to the aorta.

FIG. 22A illustrates a side cross-sectional view of the impeller, a portion of the diffuser, and the direction of fluid flow through the diffuser. FIGS. 22B and 22C illustrate different perspective views of the collinear MCS with wrap-around diffuser and the direction of fluid flow through the MCS.

FIGS. 23A-23E schematically illustrate examples of vanes positioned within the inflow or outflow paths of an MCS for altering fluid flow. FIG. 23A schematically illustrates a side cross-section of an example of an inlet of a device comprising stationary pre-swirl vanes. FIG. 23B schematically illustrates a side view of the opened circumference of another example of an inlet comprising stationary pre-swirl vanes. FIG. 23C schematically illustrates a top cross-sectional view of a casing comprising a splitter vane within the diffuser and volute. FIG. 23D schematically illustrates a top cross-sectional view of a casing comprising a splitter vane within the outlet volute. FIG. 23E schematically illustrates a top cross-sectional view of a casing comprising diffuser vanes circumferentially positioned around the diffuser.

DETAILED DESCRIPTION

Figure 3:
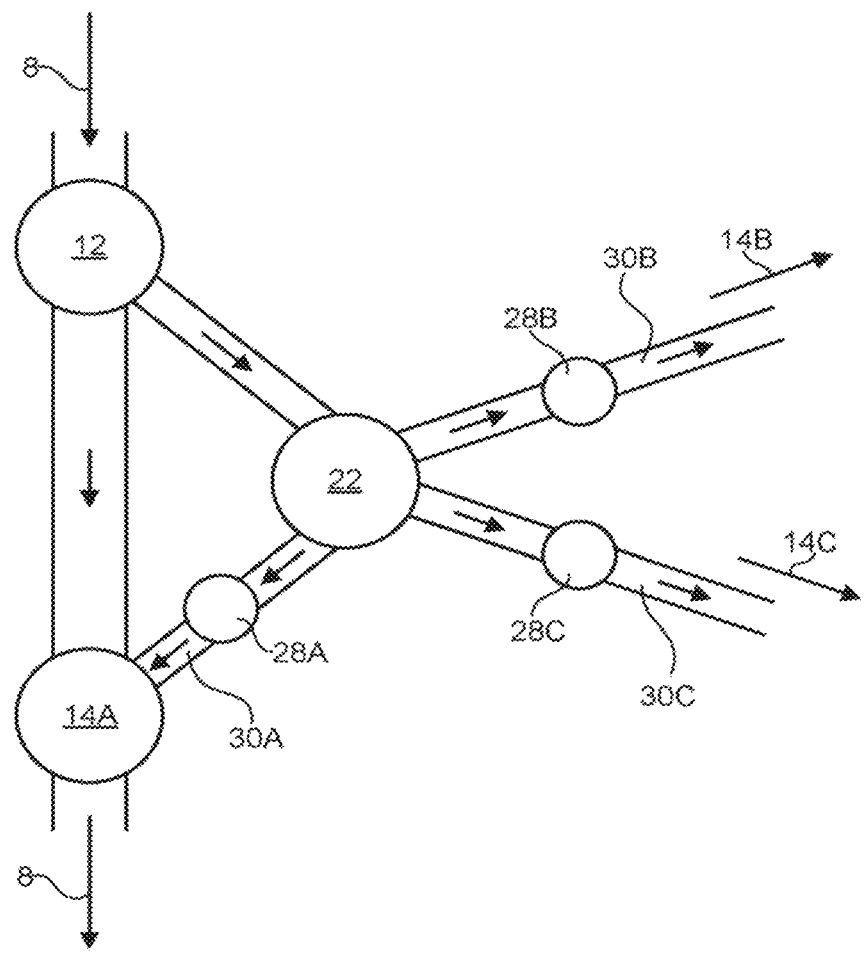
FIG. 3 depicts a mechanical circulatory support comprising multiple outlet ports and impedance setting members.

FIG. 1 depicts a section of vasculature 2. In an embodiment, the section of vasculature 2 comprises a section of the descending aorta. In an embodiment, the section of the descending aorta is below the diaphragm (arrow 4). In an embodiment, the section of the descending aorta is upstream and/or above the renal arteries and/or splanchnic arteries (arrow 6). Blood flow is shown schematically by arrows 8, 8A and 8B.

A mechanical circulatory support 10 comprises connections into (i.e. through the wall of) the vasculature via inlet port 12 and outlet port 14. The inlet port 12 is in fluid communication with a first end 16 of a lumen 20 defined by body portion 24 of the support 10. The outlet port 14 is in fluid communication with a second end 18 of the lumen 20.

A pump 22 is provided within the lumen 20 and configured for driving fluid flow in a direction away from the inlet port 12 and towards the outlet port 14.

In an embodiment, the pump 22 is a centrifugal pump. The geometry of centrifugal pumps appears at first sight to be less convenient than that of axial pumps, which are used in some prior art MCS/VAD devices. However, the inventors have recognised that fluid-flow and turbomachine efficiencies gained from using centrifugal impellers, as opposed to axial impellers, at the selected pressure rise, flow rate, rotational speed, and device diameter, as well as from the less aggressive interaction between the pump and the blood for a given level of pumping more than outweigh any difficulties imposed by the geometry. Levels of pumping that are required in the context of pumping blood can be provided with less input power and less damage to the blood. Operation in-series in the described anatomic location results in lower power levels than devices designed as VADs configured to provide the full 120 mmHg pressure rise, and makes it possible to reduce the dimensions of the pump. Reducing damage to blood reduces the risk of adverse side-effects during use.

In an embodiment, the pump 22 is configured to provide a continuous flow, rather than a pulsatile flow (such as that provided by the native heart). The resulting pump 22 is simpler and can be optimized more easily. The inventors have recognised that it is not necessary to mimic the pulsatile flow of the heart. This is particularly the case when the support 10 is provided in series with the heart because the extent to which the operation of the support disrupts the normal functioning of the heart is reduced in comparison to prior art arrangements that are connected directly to the heart and arranged to operate in parallel with the heart.

In the embodiment shown in FIG. 1, the inlet port 12 is configured to divert a portion 8A of the blood flow within the blood vessel into the lumen 20 while allowing the remaining blood flow 8B to continue through the native blood vessel 2. The outlet port 14 is configured to allow the reintroduction of the diverted portion 8A of the blood flow back into the blood vessel 2 further downstream. In this embodiment, the support 10 therefore operates in parallel with a short portion 26 of the blood vessel 2. This approach minimises disruption to the existing vascular system and can be installed using minimally invasive surgery. In addition, the provision of a region having parallel flow paths increases the overall flow capacity of the vascular system, thereby reducing the load on the heart to a degree. The resistance and impedance of segment 8B may need to be adjusted to prevent recirculating flow between the outlet and the inlet of the pump.

In an embodiment, a device is provided for driving the pump electrically. In an embodiment, the device is configured to be mounted to the body (e.g. having components that are mounted inside the body, outside the body, or both). The support can thus be installed for long periods of time (e.g. multiple weeks, months or years). The patient is thus not required to remain within a hospital ward after the support is installed. In the embodiment shown in FIG. 1, the device for driving the pump comprises a power receiving member 50, which receives power for driving the pump. The power receiving member 50 is configured to receive an input of power 52 from a power source located outside of the body (e.g. a battery mounted on the outside of the body) and/or a power source located inside the body (e.g. a battery mounted inside the body). In an embodiment, the connection between the power source and the power receiving member 50 is made wirelessly, for example using electromagnetic induction. In an embodiment, the power receiving member 50 comprises a coil. Where the wireless connection is made to a power source outside of the body, the connection may be referred to as a transcutaneous connection. In an embodiment, a wired connection is made between a power source located outside the body and the power receiving member 50. In an embodiment, the wired connection is established percutaneously.

In an embodiment, the support 10 further comprises a data transmitter/receiver 54 for transmitting/receiving data 56 to/from a controller 57 outside of the body. In an alternative embodiment, the controller 57, or a part of the controller 57, is configured to be installed within the body (i.e. under the skin). In an embodiment of this type, the controller 57 is sealed in a manner suitable for installation within the body and/or comprises a housing made from a material that is suitable for being in contact with tissue within the body for a prolonged period of time (e.g. a biocompatible material). In an embodiment, the controller 57 comprises a housing made from the same biocompatible material as a housing for an internal power source (e.g. internal batteries) for powering part or all of the support 10.

In an embodiment, the controller 57 is configured to interact with one or more sensors for monitoring one or more operating characteristics of the pump 22. For example, speed sensors can be used to measure the rotational speed of an impeller of the pump 22. In one embodiment three (3) Hall-effect sensors are used to measure impeller rotational speed. Alternatively or additionally, the pressure rise across the impeller is measured, for instance with two pressure transducers, one upstream and one downstream of the impeller. In an embodiment, the flow rate is measured, or calibrated as a function of other measured parameters. In an embodiment the set of measurements output from the sensors, or any subset of the measurements (e.g., impeller rotational speed and pressure rise) are used (for example by the controller 57) to adaptively control the rotational velocity of the impeller and therefore also the power input to the pump motor in order to achieve the required perfusion. In other embodiments, other operational characteristics are adaptively controlled in response to one or more sensor measurements.

In one embodiment, performance data, such as impeller rotational speed and/or pressure rise and/or flow rate is/are transmitted to an internal or external unit (e.g. the controller 57 or a part of the controller 57) that is configured to sound an alarm in case of acute conditions developing, or in case of a system malfunction. In an embodiment, the performance data is transmitted wirelessly to an external unit that collects the data in an application installed in a smartphone or similar device by the patient's bedside, and for example sends them electronically to a monitoring station. In an embodiment, the monitoring station is set up to send an alarm to the patient's guardian or physician, or to emergency services. Alternatively or additionally, the system may be set up to intelligently tune operation of the pump to improve performance. Further details of the electrical operation of the mechanical circulatory support are described elsewhere herein.

FIG. 2 illustrates an alternative embodiment in which the mechanical circulatory support 10 is configured to bypass a portion of the blood vessel 2, rather than operate in parallel with this portion of the blood vessel 2, as in the embodiment of FIG. 1. The inlet port 12 in this embodiment diverts all of the flow 8 within the blood vessel 2 into the lumen 20 of the support 10. Similarly, the outlet port 14 is configured to reintroduce all of the flow 8 back into the native blood vessel 2. Specific examples of mechanical circulatory supports installed either in-series and in-parallel with the aorta will be described herein.

In the embodiments described with reference to FIGS. 1 and 2, the support 10 has a single inlet port 12 and a single outlet port 14. However, this is not essential. In alternative embodiments, the support 10 may comprise two or more inlet ports 12 and/or two or more outlet ports 14. In an embodiment, the support 10 comprises a single inlet port 12 within the descending aorta and two outlet ports 14. In an embodiment, the first outlet port 14 is configured to be connected into the descending aorta and the second outlet port 14 is configured to be connected into the ascending aorta. In an embodiment, the support 10 has a single inlet port 12 connected into the descending aorta and a single outlet port 14 connected into the ascending aorta. Providing an outlet to the ascending aorta may be useful for example to provide additional support to the brain, or to 'prime' the pump. Other configurations are possible according to clinical need.

Where a multiplicity of outlet ports 14 are provided, flow characteristics associated with each of the different outlet ports 14 and/or flow paths leading to the outlet ports 14, may be chosen so as to control the distribution of blood flow provided by the pump 22 according to clinical need. The flow characteristics may include the flow resistance, flow compliance and/or flow inductance. For example, where only a small contribution to the flow is required at a particular outlet port 14, the flow resistance associated with that outlet port 14 may be arranged to be relatively high. Conversely, where a relatively high flow output from the outlet port 14 is required, the flow resistance associated with that outlet port 14 may be arranged to be relatively low. FIG. 3 illustrates, highly schematically, such a configuration. Here, support 10 comprises a single inlet port 12 and three different outlet ports 14A, 14B, 14C. Outlet port 14A is positioned downstream of the inlet port 12 in the same section of vasculature 2. The other outlet ports 14B and 14C are located elsewhere in the vascular system and are not shown in FIG. 3. Flow characteristic setting members 28A, 28B, 28C, which may be valves for example or sections of tubing of controlled diameter, are positioned on respective flow paths between the pump 22 and each of the three outlet ports 14A, 14B, 14C. By varying the flow characteristics using the flow characteristic setting members 28A, 28B, 28C, it is possible to define the proportion of the total flow output by the pump 22 that will be present in the respective flow paths 30A, 30B and 30C.

In an embodiment, the pump is configured to provide a pumping output that is equivalent to or greater than the total pumping requirement of the body within which the support is installed, so that no additional pumping from the native heart is required. In an embodiment, the pump 22, 34 is configured to provide a pressure of at least 125 mmHg and/or flow rates equivalent to the normal cardiac output of 5 litres per minute. The centrifugal pump approach of the present invention allows such pressure and flow rates to be achieved in a compact device with minimum damage to the blood. In another embodiment, the pumping output is lower than the total pumping requirement of the body. In such an embodiment the pump assists the native heart, which must provide a portion of the total pumping power.

Figure 4:
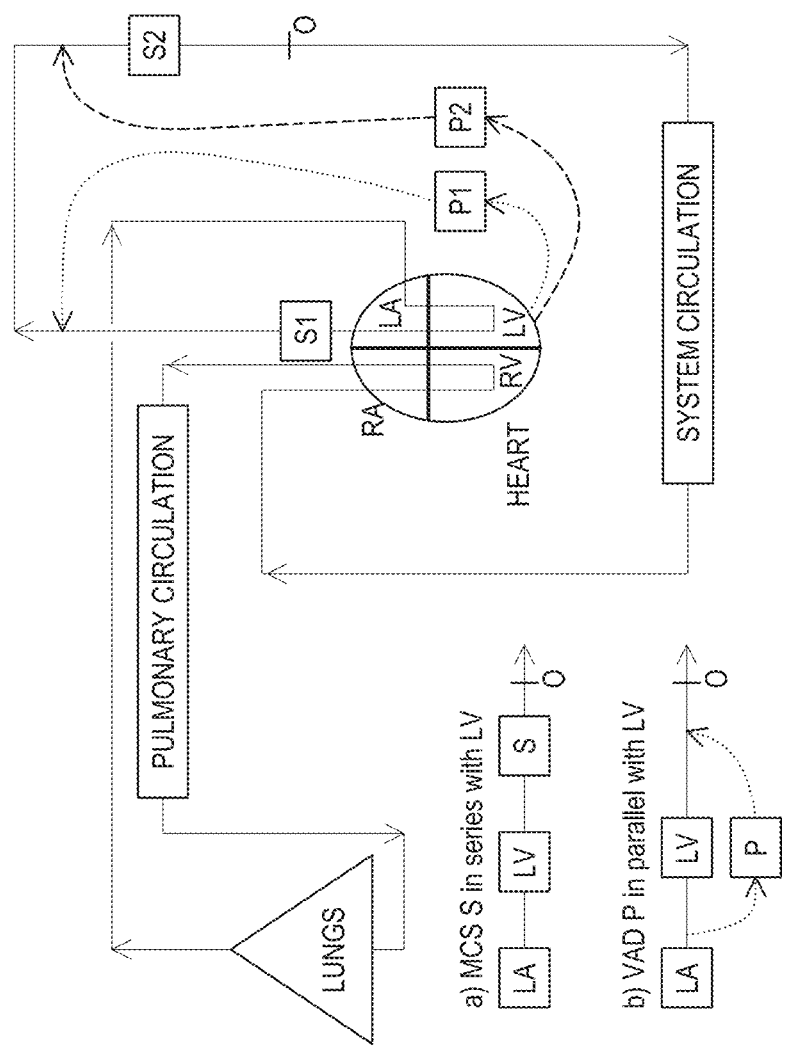
FIG. 4 schematically illustrates various installation configurations of VADs in the vasculature.

FIG. 4 schematically depicts the differences in installation of various devices within the vasculature, including a VAD installed in-parallel with the left ventricle and outflow connected to the ascending aorta (P1), a VAD installed in-parallel with the left ventricle and outflow connected to the descending aorta (P2), an MCS installed in-series with the ascending aorta (S1), and an MCS installed in-series with the descending aorta (S2), where "MCS" and "VAD" are here used to differentiate devices installed in-parallel with the left ventricle and devices installed in-series with the left ventricle, respectively. As discussed elsewhere, each installation configuration may affect the operating requirements and the installation procedure of the VAD. Installation of a VAD in-parallel with the left ventricle competes for blood flow with the native heart and may essentially takeover pumping function. In-parallel installation may disrupt the natural functioning of the heart and may not allow for full regenerative potential of native heart tissue. VADs installed in-parallel may be required to generate the full physiological pressure rise (about 120 mmHg). VADs installed in-parallel generally need to be installed through highly invasive surgery (e.g., sternotomy) which generally require performing a cardiopulmonary bypass, though there have been recent attempts to modify installation of some VADs to less invasive surgeries, such as described in Makdisi, G, Wang, I-W., "Minimally invasive is the future of left ventricular assist device Implantation" (2015) Journal of Thoracic Disease 7(9), E283-E288 (incorporated herein by reference). MCSs installed in-series add to the pressure rise of the native heart, thus unloading the pressure rise required by the diseased native heart and supporting its natural function, allowing for regenerative potential of the heart. Therefore, because of the lower pressure rise requirement by the in-series devices, MCSs designed for in-series installation may have lower power requirements. In-series installation of a MCS, particularly within the descending aorta, may be performed via minimally invasive procedures, without a cardiopulmonary bypass, as the device's flow inlet need not be adjoined directly to the heart. Installation of MCSs with outlets in the ascending aorta may be used to support cerebral blood flow. Installation of MCSs with outlets in the descending aorta may advantageously avoid risks of blood damage from the MCS causing a cerebral thromboembolism or stroke, and they may also increase renal perfusion thus assisting in overcoming cardio-renal syndrome.

Figure 5A:
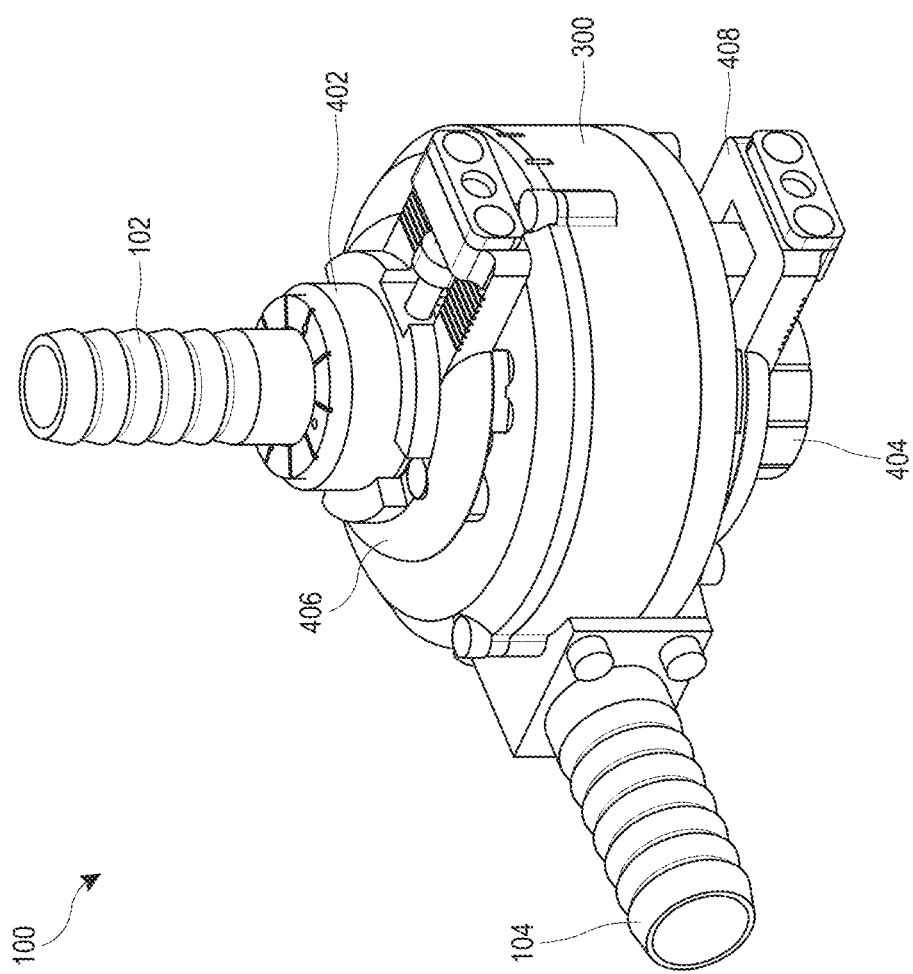
FIGS. 5A-5D illustrate an example of an MCS.
Figure 5B:
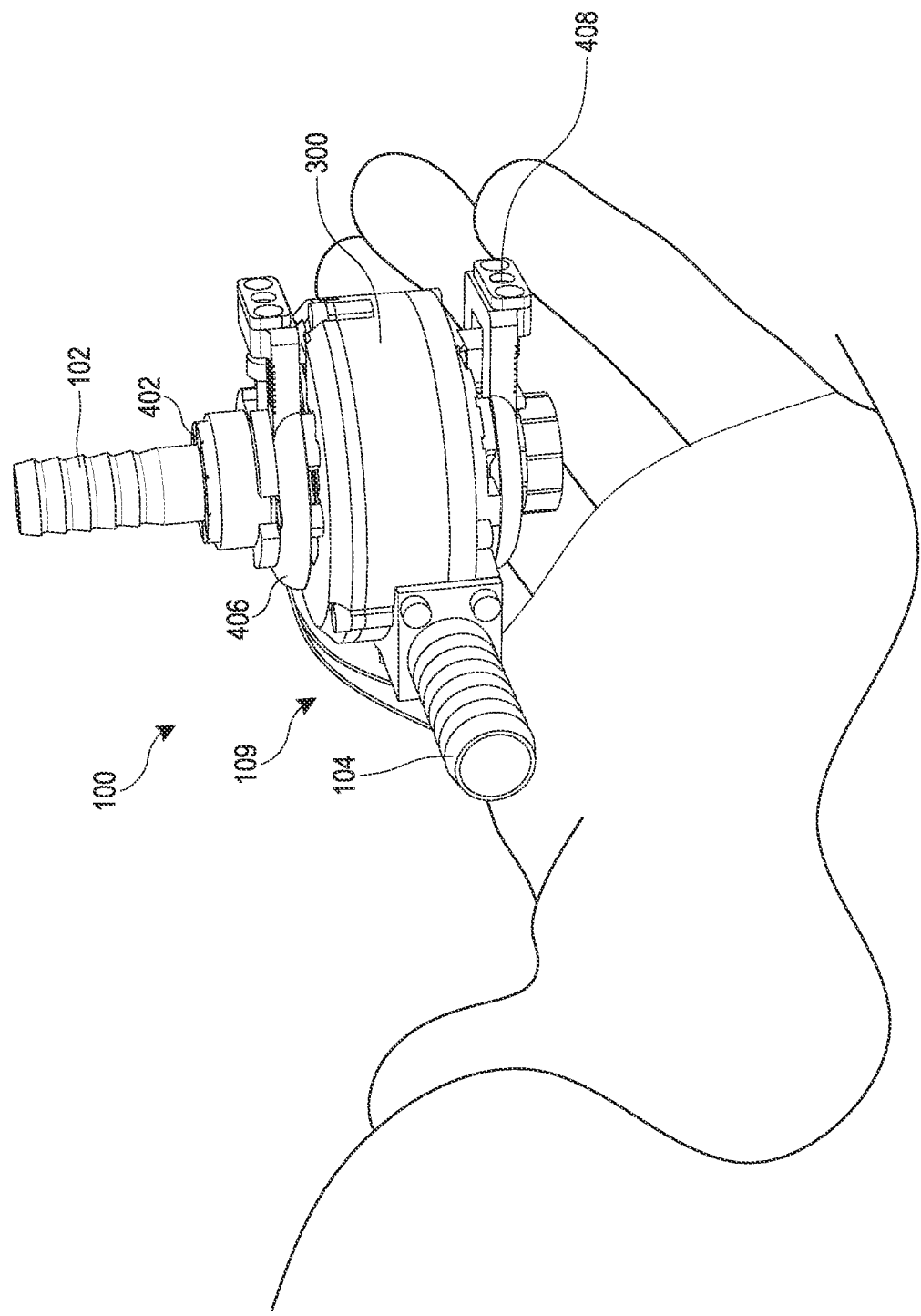
Figure 5C:
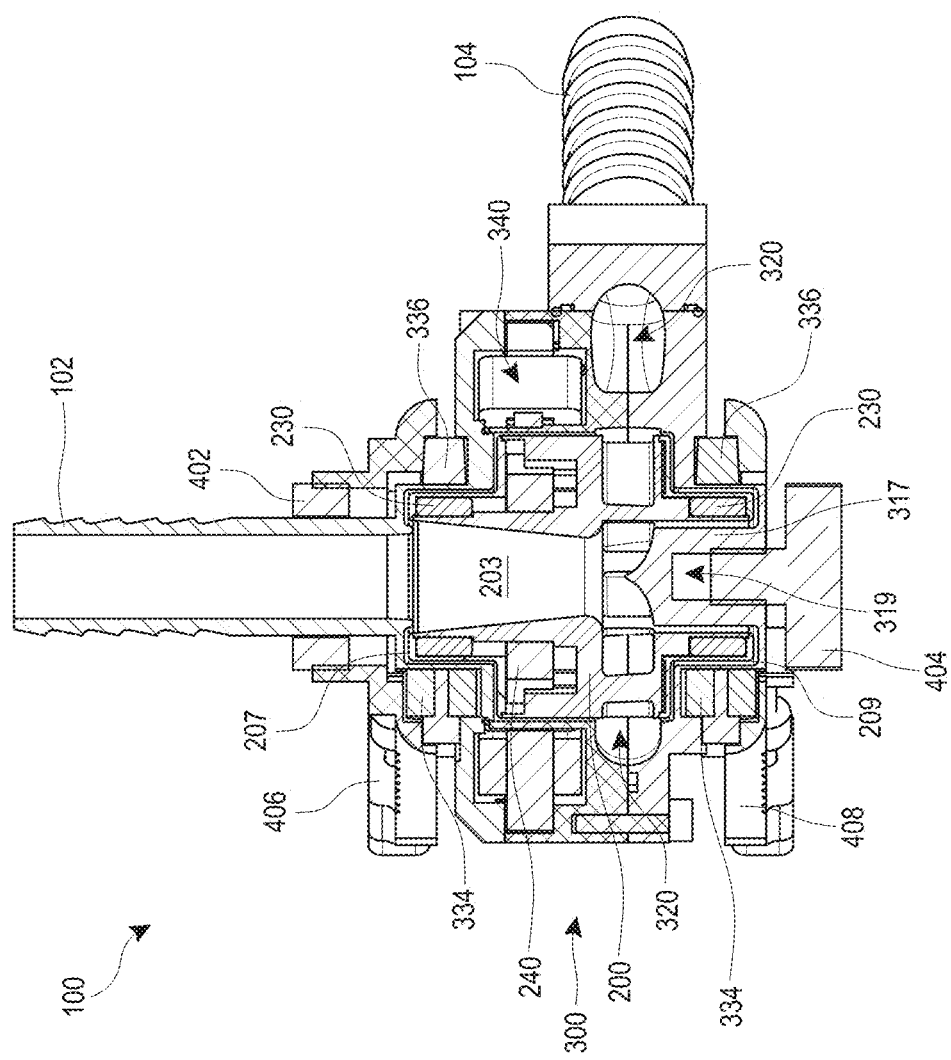
Figure 5D:
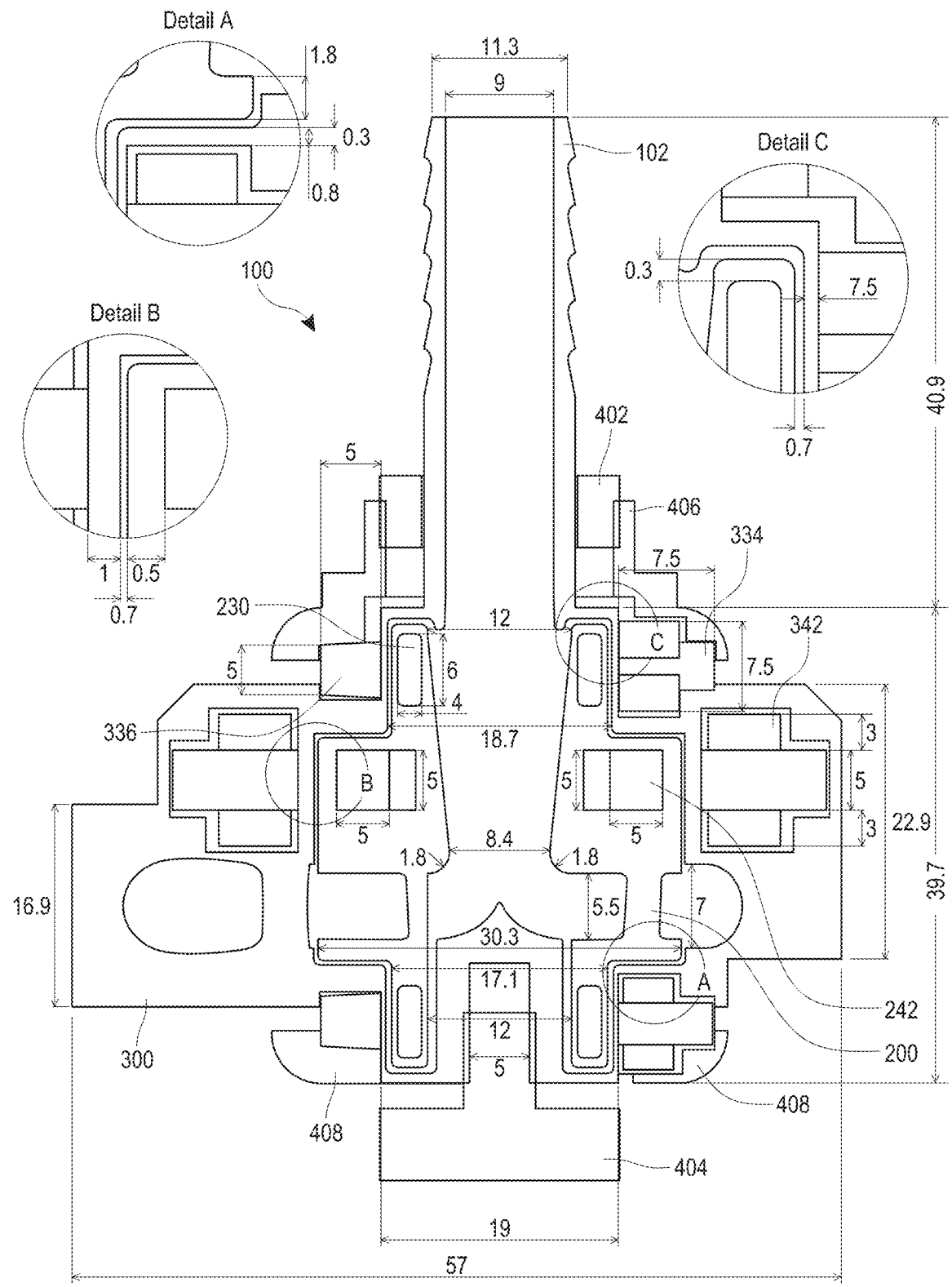

FIGS. 5A-5D illustrate an example of an MCS 100. FIG. 5A illustrates a perspective view of the MCS 100. FIG. 5B shows a photograph of a prototype of the MCS 100, demonstrating the approximate size of the MCS 100 in a person's hand. FIG. 5C illustrates a side cross-section of the MCS 100. FIG. 5D schematically illustrates a simplified side cross-section of the MCS 100 along with example dimensions (in mm) of various components and the overall dimensions of the MCS 100. The MCS 100 may generally comprise an impeller 200, a casing 300, and magnet holders 402, 404, 406, 408. The casing 300 may include an inlet 102 for receiving blood flow into the MCS 100, and an outlet 104 for directing exiting blood flow from the MCS 100, both extending from a main body for housing the impeller 200. The inlet 102 and outlet 104 shown in FIGS. 5A-5D are configured particularly for in-vitro testing, and may be modified accordingly for in-vivo applications (e.g., shortened and/or configured for attachment to vascular grafts). The impeller 200 may be contained entirely within the casing 300 and configured to be magnetically suspended, hydrodynamically suspended, or suspending by a combination of hybrid bearings within the casing 300 such that it does not contact the inner surface of the casing 300. The impeller 200 may be configured to be electromagnetically rotated within the casing 300 in a contactless manner. The impeller 200 may act as a centrifugal pump moving blood received through the inlet 102 from an axial direction and expelling it centrifugally along the circumference of the impeller 200 into the outlet 104. The magnet holders 402, 404, 406, 408 may be coupled to the casing 300 and position magnets and/or electromagnets around the casing 300 and impeller 200, which can be used to electromagnetically suspend and stabilize the impeller 200 within the casing 300. Other magnets, such as those that drive the rotation of the impeller 200, may be positioned within the casing 300. As shown in FIG. 5B, one or more electrical wires 109 may extend from the MCS 100 (e.g., they may extend between a controller described elsewhere herein and the casing 300). The electrical wires may provide power to the device and/or transmit sensor input to the controller. Each of the operative components of the MCS 100 will be described in further detail elsewhere herein.

Figure 6B:
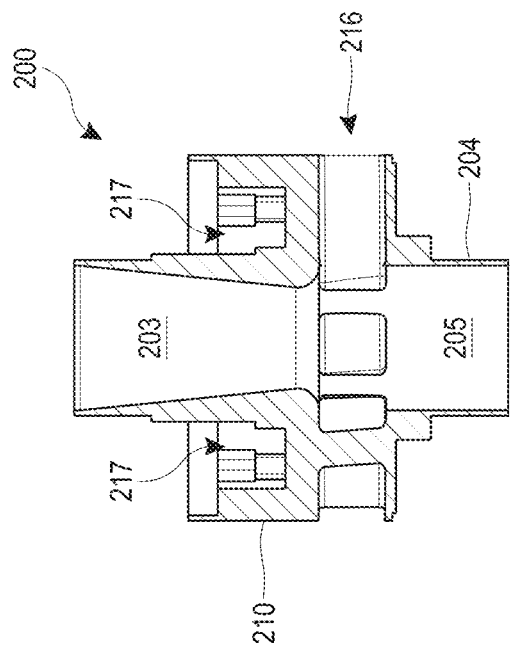
Figure 6C:
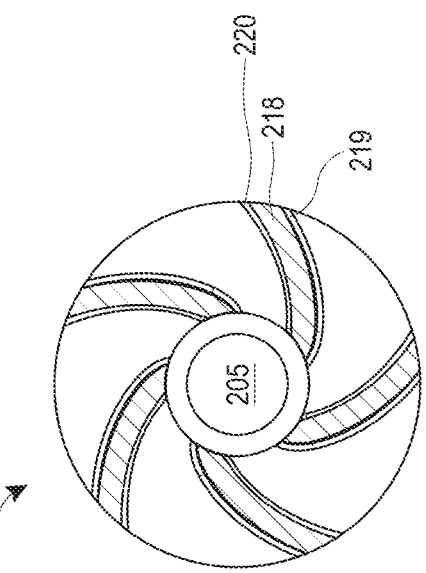
Figure 6A:
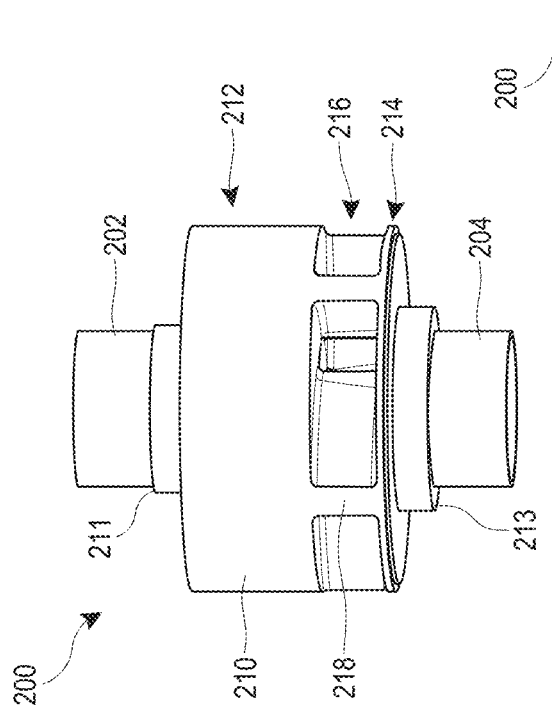

FIGS. 6A-6E illustrate examples of the impeller 200 and impeller assembly 201. FIG. 6A illustrates a perspective view of the impeller 200. FIG. 6B illustrates a side cross section of the impeller 200. FIG. 6C illustrates a top cross section of the impeller 200. FIG. 6D illustrates a perspective view of the impeller assembly 201, comprising the impeller 200, a top cap 207, a bottom cap 209, and other components not visible. FIG. 6E illustrates an exploded view of the impeller assembly 201 depicted in FIG. 6D. The impeller 200 can be configured to be magnetically suspended within the casing 300 such that the impeller 200 is sealed off from the external physiological environment except for blood entering the MCS 100 through the inlet 102. As shown in FIG. 6A, the impeller 200 may comprise a top port 202, a bottom port 204, and a main body 210, each of which may be generally shaped as bodies of revolution (e.g., cylindrical). The main body 210 may have a larger diameter than the top port 202 and/or the bottom port 204. The main body 210 may comprise an upper portion 212 (forming an impeller shroud), a lower portion 214 (forming an impeller hub), a blade passage chamber 216 between the upper portion 212 and lower portion 214, and a plurality of impeller blades 218 positioned within the blade passage chamber 216.

Figure 14B:
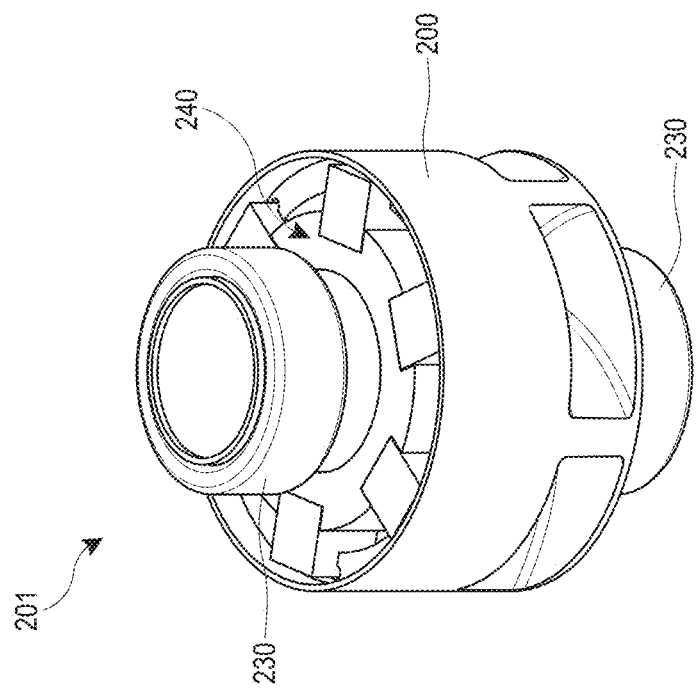
FIGS. 14A-14B illustrate an example of a MCS rotor.

As shown in FIG. 6B, the top surface of the upper portion 212 may be generally open and may extend into an upper chamber 217 configured to receive a rotor 240, described elsewhere herein, as indicated in FIG. 6E. In other embodiments, the lower portion 214 may additionally or alternatively include an open chamber. The outer diameter of the upper chamber 217 may comprise indentations configured to seat and secure magnets of the rotor 240 (FIG. 14B). The upper portion 212 can include an upper channel 203 which may extend from the top surface of the top port 202 to the bottom surface of the upper portion 212 for receiving blood flow into the blade passage chamber 216. The upper channel 203 may comprise generally circular top and bottom openings. The upper channel 203 may be generally cylindrical or frusto-conical in shape, or shaped as a body of revolution to optimize flow patterns at the inlet 102. The edge between the upper channel 203 and the blade passage chamber 216 may be generally rounded or curved for directing blood flow in a radially outward direction. A lower channel 205 may extend from the top surface of the lower portion 214 to the bottom surface of the bottom port 204. The lower channel 205 may comprise generally circular top and bottom openings. The lower channel 205 may be generally cylindrical or frusto-conical in shape. The edge between the lower channel 205 and the blade passage chamber 216 may be slightly rounded to reduce damage to the blood. The upper channel 203 and/or the lower channel 205 may be aligned generally in the center of the upper and lower portions 212, 214. The upper and lower channels 203, 205 may have the same or similar diameters and may be generally aligned with each other in an "axial" direction of the MCS 100, perpendicular to the plane containing the impeller blades 218 and aligned with the direction blood flow is received by the impeller 200.

The bottom surface of the upper portion 212 may form a ceiling to the blade passage chamber 216 and the top surface of the lower portion 214 may form a floor to the blade passage chamber 216. The impeller blades 218 may extend from the ceiling of the blade passage chamber 216 to the floor of the blade passage chamber 216 (i.e. between the impeller shroud and the impeller hub). The blades 218 may be integral with the upper portion 212 and the lower portion 214 and may be formed by machining a monolithic piece of material. The impeller 200 shown in FIGS. 6A-6E is an example of a shrouded impeller, as the blades 218 are covered on the top and bottom by the upper portion 212 and the lower portion 214 such that fluid may not flow over or under the blades 218. In other embodiments, unshrouded impellers may be used as described elsewhere herein. The impeller blades 218 may be generally perpendicular to the ceiling and the floor of the blade passage chamber 216 and may form a plane perpendicular to the axial direction of incoming blood flow (the axial direction of the MCS) in order to facilitate manufacturing considerations. In other configurations the impeller blades 218 may be three-dimensional bodies with lean from the axial direction between the hub and tip (where the blade meets the shroud), in order to optimize flow parameters. Three-dimensionally shaped blades 218 may be made with advanced manufacturing techniques such as investment casting or three-dimensional printing of the biocompatible impeller material. As shown in FIG. 6C, the blades 218 may each comprise a pressure-side 219 and a suction-side 220. The blades 218 may extend in a generally radial or meridional direction from an inner diameter (the leading edge of the blade) to an outer diameter (the trailing edge of the blade). In some embodiments, the blades 218 may be somewhat curved. The pressure-side 219 may be convex and the suction-side 220 may be concave, particularly near the tip of the blade. The inner diameter (leading edge) of the blades 218 may be aligned with the upper channel 203 and/or the lower channel 205. The outer diameter (trailing edge) of the blades 218 may be aligned with the outer diameter of the main body 210. In some embodiments, the upper portion 212 and the lower portion 214 may have different diameters and the blades 218 may extend to the larger diameter of the two diameters. The blades 218 may be of a generally uniform thickness as they extend from their leading edge to their trailing edge. In other embodiments, and particularly with advanced manufacturing methods employed, the blades 218 may be shaped as in modern centrifugal compressors and radial-inflow turbines of modern turbochargers. The edge of the blades along the inner diameter (the leading edge) and/or outer diameter (the trailing edge) may be shaped (e.g., rounded) to match the radius of curvature of the inner circumference or outer circumference, respectively, of the impeller main body 210 (the shroud and/or the hub) to which the blades 218 may be aligned. The shapes of the blades 218 along the meridional direction may be shaped with advanced turbomachinery blade-design methods, such as described by T. Korakianitis, I. Hamakhan, M. A. Rezaienia, A. P. S. Wheeler, E. Avital and J. J. R. Williams, "Design of high-efficiency turbomachinery blades for energy conversion devices with the three dimensional prescribed surface curvature distribution blade design (CIRCLE) method" Applied Energy, Vol 89, No. 1, pp. ~215-227, January 2012. (hereby incorporated by reference). Each of the plurality of blades 218 may be of identical shape and configuration to the other. The blades 218 may be spaced uniformly around the circumference of the main body 210. The impeller 200 may include any number of blades 218 (e.g., three, four, five, six, seven, eight, nine, etc.). Blood flow may be directed from the inlet 102 to the blade passage chamber 216 and pumped in a centrifugal direction between the blades 218 and out the open circumference portions of the blade passage chamber 216.

FIGS. 6D and 6E illustrate the shrouded impeller assembly 201 in assembled and exploded views, respectively. The top port 202 and bottom port 204 may have the same or similar diameters. The top port 202 and/or the bottom port 204 may comprise shapes in bodies of revolution. The top port 202 and/or the bottom port 204 may comprise shoulders 211, 213 (shown in FIG. 6A) upon which a ring magnet 230 may be seated or partially seated, as indicated in FIG. 6E. The ring magnets 230, described elsewhere herein, may be configured to slide over the top port 202 and/or bottom port 204. In some embodiments, the ring magnets 230 may form a tight interference fit with the impeller 200, may be attached with advanced joining techniques, or may be fully-inserted into the impeller material. A rotor 240, described elsewhere herein, may be configured to be received within the impeller 200. The impeller assembly 201 may further comprise a top cap 207 and/or a bottom cap 209. The top cap 207 and bottom cap 209 may be generally shaped as bodies of revolution (e.g., tubular). The caps 207, 209 may comprise flat annular rims extending radially outward at one end configured to be seated against and coupled with the top and bottom surfaces of the main body 210, respectively. The caps 207, 209 may have thin annular rims extending radially inward at the other ends configured to be seated over the edges of the top port 202 and bottom port 204, respectively. The top cap 207 may be configured to receive the upper port 202 and/or the bottom cap 209 may be configured to receive the bottom port 204 within inner diameters of their bodies. The top cap 207 and/or bottom cap 209 may be configured to sit over top of the ring magnets 230 and to seal them off from the external environment, such as the casing 300. The radially outward rim of the top cap 207 may be configured to seal the upper chamber 217 and close off the rotor 240 from the external environment, such as the casing 300. In other embodiments, the rotor 240 may be positioned in a lower chamber, as described elsewhere herein, or an additional rotor may be positioned in a lower chamber. The top cap 202 and/or bottom cap 204 may be coupled to the main body 210 by any suitable means, including laser welding or a biocompatible adhesive. In some embodiments, the top cap 207 is contour laser welded to the impeller 200 and the bottom cap 209 is contour laser welded to the impeller 200. The impeller assembly may comprise an axial target 221, which may comprise a flat annular right. The axial target 221 may be seated on the bottom surface of the lower portion 214 of the impeller 200. The axial target 221 may be fabricated from stainless steel or other suitable materials. The axial target may be magnetic. The impeller 200, top cap 207, and bottom cap 209 may comprise a biocompatible material, such as polyether ether ketone (PEEK), for example PEEK OPTIMA, biocompatible titanium, and/or biocompatible titanium coated with biocompatible alloys, because they comprise blood-contacting surfaces.

FIGS. 7A and 7B depict alternative embodiments of impellers 250, 252 which exclude top ports and bottom ports. In some implementations, these impellers 250, 252 may be subsequently joined to upper and lower ports after fabrication. As shown in FIGS. 7A and 7B the impellers 250, 252 may comprise upper and lower portions 212, 214 of approximately the same axial length. In some embodiments, as seen in FIG. 7B, the leading edges of the blades 218 of impeller 252 may be rounded off. In some embodiments, as seen in FIG. 7B, the leading edges of the blades 218 may extend inward of the bottom opening of the upper channel 203. This configuration may allow for easier machining of the leading edges of the blades 218 from the top. Embodiments in which the leading edges of the blades 218 are aligned with the bottom opening of the upper channel 203, as seen in FIG. 6C, may cause less disruption to the incoming blood flow.

In some embodiments, the impeller may be an unshrouded impeller, as opposed to the shrouded impeller 200 described above. FIG. 7C illustrates an example of an unshrouded impeller 254 with blades 255 that are uncovered on the top and FIG. 7D illustrates an example of another unshrouded impeller 256 with blades 257 that are uncovered on the top. Shrouded impellers have a top (a shroud) and a bottom (a hub) surrounding the impeller blades 218. Unshrouded impellers are uncovered on one or both sides (top and bottom) of the blades. Fluid may flow over the tip of the blades 255, 257 in the unshrouded impellers 254, 256 illustrated in FIGS. 7C and 7D. Shrouded impellers may have higher efficiencies than unshrouded impellers, due to tip leakage in unshrouded impellers (i.e. the flow leaks over the rotating blades). Shrouded impellers introduce more shear to the blood in the region between the shroud and the casing. The MCS may be modified to support an unshrouded impeller (e.g., with an overhung impeller design). For instance, the motor, comprising the rotor and stator, may be axially positioned around the hub of the unshrouded impeller, rather than around a shroud, and the radial and/or axial stabilization systems (bearings) may also be adjusted appropriately to account for the absence of a shroud. For instance, the impeller may be stabilized using the bottom radial and axial stabilization system components of the impeller along with the stabilization components of the casing, described elsewhere herein.

Figure 8B:
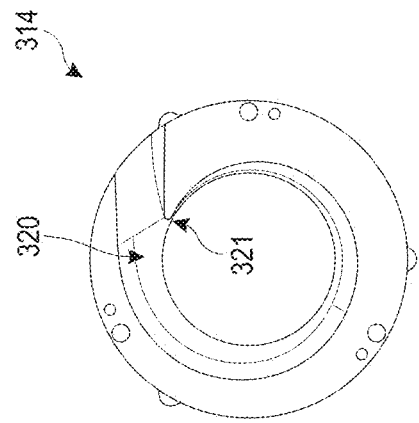
FIGS. 8A-8E illustrate examples of an MCS casing.
Figure 8D:
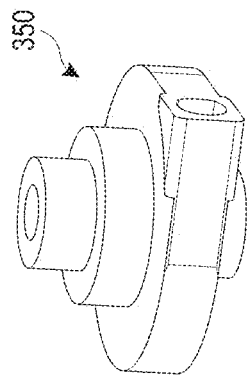
Figure 8A:
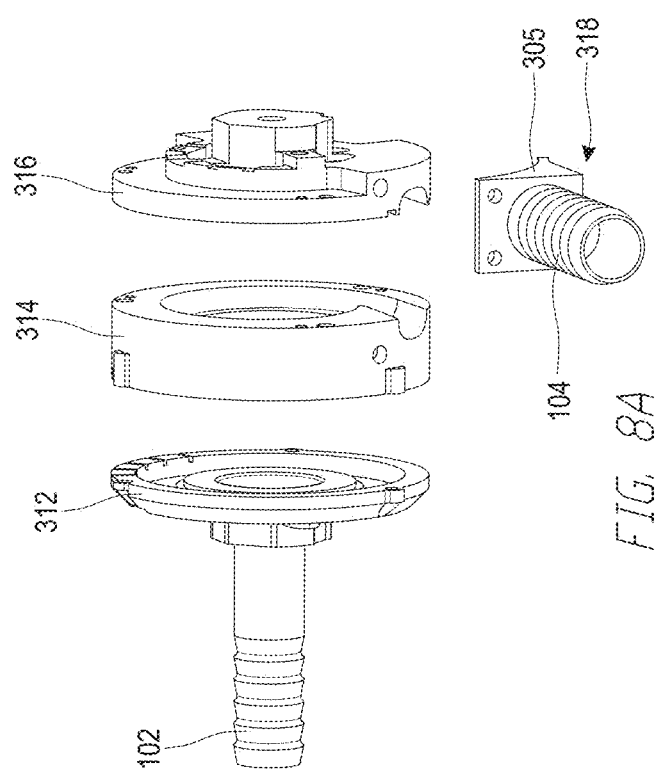

FIGS. 8A-8E illustrate examples of a casing or components thereof. The casing 300 may be configured in shape and dimension to surround the impeller 200 in such a manner that the impeller 200 may be suspended within the casing 300 and rotated around the axial direction of the MCS 100 without any portion of the impeller 200 coming into contact with the casing 300. The blood contacting surfaces, including casing 300 and the impeller 200, may comprise one or more biocompatible materials, including but not limited to polyether ether ketone (PEEK), for example PEEK OPTIMA, biocompatible titanium, and/or biocompatible titanium coated with biocompatible alloys. The casing 300 may comprise multiple components which can be assembled around the impeller 200. For example, FIG. 8A illustrates an exploded view of an example of the casing 300. The casing may comprise a lid 312, an upper volute 314, a lower volute 316, and an outlet attachment 318. The outlet attachment 318 may be particularly suitable for in-vitro testing and may be removed or modified for in-vivo applications, as described elsewhere herein. The lid 312 may include the inlet 102 or may be joinable to the inlet 102. The outlet attachment 318 can include the outlet 104 and may include a curved section 305 for coupling to the outer circumference of the upper volute 314 and/or lower volute 316. The components of the casing 300 may be assembled using screws and/or pins, biocompatible adhesives, or any other suitable means.

Figure 8C:
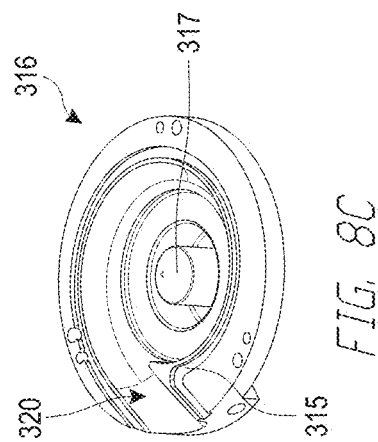

FIG. 8B illustrates a bottom view of the upper volute 314 shown in FIG. 8A, and FIG. 8C illustrates a perspective view of the lower volute 316 shown in FIG. 8A. The casing 300 can include a diffuser 320. The diffuser 320 may comprise a passage for receiving blood pumped by the impeller 200 and may extend into a volute passage in the outlet 104. The diffuser 320 can be formed directly in the internal surface of the casing 300, as shown in FIGS. 8A-8C. The diffuser 320 may be formed across the interface of the upper volute 314 and the lower volute 316. For instance, approximately half the cross-sectional circumference of the diffuser 320 may be formed in the upper volute 314 and approximately half of the circumference may be formed in the lower volute 316. The upper volute 314 and/or the lower volute 316 may include an indentation 315 for receiving a fluid sealing member, similar to an O-ring, shaped to match the circumference of the diffuser 320. A portion of the diffuser 320 circumference may be open to the internal diameter such that blood pumped through the impeller 200 may enter the channel. In other embodiments, the diffuser 320 may be formed by the addition of a component, such as a scroll, along the outer surface of the casing 300, as described elsewhere herein. The diffuser 320 may comprise a partially circular cross-section. The diffuser 320 may extend along the circumferential direction of the MCS 100 to the outlet 104. In some embodiments, the diffuser 320 may simultaneously extend in an axial direction downward, such that the diffuser 320 begins to spiral. The diffuser 320 may extend around the entire circumference of the casing 300 or only a portion of the circumference. In embodiments in which the diffuser 320 extends around more than a full circumference, the diffuser 320 may wrap behind itself closer to the outlet forming an entirely closed cross-section, as seen in Figured 8A-8C. In some embodiments, the size of the cross-section of the diffuser 320 may increase as the channel extends toward the outlet 104. For example, as best seen in FIG. 8B, the radial width of the diffuser 320 may continuously increase from an origin point 321 to the outlet 104. The origin point 321 may have a very small thickness such that it forms the beginning of the channel which expands in the direction of impeller 200 rotation. In some embodiments, the width of the diffuser 320 may expand along a clockwise or counter-clockwise direction when viewed from the top. The direction of fluid flow within the diffuser is set by the direction of impeller rotation and blade lean from the radial direction. In some embodiments, the flow-area distribution along diffuser 320 may be chosen to optimize vortex formation in the outlet 104 blood flow. The optimized vortex formation may emulate the weak passage vortex in the healthy native descending aorta, as described elsewhere herein.

Figure 8E:
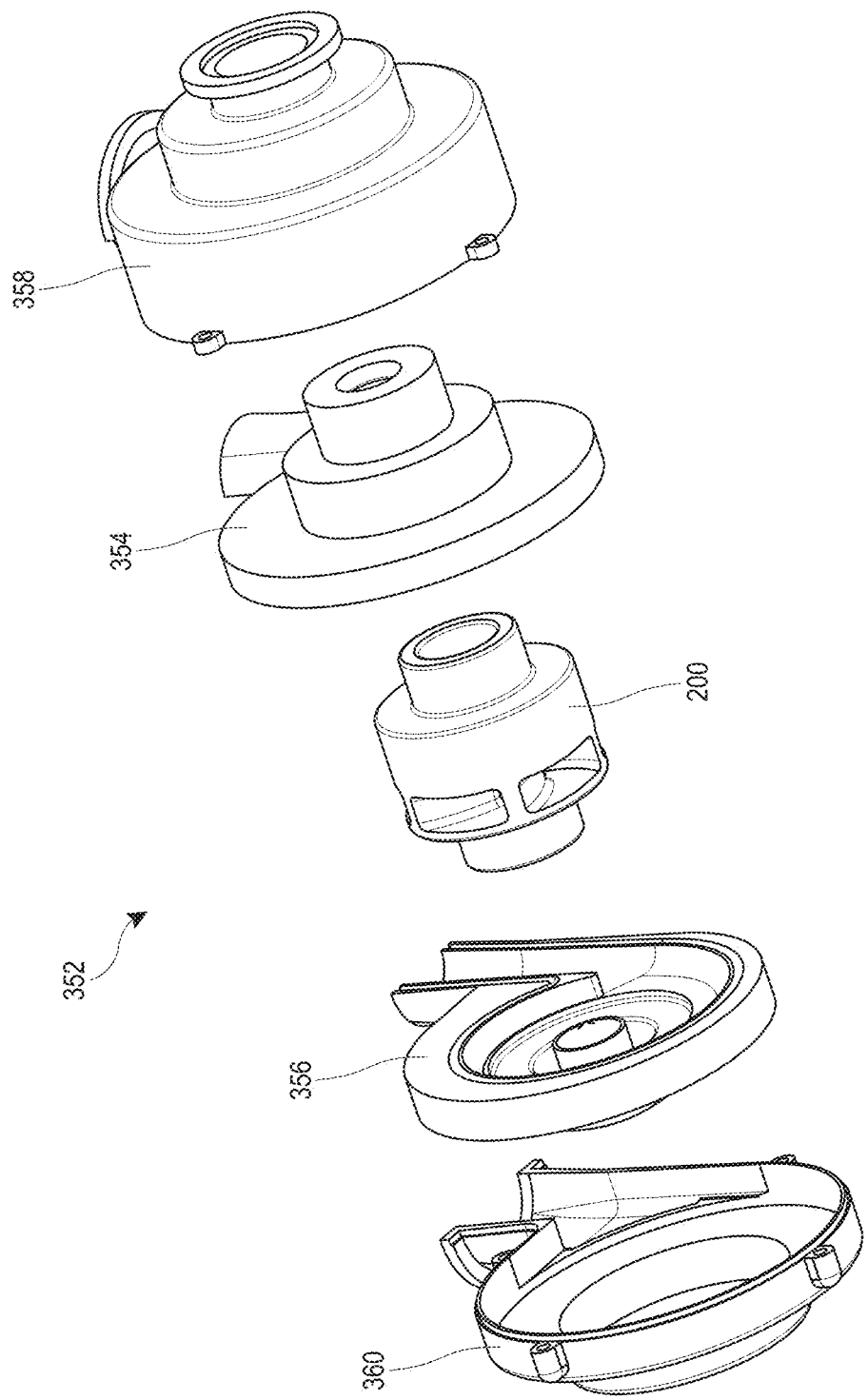

In various embodiments, the outlet 104 is configured to extend perpendicular to the axial direction of the MCS 100, as shown in FIGS. 5A-5D and 8A. The outlet attachment 318 may comprise a volute that forms a continuation of the diffuser 320. The outlet attachment 318 may form a substantially straight channel. The outlet attachment 318 may provide a convenient means for attaching an outlet graft which can be anastomosed to the aorta. In some embodiments, the outlet attachment 318 may be excluded. FIG. 8D illustrates a perspective view of another example of a casing 350 in which the outlet is integral with or contiguous with the main body such that it does not form a cylindrical shaft. In some embodiments, the MCS may comprise multiple layers of casing. FIG. 8E illustrates an exploded view of another example of a casing 352 comprising an inner upper volute 354 and inner lower volute 356, similar to upper volute 314 and lower volute 316, respectively, as well as an outer upper casing 358 and an outer lower casing 360 which are configured to surround the inner casing 354, 356 and to interface with each other along a circumferential seam. In some embodiments, the diffuser 320 may extend into a volute of a scroll ending at the outlet 104, as described elsewhere herein. The scroll may further reorient fluid flow, such as by reorienting the fluid flow into a downward axial direction, such that the MCS may be configured for collinear installation within the aorta.

Figure 9:
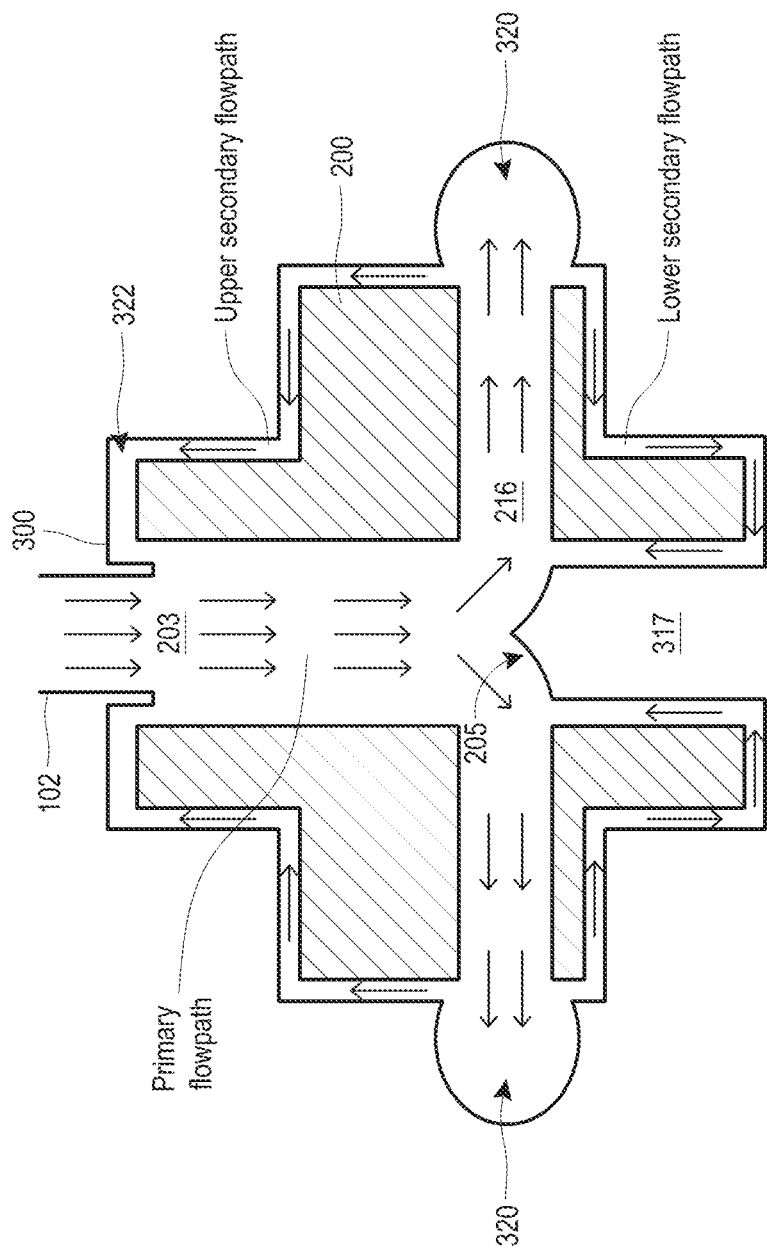
FIG. 9 schematically illustrates an example of blood flow through the impeller and internal casing surface of an MCS.

FIG. 9 schematically illustrates in simplified cross-section the suspended positioning of the impeller 200 within the inner surface of the casing 300 and the flow of blood through those components. The casing 300 forms a small peripheral space 322 around most portions of the impeller 200, excluding the inlet 102 and diffuser 320, each of which forms larger spaces continuous with the primary flow path through the impeller 200. The peripheral space 322 allows for contactless rotation of the impeller 200 by electromagnetic and/or hydrodynamic forces and forms secondary flow paths for blood that fills the peripheral space 322 during operation. The impeller 200 and casing 300 form a primary blood flow path, schematically depicted by arrows, from the inlet 102 to the diffuser 320 leading to the outlet 104 (not shown). Blood can enter the impeller 200 in an axial direction through the upper channel 203 and progress through the rotating passages between the impeller blades 218 which accelerate the blood flow in a tangential and radially outward direction. The blood is forced through the blade passage chamber 216 (between the blades 218 which are not shown), past the outer circumference of the impeller 200, and into the diffuser 320 formed in the inner surface of the casing 300. The impeller 200 increases the velocity and stagnation pressure of the blood as it passes through. The diffuser 320 decelerates the blood flow and increases the static pressure. In some implementations, less than half of a generally circular cross-section defining the diffuser 320 passage may be open to the internal casing volume containing the impeller 200, as seen in FIG. 9. In other embodiments, half or more than half the generally circular cross-section may be open. Although the cross-sections of the diffuser 320 on the right and left side of FIG. 9 are shown as equal in size, the cross-sections may be of dissimilar size as the diffuser passage 320 can increase in cross-sectional area as it extends downstream to the outlet 104.

Blood may also flow through secondary blood flow paths, also schematically depicted by arrows, formed via the peripheral space 322 between the impeller 200 and the casing 300, as shown in FIG. 9. The secondary blood flow paths may include an upper secondary blood flow path and a lower secondary blood flow path. The secondary blood flow paths may originate in the peripheral space 322 between the blade passage chamber 216 of the impeller 200 and the casing 300, by flowing upward or downward between the impeller 200 and the casing 300 rather than into the diffuser 320. Blood caught in between the impeller 200 and the casing 300 within the peripheral space 322 provides a hydrodynamic journal bearing force which helps prevent contact between the impeller 200 and casing 300. In an alternative embodiment, the top and bottom flat surfaces of the impeller assembly 201 have spiral grooves, which become part of the secondary flow area in the device gaps, and assist the hydrodynamic flow through the narrow gaps in order to minimize blood trauma within secondary flow paths. Blood may be forced along these paths either back to the junction of the inlet 102 and the impeller 200 or to the blade passage chamber 216 through the lower channel 205.

The lower volute 316 may include a main stationary shaft 317 (also shown in FIG. 8C) configured to extend from the bottom of the casing 300 into the lower channel 205 of the impeller 200. The main stationary shaft 317 can be cylindrical or slightly conical in shape, with a corresponding variation in the shape of the lower channel 205 with which shaft 317 forms a hydrodynamic journal bearing. The main stationary shaft 317 may be configured to reside within the lower channel 205 such that the impeller 200 can rotate around the shaft 317 in a contactless manner. The upper end of the main stationary shaft 317 may comprise an apex. The upper end of the main stationary shaft 317 may be shaped to direct flow toward the circumference of the blade passage chamber 216. The upper end of the main stationary shaft 317 may be flat, conical, conical with concave surfaces (as shown in FIG. 9), domed, bullet-shaped, rounded, or other suitable shapes. The dimensions of the main stationary shaft 317 may be configured to prevent substantial flow in these clearance (gap) areas of the peripheral space 322 rather than along the primary flow path. The presence of the lower channel 205 allows blood along the secondary flow path to return to the impeller 200 so that it does not sit stagnant in the residual space around the lower portion 214 of the impeller 200, thereby enhancing washout of the MCS 100. The axial position of the impeller may affect the geometry of the flow paths and therefore the flow rates.

The impeller 200 can be magnetically suspended in the axial direction via passive (i.e. permanent) magnets positioned within the impeller 200 and casing 300. FIGS. 10A-10D illustrate examples of the MCS 100 components used to axially suspend the impeller 200. The impeller assembly 201 can include two magnets or two sets of magnets positioned at upper and lower ends of the impeller 200. The casing 300 can include two magnets or two sets of magnets positioned at upper and lower ends of the casing 300. The impeller 200 can be suspended using the magnets to create either approximately equal attractive forces between the impeller 200 and the casing 300 at the upper and lower ends of the MCS 100 or approximately equal repulsive forces between the impeller 200 and the casing 300 at the upper and lower ends of the MCS 100, accounting for other possible forces such as gravity or accelerations from the patient's motions. FIG. 10A illustrates an example configuration of passive magnets for axial suspension of the MCS 100. The impeller assembly 201 may comprise two ring magnets 230 which can be configured to be seated around the top port 202 and bottom port 204 (not shown) of the impeller 200. The MCS 100 may comprise sets of axial-suspension magnets 330 positioned outside the impeller 200. The axial-suspension magnets 330 may be positioned within the casing 300, coupled to the casing 300, and/or positioned between the casing 300 and other components external to the impeller 200, such that the axial-suspension magnets 330 remain stationary relative to the housing 300 and physically uncoupled from the impeller 200. There may be one or more axial-suspension magnets 330 positioned uniformly around the upper and lower circumference of the casing 300. For instance, there may be four axial-suspension magnets 330 positioned axially above the upper ring magnet 230 and four axial-suspension magnets 330 positioned axially below the lower ring magnet 230, as shown in FIG. 10A. In other embodiments, the axial-suspension magnets 330 may be ring magnets similar to ring magnets 230. In an alternative embodiment, the axial suspension magnets may be positioned slightly further apart in the axial direction, and by activation via electromagnets coupled to the casing, as described elsewhere herein, be used to axially oscillate the impeller assembly 201 in the casing 300, thus providing pulsatile flow at impeller outlet.

Figure 10C:
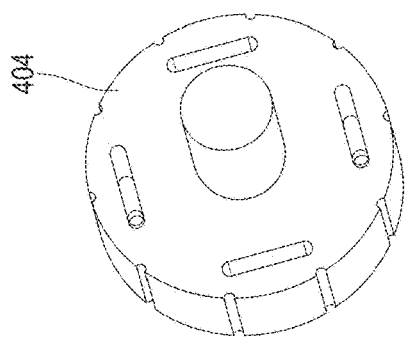
FIGS. 10A-10D illustrate example components of an MCS magnetic axial suspension system.
Figure 10B:
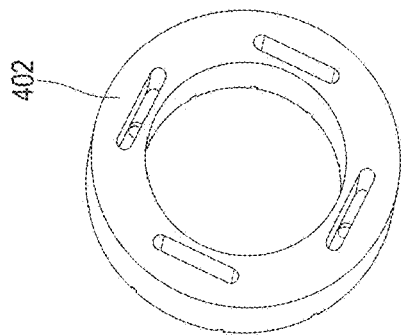

The upper axial-suspension magnets 330 may be positioned within an upper axial magnet holder 402, such as that shown in FIG. 10B, and/or the lower axial-suspension magnets 330 may be positioned within a lower axial magnet holder 404, such as that shown in FIG. 10C. The axial magnet holders 402, 404 may comprise slots for receiving each of the axial-suspension magnets 330. The axial-suspension magnets 330 may be coupled to the axial magnet holder 402, 404 via interference fit or other suitable means, such as adhesives, screws, pins, etc. In some embodiments, the upper axial magnet holder 402 may comprise a ring shape configured to fit over the inlet 102, as shown in FIGS. 5A-5D. The upper axial magnet holder 402 may be secured to the inlet 102 by a friction fit. The upper axial magnet holder 402 may be slidable along the length of the inlet 102 under sufficient force. The lower axial magnet holder 404 may be configured as a plate with a central post. The plate may be generally circular. The post may be generally cylindrical. The post may be configured to be received within a channel 319 formed generally in the center of the bottom outer surface of the casing 300 (e.g., the lower volute 316), as depicted in FIGS. 5C and 5D. The length of the channel 319 may extend into the main stationary shaft 317. The lower axial magnet holder 404 may be secured to the casing 300 by a friction fit. The lower axial magnet holder 404 may be translatable within the channel 319 under sufficient force.

Figure 10D:
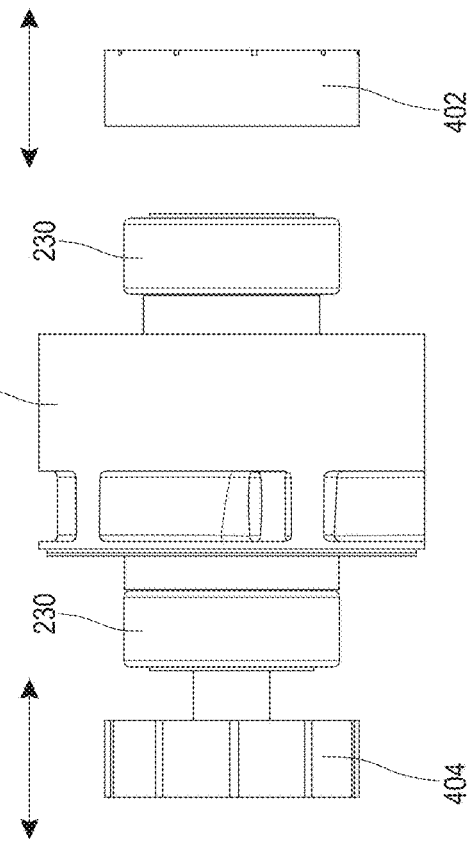
Figure 10A:
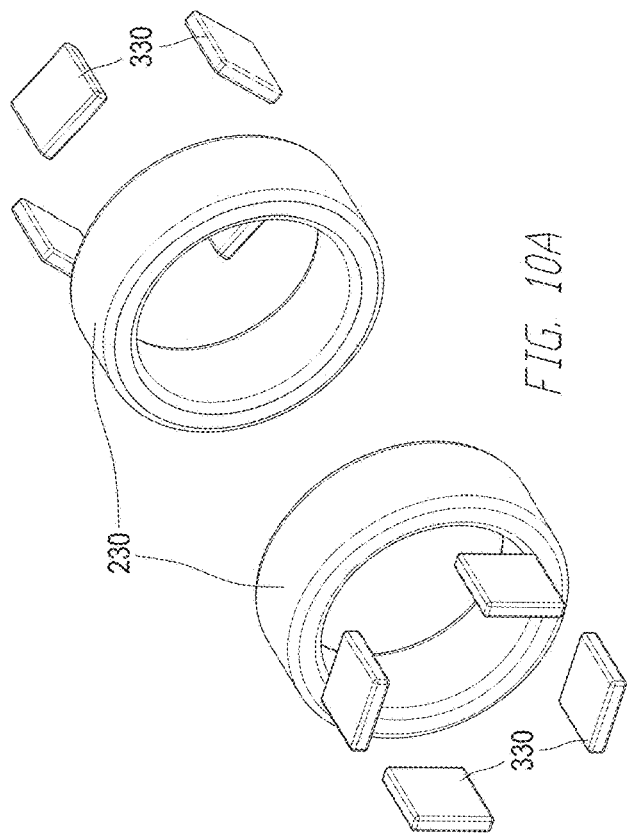

FIG. 10D illustrates the ring magnets 300 coupled to the impeller 200 and schematically illustrates the positioning of the upper axial magnet holder 402 and the lower axial magnet holder 404 relative to the impeller 200. In some embodiments, the ring magnets 230 may be of a first polarity (e.g., positive or negative). The axial-suspension magnets 330 may be of a second polarity, opposite the first polarity, such that the upper ring magnet 230 is pulled axially upward toward the upper set of axial-suspension magnets 330 and the lower ring magnet 230 is pulled axially downward toward the lower set of axial-suspension magnets 330. In other embodiments, the bottom ring magnet 230 and bottom set of axial-suspension magnets 330 are of a first polarity and the upper ring magnet 230 and the upper set of axial-suspension magnets 330 are of a second polarity, such that the upper ring magnet 230 is pushed axially downward and the lower ring magnet 230 is pushed axially upward. The axial-suspension magnets 330 may be adjustable. For example, as schematically illustrated by the arrows in FIG. 10D, the magnets 330 may be translatable in an axial direction to modulate the magnetic force and optimize the axial suspension, as described elsewhere. Positioning the axial-suspension magnets 330 within the upper axial magnet holder 402 and lower axial magnet holder 404 provides for easy axial adjustability relative to the casing 300.

Figure 11E:
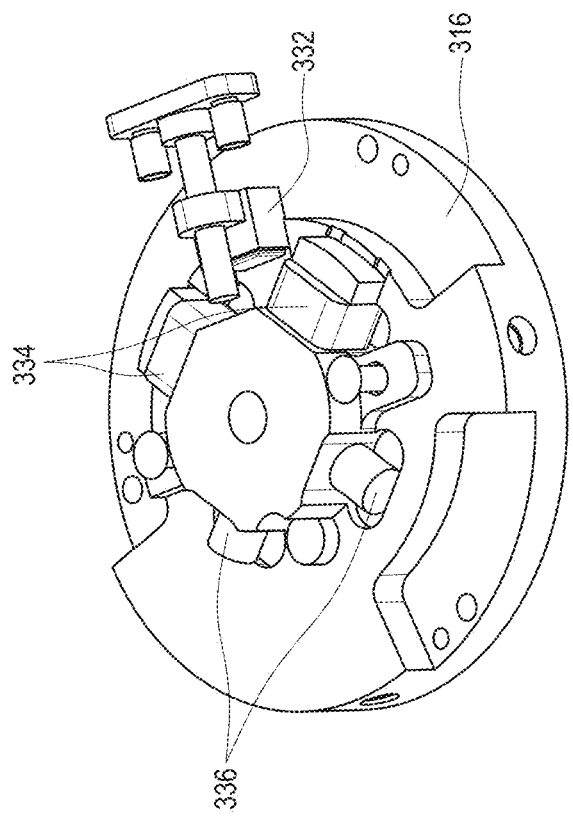
Figure 11D:
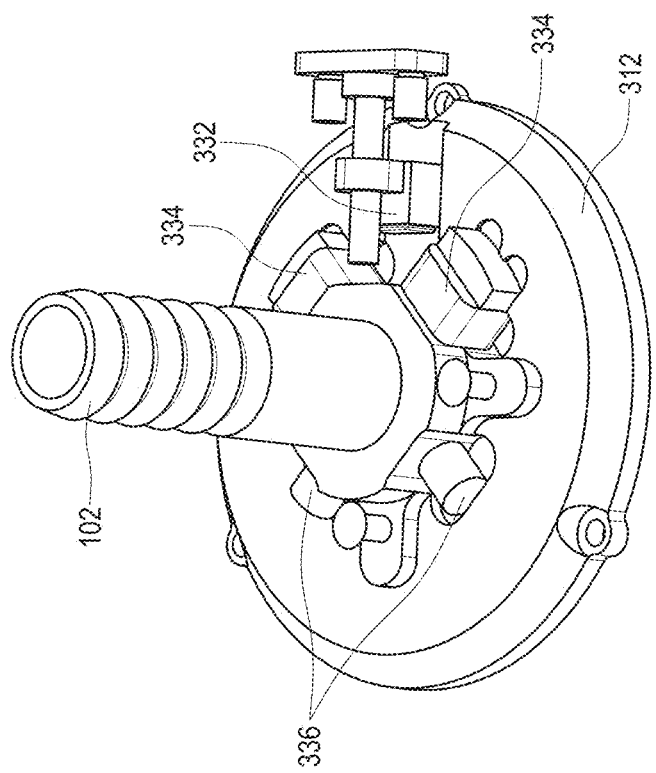

The impeller 200 can be magnetically suspended in the radial direction via various combinations of passive (i.e. permanent) magnets, active (i.e. electrically activated) magnets or electromagnets (e.g., conductive coils wrapped around a metal core), and a hydrodynamic journal bearing effect between the impeller 200 and the internal surface of the casing 300. FIGS. 11A-11E illustrate the components that can be used for radial suspension and stabilization. FIG. 11A shows an example of the orientation of magnets and sensors used for radial suspension. A passive radial-suspension magnet 332 may be positioned adjacent to each impeller ring magnet 230 (e.g., behind the internal surface of the casing 300) along the axial direction. The passive radial-suspension magnets 332 may be adjustable. For instance, the passive magnets 332 may be manually translatable in a radial direction such that the passive magnets 332 may be moved closer to or further from the impeller 200. In some implementations, the passive magnets 332 may be positioned in magnet irons comprising an aperture that can be slid or translated along a rod, pin, or screw in the radial direction. One or more active radial-suspension magnets 334, described elsewhere herein, may similarly be positioned adjacent to each impeller ring magnet 230 (e.g., behind the internal surface of the casing 300). One or more eddy current sensors 336, described elsewhere herein, may be positioned adjacent to each impeller ring magnet 230 (e.g., behind the internal surface of the casing 300). FIG. 11B illustrates an example of a top radial magnet holder 406 and FIG. 11C illustrates an example of a bottom radial magnet holder 408. The radial magnet holders 406, 408 can be used to position (e.g., clamp) the radial-suspension magnets 332, 334 and/or eddy current sensors 336 adjacent to the casing 300. The radial magnet holders 406, 408 may comprise indentations and/or spaces sized to receive or partially receive the radial suspension components, as shown in FIGS. 11B and 11C. FIGS. 11D and 11E illustrate the radial-suspension magnets 332, 334 and eddy current sensors 336 seated on the surface of the casing 300. In some embodiments, the upper and lower outer surfaces of the casing 300 are configured to seat all or some of the radial suspension components. FIG. 11D illustrates the upper radial suspension components seated on the top of the lid 312. FIG. 11E illustrates the lower radial suspension components seated on the bottom of the lower volute 316. The casing 300 may comprise identical or similar indentations as the radial magnet holders 406, 408 for partially receiving the radial suspension components, as shown in FIGS. 11D and 11E. The components may be sandwiched between the casing 300 and the radial magnet holders 406, 408. The top and bottom radial magnet holders 406, 408 may each comprise a ring-like shape configured to be coupled around generally cylindrical projections extending from the top and bottom of the casing 300, respectively (e.g., the lid 312 and the lower volute 316). The radial magnet holders 406, 408 may be configured to be secured to the casing 300 by a friction fit or other suitable means.

FIGS. 12A and 12B schematically illustrate two different modes of radial suspension and stabilization. The impeller 200 may be radially suspended by the passive radial suspension magnets 332. This can result in radial instability, according to Earnshaw's theorem, resulting from the axial stiffness. Instability may further result from the magnetic attraction between the motor's rotor 240 and stator 340, described elsewhere herein, and from turbulent flow, including vortices, within the MCS 100. The impeller 200 can be further stabilized by journal bearing forces and/or the active radial suspension magnets 334, as described below.

In some embodiments, as shown in FIG. 12A, a single passive radial-suspension magnet 332 is used to push the impeller 200 toward the opposite side of the casing 300, creating a large hydrodynamic bearing effect between the impeller 200 and casing 300. The combined magnetic force between the passive radial-suspension magnet 332 and the impeller ring magnet 230 and the journal bearing force may create a radial equilibrium which is highly eccentric, such that the impeller 200 rotates around an axis offset from the central longitudinal axis of the casing 300. This mode of radial suspension advantageously does not consume additional power because only passive magnets are used and stabilization can be accomplished without additional circuitry and/or sensors. In some embodiments, more than one passive radial-suspension magnet 332 may be positioned around each impeller ring magnet 230.

In other embodiments, as shown in FIG. 12B, the passive radial-suspension magnet 332 may be positioned further from the casing 300 than the mode depicted in FIG. 12A, such that the impeller equilibrium axis is positioned approximately along the central longitudinal axis of the casing 300. Because a less strong journal bearing force is created in this arrangement, the equilibrium point may be less stable. The active radial-suspension magnets 334 may be used to prevent or inhibit oscillations from the equilibrium point. Eddy current sensors 336 may be used to monitor the position of the impeller 200, as depicted in FIG. 12B. The active radial-suspension magnets 334 may be actuated by a control circuit according to input from the eddy current sensors 336 to stabilize oscillations. The active radial-suspension magnets 334 may not act to independently suspend the impeller 200 in order to limit power consumption. This mode of radial stabilization may be advantageous because it may result in lower shear stress on the impeller 200. Lower shear stress may also reduce the amount of haemolysis in the pumped blood. Additionally, the active stabilization allows the MCS 100 to react to dynamic shocks, such as a patient falling over. In some embodiments, two active radial-suspension magnets 334 may be positioned around the passive radial suspension magnet 332. The active magnets 334 may be positioned on the same side of the impeller 200 as the passive magnet 332 and may be symmetrically spaced relative to the passive magnet 332. Two eddy current sensors 336 may be positioned on the opposite side of the impeller 200 as the magnets 332, 334. Each eddy current sensor 336 may be positioned opposite one of the active magnets 334. In alternative embodiments, the MCS 100 may rely on one or more other types of bearings to suspend and stabilize the impeller, including ball bearings, roller bearings, and/or needle bearings.

In some embodiments, the active magnets 334 may be positioned near the ring magnets 230 in a position at least slightly axially displaced from the ring magnets 230 such that activation of the active magnets 334 creates magnetic axial displacement forces between the impeller 200 and the casing 300. The axial displacement forces may be used to modulate the axially suspended position of the impeller 200 with respect to the casing 300. Application of pulsatile phases of current to the active magnets 334 may be used to oscillate the impeller 200 along an axial direction and to produce a pulsatile flow. In other embodiments, additional electromagnets distinct from the active magnets 334 may be used to produce the pulsatile flow. In some implementations, the additional magnets may only be positioned near the upper or lower ring magnets 230 rather than both.

In some embodiments, the inner axial surface of the casing 300 and/or the outer axial surface of the impeller 200, or portions thereof, may comprise circumferential grooves. In some implementations, the grooves may be spiraled axially. The grooves may have axial gaps between about 100 μm and about 1 mm (e.g., 200 μm, 500 μm, 700 μm, etc.). The grooves may decrease skin friction drag, thereby increasing the efficiency of the MCS 100, and may enhance washout flow from the MCS 100. The grooves also may improve impeller 200 stability by making it easier to axially suspend the impeller 200 by adjusting the axial-suspension magnets 330.

Figure 13A:
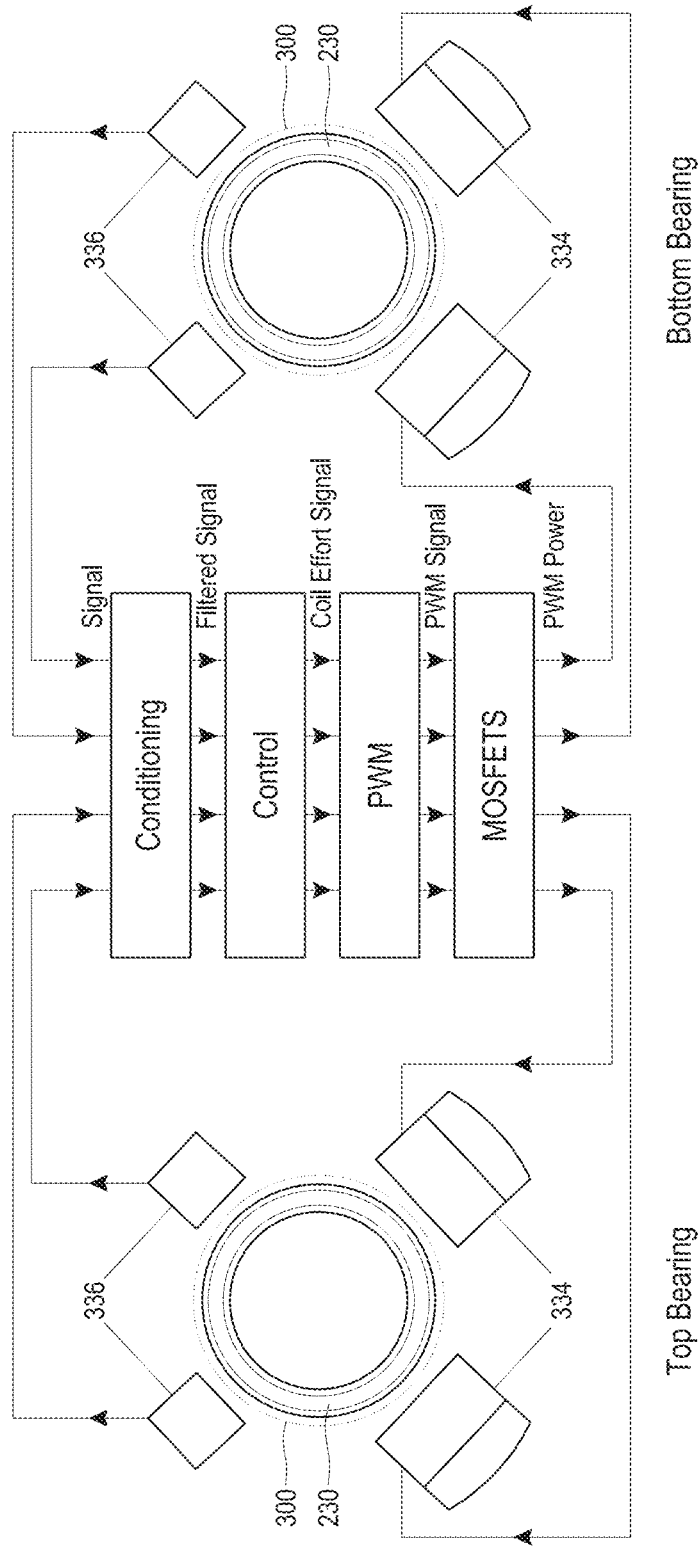
FIGS. 13A-13B schematically illustrate the electrical operation of the electromagnetic stabilization system.
Figure 13B:
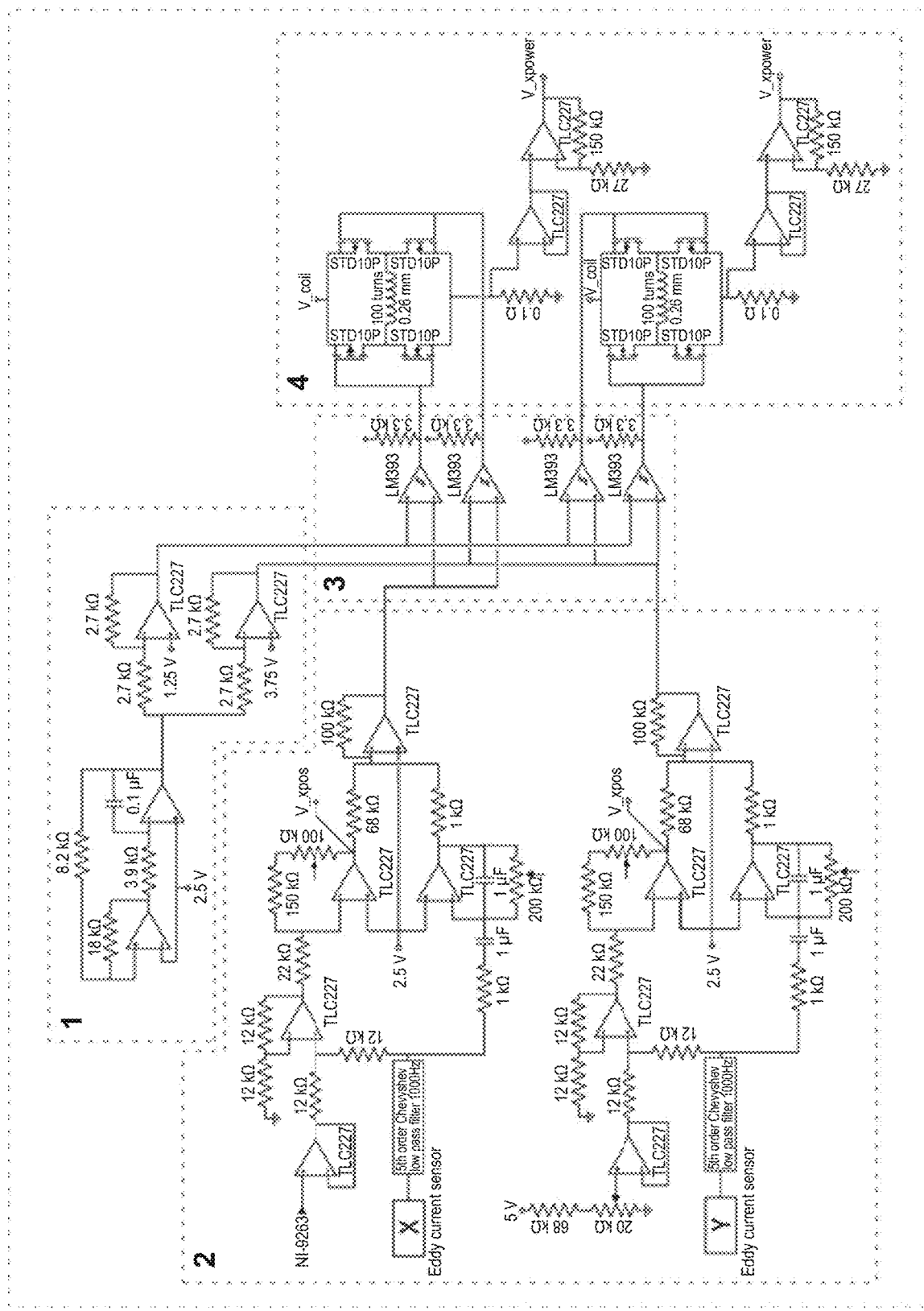

FIG. 13A schematically illustrates a block diagram showing an example of the circuitry components for operating the magnetic suspension (i.e. maglev) system. FIG. 13B schematically illustrates the circuit as divided between the four components (blocks 1-4) of the block diagram in FIG. 13A. A conditioning component (block 1) converts and filters the eddy current sensor 336 output into a voltage that can be read by the control circuit. The conditioning component may be a sawtooth generator. The control circuit (block 2) uses the sensor input along with external input (the maglev offset) to determine the effort in the corresponding coils of the active radial-suspension magnets 334. The pulse width modulation (PMW) component (block 3) converts the control circuit output into a pulse width modulated signal that can be used to drive coil switching in the active radial suspension magnets 334. The PMW component may use comparators. Finally, power MOSFETS (block 4) are driven by the pulse width modulated signal to supply power to the active radial-suspension magnets 334 configured to stabilize the impeller 200.

Figure 14A:
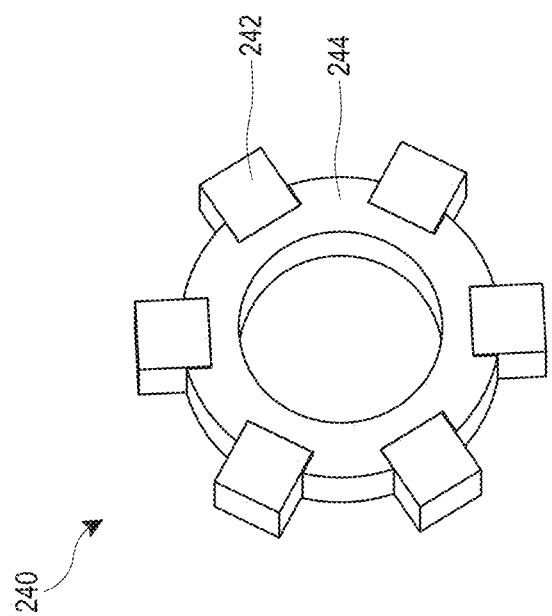

The magnetically suspended impeller 200 may be electromagnetically actuated to rotate around its longitudinal axis within the casing 300 via an electromagnetic motor. In some embodiments, the motor may be a radial brushless motor, such as a radial brushless DC motor. The motor may be a radial three-phase brushless DC motor. The motor generally comprises a stator 340 positioned within the casing 300 and a rotor 240 positioned within the impeller assembly 201 and aligned concentrically inward of the stator 340. FIGS. 14A and 14B depict examples of a rotor 240. FIG. 14A shows a perspective view of the rotor 240. FIG. 14B shows a perspective view of the rotor 240 assembled with the impeller 200 in the impeller assembly 201. The rotor 240 may include passive drive magnets 242 positioned around a ring 244. The drive magnets 242 may be positioned on the outer circumference of the ring 244 such that they extend radially outward from the ring 244. The drive magnets 242 may be partially embedded within the ring 244. The drive magnets 242 may be uniformly spaced around the circumference of the ring 244. There may be any number of drive magnets 242. In some embodiments, there is a 3:2 ratio of stator magnets to drive magnets 242. In some embodiments, there may be six drive magnets 242. The drive magnets 242 may comprise neodymium (NdFeB). The drive magnets 242 may be generally cubic in shape and may have dimensions of about 5×5×5 mm. The ring 244 may comprise steel. The rotor 240 may be configured to be inserted into the impeller 200. For example, as shown in FIG. 14B, the rotor 240 may be dimensioned to be inserted into the upper chamber 212 of the upper portion 212 of the impeller 200 as described elsewhere herein. The rotor 240 may be coupled to the impeller 200 by any suitable means, including but not limited to, welding, biocompatible adhesive, or a tight interference fit with the outer circumference of the top port 202.

Figure 15B:
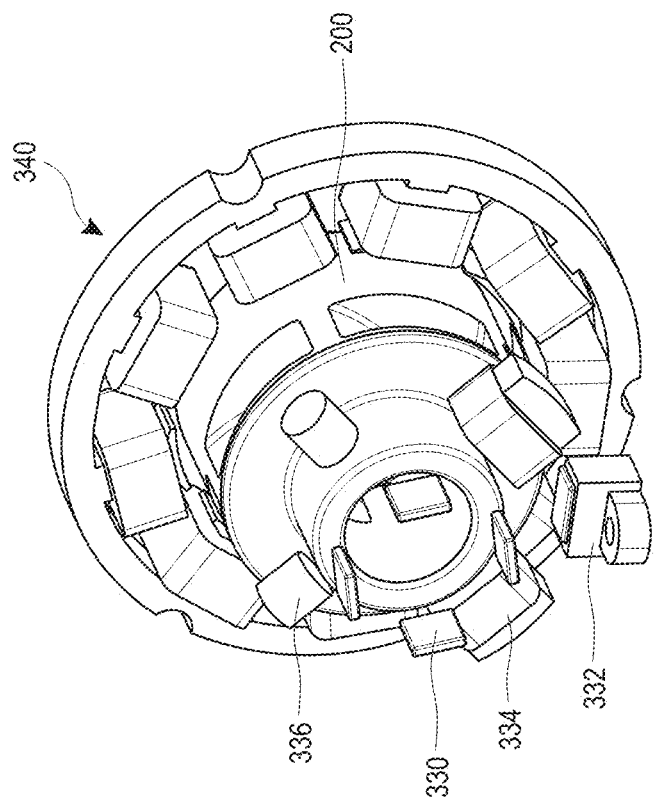
FIGS. 15A-15B illustrate an example of a MCS stator.
Figure 15A:
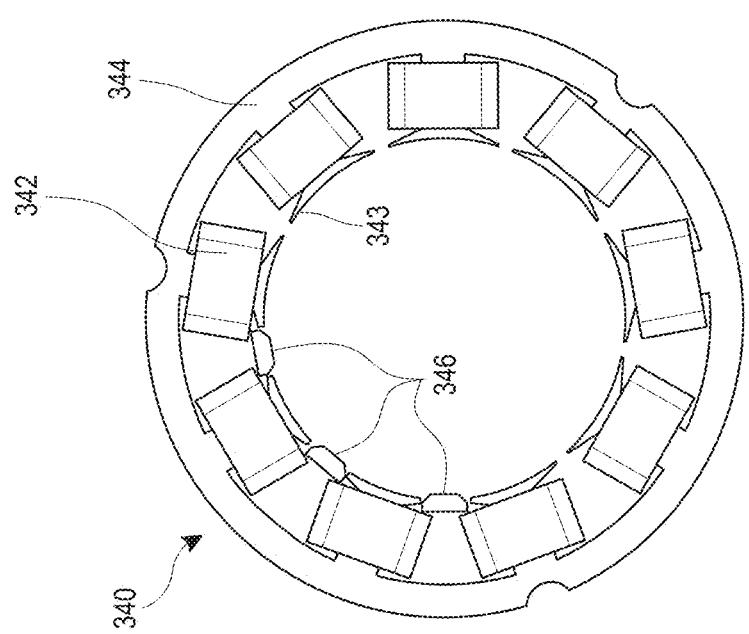

FIGS. 15A and 15B depict examples of a stator 340. FIG. 15A shows a top view along the longitudinal axis of a stator 340. FIG. 15B shows a perspective view of the stator 340 positioned around the outer circumference of the impeller 200. The stator 340 may include active magnets 342 positioned around a ring 344. The ring 344 may comprise silicon steel. The stator magnets 342 may be positioned on the inner circumference of the ring 344 such that they extend radially inward from the ring 344. The stator magnets 342 may be uniformly spaced around the circumference of the ring 344. There may be any number of stator magnets 342. In some embodiments, there is a 3:2 ratio of stator magnets 342 to drive magnets 242. In some embodiments, there may be nine stator magnets 342. The stator magnets 342 may comprise metal conductive coils wrapped circumferentially around projections extending inward from the ring 344. The coils may comprise copper. Electric current provided to the conductive coils may be used to create the electromagnetic forces of the active magnets. The radially inward end of the projections around which the coils are wrapped may comprise circumferentially extending flanges 343 which extend towards each other and align with each other to form a partially closed inner diameter configured to sit around an outward facing surface of the casing 300 (not shown). Larger gaps may be formed between several of the flanges on adjacent projections. The gaps may be configured for allowing the positioning of hall effect sensors 346, described elsewhere herein, adjacent to the outer surface of the casing 300, as shown in FIG. 15A. In some embodiments, multiple axially-aligned stators 340 (e.g., three stators 340) may be used. The stator 340 may be positioned within the casing 300. For example, the stator 340 may be positioned within the upper volute 314.

The motor may be driven by sequentially applying three phases of voltage (positive voltage, zero voltage, and negative voltage) to each stator magnet 342 to induce three phases of current (positive, zero, and negative) and polarity (positive, non-polar, negative). Pulses of positive and negative polarities may travel circumferentially around the stator ring 344 to continuously drive the rotor 240 through magnetic interaction with the drive magnets 242. A controller, which may be external to the MCS 100, may be used to time the charging of each stator magnet 342 so as to induce continual rotation of the rotor 240. One or more bipolar hall effect sensors 346 (e.g., three sensors) positioned within the casing 300 may be used to detect the positioning of the rotor 240 with respect to the stator 340 by detecting the proximity of a drive magnet 242. The controller may monitor the output of the one or more hall effect sensors 346 and use the positioning location to modulate the activation of the stator magnets 342. In some embodiments, the hall effect sensors may be Honeywell part number SS411A sensors.

The electrical systems of the MCS 100 may control the motor and magnetic suspension systems, as well as power conditioning and battery charging. The electrical systems, or a portion of the electrical systems, may be external to the MCS 100. The electrical systems may be powered by an internal rechargeable battery, such as a chemical battery (e.g., lithium ion) or the battery may be used as a backup power source. The internal battery (or batteries) may be implanted within the body at a position separated from the MCS 100 device. For example, the internal batteries may be contained in a separate controller device implanted in the body, similar to the manner in which a pacemaker is implanted within a body. The controller may also contain the other electrical systems. In some embodiments, the battery may be charged transcutaneously, via inductive power transfer through the skin. In some embodiments, the MCS 100 is primarily powered by an external battery (e.g., a 16.8 V battery), but may have an internal battery for backup. Power from the external battery may also be transferred transcutaneously through the skin. FIG. 16A, schematically depicts the components of an example of a transcutaneous energy transmission system (TETS), including various component efficiencies ($\eta$). An external battery charger may receive line AC voltage (e.g., 110-240 VAC) and convert it to DC voltage to charge external batteries (e.g., lithium ion batteries). A DC-DC converter may be used to stabilize the DC voltage provided by the external batteries (e.g., while they discharge). A DC to high frequency (HF) converter may convert the DC voltage into a high frequency (e.g., 250 kHz) AC voltage for transcutaneously charging a secondary coil beneath the skin from an external primary coil (e.g., spaced 20 mm apart). Higher frequencies may be required to transfer energy between coils spaced further apart. The coils may be made of Litz wire. An HF to DC converter may be used to convert the energy back to DC within the body. An internal DC-DC converter may be used to stabilize the DC voltage supplied to the controller. The controller may be electrically connected to the MCS 100 (denoted as "TC") via suitable wiring, including input and output capabilities. The controller may include intelligent functioning mechanisms, including constant monitoring of power consumption, impeller rpm, blood pressure, and other performance parameters. Information may be wireless transmitted to and/or from the controller, such as to a patient, physician, or hospital.

The controller may also include internal rechargeable batteries. The internal batteries may serve as temporary backup for when the TETS is disconnected. The internal batteries may be charged from the output of the HF to DC converter. An undercurrent transducer may be used to sense current from the external batteries and switch between power supplied directly from the HF to DC converter to power supplied from the internal batteries, if the current is below a predetermined threshold. Larger batteries may provide longer independent operation times. Charging the batteries at lower currents (e.g., 0.2A) may advantageously limit the temperature rise of the devices, although longer charging times may be needed. In some embodiments, the battery may be charged percutaneously. FIG. 16B, schematically depicts the components of an example of a percutaneous energy transmission system (PETS), including various component efficiencies (η). The MCS 100 may include any suitable means for minimizing the electromagnetic interference from other sources, including but not limited to, optimizing the voltage and current for a constant power, modifying the frequency of the signals, and using filters, shields, and/or snubber circuits.

Figure 16C:
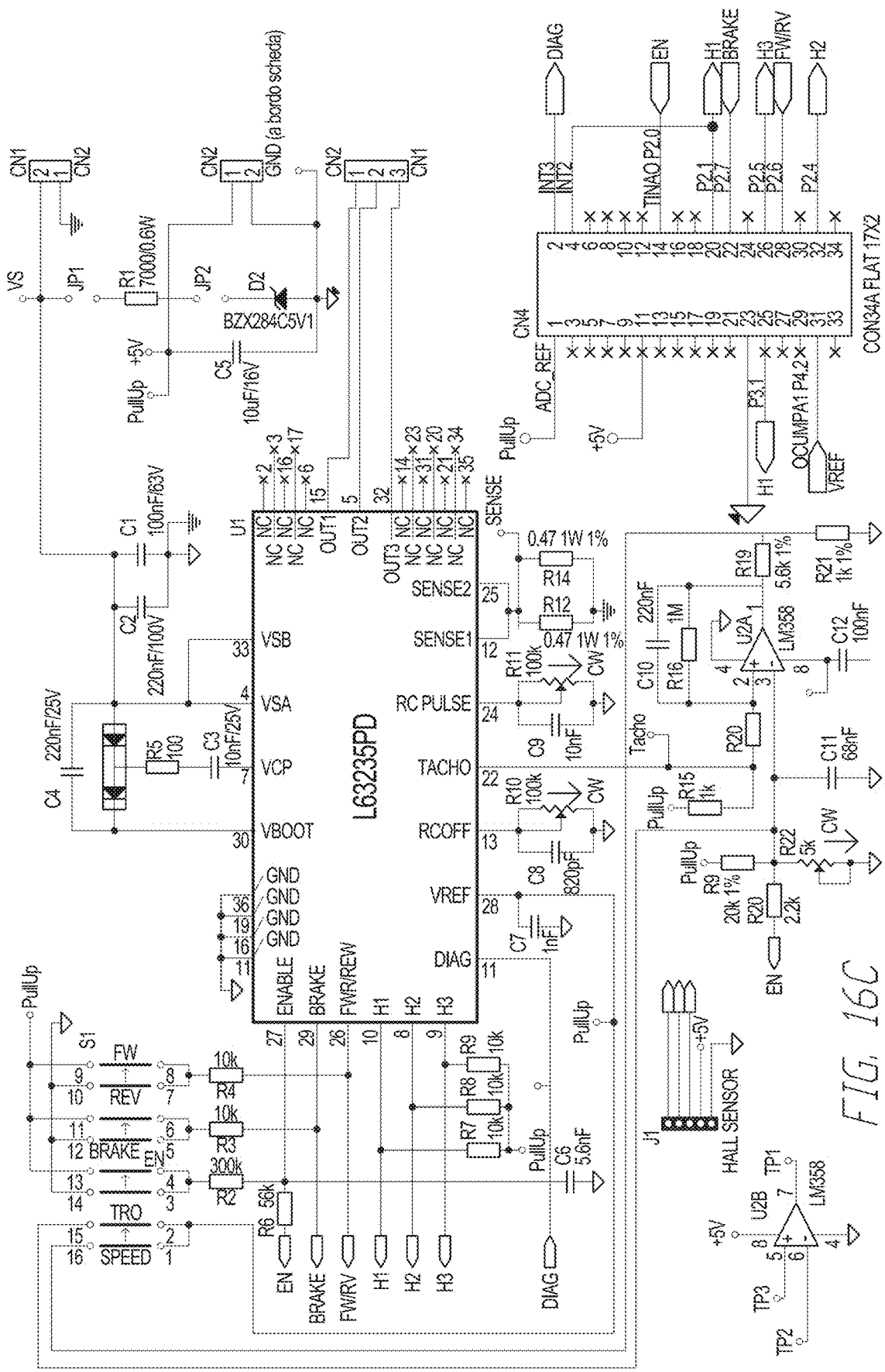
Figure 16D:
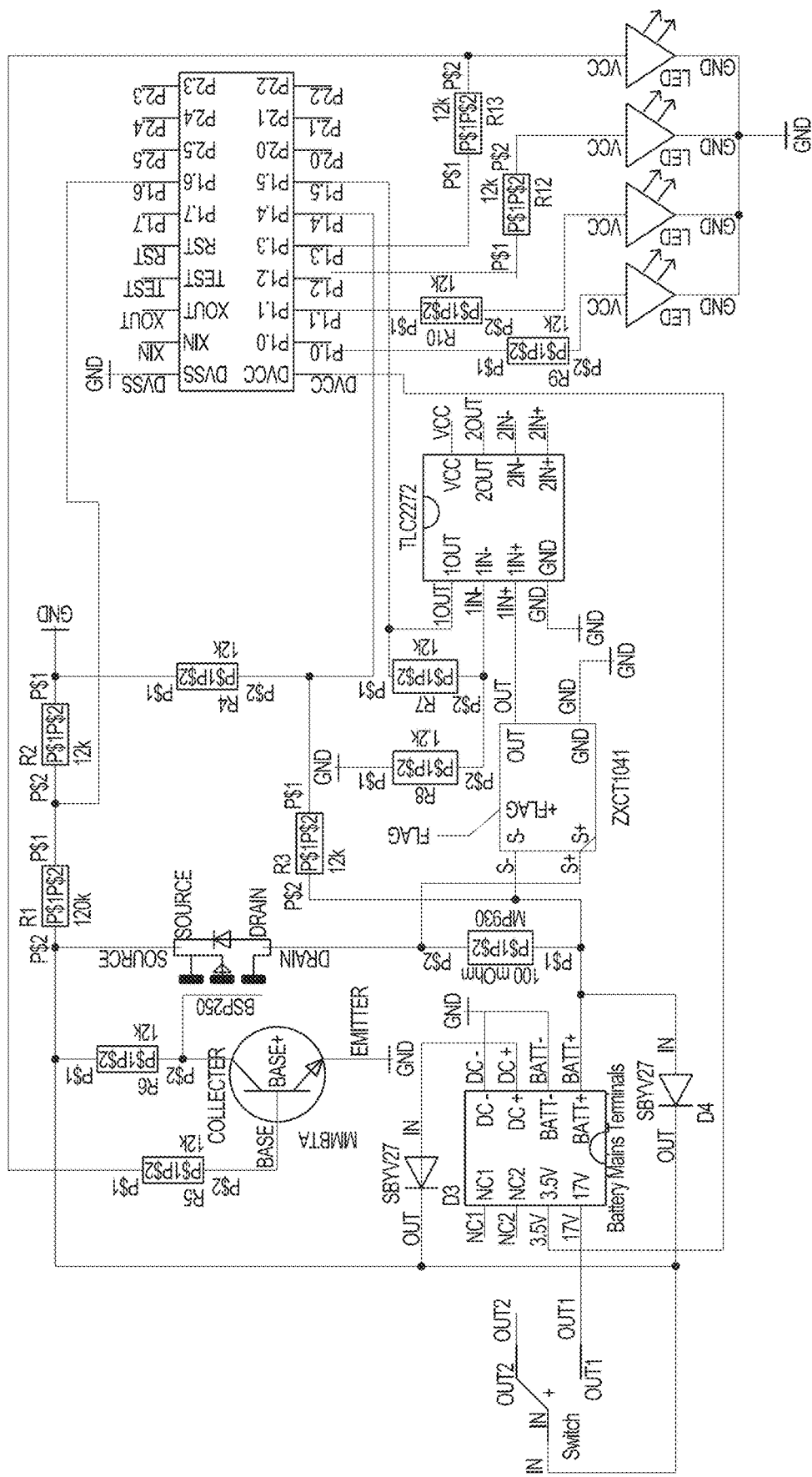
Figure 16E:
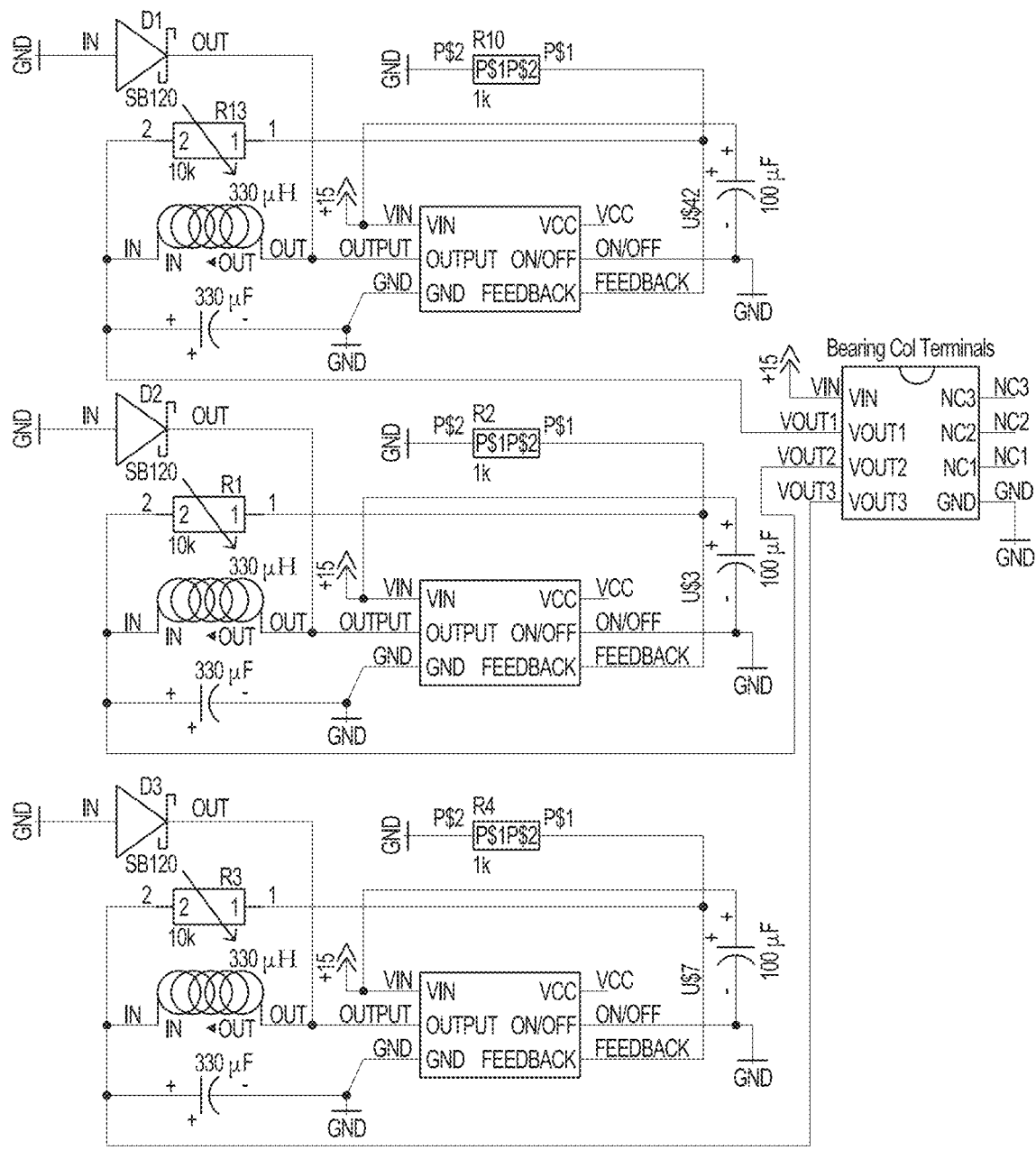

The controller may contain electronic circuitry for operating the MCS 100. In some embodiments, the motor can be driven using an L6235 driver chip (ST Microelectronics). FIG. 16C schematically illustrates the L6235 driver chip circuit. This circuit can be used to power the hall effect sensors, monitor their output, and drive the three phases accordingly. FIG. 16D schematically illustrates a battery charging circuit. The battery charging circuit may use an MSP430 microcontroller to monitor battery voltage and/or current into the battery via a ZXCT1041 current monitor. The microcontroller may stop charging to prevent overcharging if the battery is fully charged and the current into the battery is below 0.02C. Charging may resume when the battery voltage drops below a predetermined threshold. Power into the battery may be controlled by an MMBTA bipolar junction transistor and a BSP250 MOSFET. A variety of charging algorithms may be programmed into the microcontroller. FIG. 16E schematically illustrates a power conditioning circuit. The power conditioning circuit can be used to create lower voltage levels from the battery (e.g., a 16.8 V battery) as described elsewhere herein. Running some circuits at lower voltages may reduce the power consumption of the MCS 100. Adjustable DC-DC current regulators may be used to ensure efficient conversion. In some implementations, the control electronics, digital filtering, and maglev actuators may be powered at 3.5 V, 5 V, and 6.5 V respectively. In some implementations, the control electronics, digital filtering, and maglev actuators may be powered at 3.5 V, 3.5 V, and battery power (e.g., 16.8 V) respectively, which may provide lower cost, complexity, and power consumption. Electrical power may be provided from the controller to the MCS 100 via electrical wires 109, illustrated in FIG. 5B. There may be multiple wires extending between the controller and the MCS 100. For instance, there may be a wire providing power to the radial suspension electromagnets, a wire providing power to the electromagnets of the motor, a wire receiving input from the eddy current sensors, a wire receiving input from the hall effect sensor, etc. Power and data may be transferred between the controller and the MCS according to any suitable means known in the art.

The MCS 100 may be optimized for performing in-series in a patient with late stage III and/or early stage IV CHF. The MCS 100 may be optimized to provide maximum power efficiency, minimize occupying space, and/or reduce device weight. Optimizing power efficiency may reduce battery weight and/or maximize untethered time during which the device may be operated via battery power. The device may be configured to optimize stability of the rotating impeller 200 to prevent damage to the device and/or blood trauma. Losses in motor efficiency may be electrical, magnetic, and/or mechanical. Electrical efficiency losses may, for example, include winding resistance (i.e. copper loss), especially in low speed applications. Magnetic efficiency losses may include hysteresis, eddy current losses, and/or excess eddy current. Mechanical losses may include windage, ventilation, and/or bearing friction. In some embodiments, the efficiency is at least 15%. In some embodiments, the efficiency is at least 20%. In some embodiments, the power consumption may be about 10 W or less. Efficiency may generally be increased by using a smaller impeller with reduced skin friction to improve hydraulic efficiency. Efficiency may generally be increased allowing more space for coils and/or reducing the stator-rotor gap to improve electromechanical efficiency at the operating condition. Stability may generally be improved by increasing the stator-rotor gap.

Figure 16F:
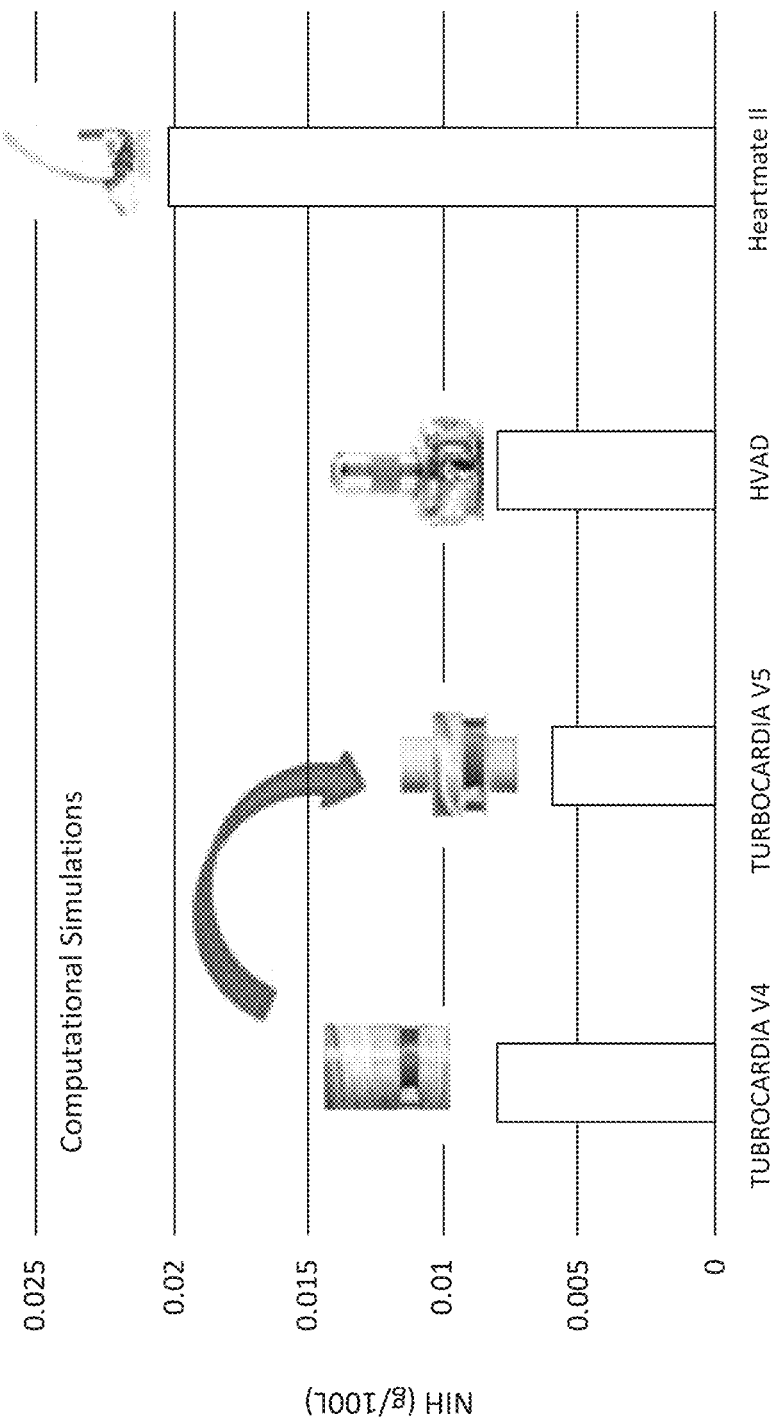

The operating design may be configured to minimize damage to the blood so that haemolysis is low. Haemolysis is the result of blood trauma imparted by high shear and by time of exposure (or length of flow passage) in high-shear flow conditions. For a set flow rate (e.g., 5 L/min) and to a first approximation, increasing the pressure requires larger power inputs to the flow and therefore results in larger losses by friction. Accordingly, the blood trauma imparted by a VAD or MCS increases as the pressure rises. Therefore, as the MCS 100 is designed to provide 40-80 mmHg, it will result in lower haemolysis than another MCS or VAD delivering 5 L/min at much higher pressure rises (e.g., 120-140 mmHg). FIG. 16F depicts the Normalised Index of Haemolysis (NIH, g/100 L) of computation simulations on the MCS 100 (depicted as TURBOCARDIA V5) as well as a prior version having an impeller comprising larger upper and lower portions 214, 216 amongst other design differences (depicted as TURBOCARDIA V4) and other VADs known in the art (the HVAD and Heartmate II). In some embodiments, as demonstrated in FIG. 16F the computed haemolysis of MCS 100 may be around 0.6 g/100 L. In other embodiments, the computed haemolysis may be less than 0.6 g/100 L.

The MCS 100 may be configured for installation within a portion of the descending aorta. The MCS 100 may be configured to provide approximately a 40-80 mmHg pressure rise (e.g., about 70 mmHg) at a continuous flow rate of about 5 L/min. The MCS 100 may be configured to operate the rotor 240 at approximately 2600 rpm. In some embodiments, the device may weigh about 150 g. The displacement volume may be about 70 cm³. Referring back to FIG. 5D, example dimensions (in mm) of various MCS 100 components and the overall dimensions of the MCS 100 are depicted (the illustrated dimensions may not be drawn to scale). The outer diameter of the MCS 100 (around the casing 300) may be between about 30 mm and about 100 mm, between about 40 mm and about 70, between about 50 mm and about 60 mm, and ranges there between (e.g., about 57 mm). The axial length of the casing 300 may be between about 20 mm and about 60 mm, between about 30 mm and about 50 mm, between about 35 mm and about 45 mm, and ranges there between (e.g., about 40 mm), excluding the length of the inlet 102. The impeller 200 may have a maximal radial diameter between about 10 mm and about 60 mm, between about 20 mm and about 50 mm, between about 25 mm and about 40 mm (e.g., 30 mm). The diameter of the upper channel 203 may be between about 3 mm and about 25 mm, between about 5 mm and about 20 mm, between about 8 mm and about 12 mm, and ranges there between (e.g., about 10 mm). In some embodiments, as shown in FIGS. 5C, 5D, and 6B the diameter of the upper channel 203 may decrease from the inlet 102 to the blade passage chamber 216. For example, the diameter of the upper channel 203 may linearly decrease from about 12 mm to about 8 mm. In other embodiments, the upper channel may have a constant diameter or a diameter than decreases in a non-linear manner. The diameter of the lower channel 205 may be between about 3 mm and about 30 mm, between about 5 mm and about 20 mm, between about 8 mm and about 12 mm, and ranges there between (e.g., 10 mm). The diameter of the lower channel 205 may be constant as shown in FIGS. 5C, 5D, and 6B. In other embodiments, the diameter may increase in a linear or non-linear manner from the blade passage chamber 216 to the bottom of the impeller 200. The height of the blade passage chamber 216 may be between about 2 mm and about 30 mm, between about 3 mm and about 10 mm, and ranges there between (e.g., 5.5 mm). The height of the diffuser 320 may be between about 2 mm and about 30 mm, between about 3 mm and about 10 mm, and ranges there between (e.g., 7 mm). In some embodiments, as described elsewhere herein, the height and/or depth of the diffuser 320 may vary depending on the circumferential position. The gaps between the impeller 200 and the casing 300 in the peripheral space 322 may be between about 100 μm and 1 mm (e.g., 700 μm). The width of the peripheral space 322 may be the same or may vary around different portions of the impeller 200 and casing 300. The precise width of the peripheral space 322 may depend on the operation of the MCS 100, including the axial and radial suspension, as described elsewhere herein. The inlet 102 may have an inner diameter of about 9 mm. The inner diameter of the inlet 102 may be the same or less than the diameter of the upper channel 203 where the inlet 102 and upper channel 203 meet. The outlet 104 (not shown) may have an inner diameter of about 11 mm. In alternative embodiments, the MCS may be configured for installation in the ascending aorta. The MCS configured for installation in the ascending aorta may comprise a second outlet which could be configured to send about 5% of the blood flow to the coronary arteries and the remainder of the blood flow downstream.

The MCS 100 can be installed within the vasculature 2 in various configurations. In various embodiments, the MCS 100 comprises an inlet 102 and an outlet 104, which may be arranged generally perpendicular to each other as described elsewhere herein. The outlet 104 may be positioned at the end of a diffuser for altering and/or reorienting the fluid outflow. The MCS 100 can be installed into the vasculature using vascular grafts comprising standard biocompatible graft material (e.g., polytetrafluorethylene, polyethylene terephthalate, etc.). In some implementations, patient allografts may be used. The grafts may be connected to the inlet 102 and outlet 104 of the MCS 100 in any suitable manner which creates a fluid tight seal. The grafts may be sutured into the native vasculature.

In some embodiments, the MCS 100 is installed at an angle relative to the axis of the aorta. For example, FIG. 17 schematically depicts an example of an MCS 100 installed in-series with the descending aorta, in which the inlet 102 and the outlet 104 of the MCS 100 are anastomosed to the aorta by an inlet graft 106 and an outlet graft 108. The grafts 106, 108 may extend from the axis of the aorta at an angle selected from a wide array of angles generally between 0 degrees and 90 degrees. For embodiments of the MCS 100 in which the inlet 102 is substantially perpendicular to the outlet 104 (i.e. 90 degrees), the sum of the angle of the inlet 102 relative to the aorta and the angle of the outlet 104 relative to the aorta is approximately 90 degrees, when the MCS 100 is installed within a generally straight portion of the aorta. For example, as shown in FIG. 17, the inlet 102 and outlet 104 of the MCS 100 are each arranged approximately 45 degrees relative to the descending aorta. The installation of the MCS 100 within the aorta, particularly at an angle, may somewhat displace or alter the orientation of the upstream and/or downstream portion of the aorta to which the MCS 100 is anastomosed.

In some embodiments in which neither the inlet 102 nor the outlet 104 of the MCS 100 is configured to be collinear with the aorta (the MCS 100 is laterally displaced from the aorta), the MCS 100 may be connected in-parallel with the aorta. In embodiments where the MCS 100 is connected in-parallel, the inlet and outlet grafts 106, 108 may be anastomosed with the native vasculature in a branched fashion. In some in-parallel embodiments, the native aorta may be occluded between the inlet graft 106 and the outlet graft 108, effectively making the MCS 100 in-series with the aorta. In some in-parallel embodiments, a one-way valve (e.g., a one-way artificial heart valve) may be installed in the native aorta between the inlet graft 106 and the outlet graft 108, permitting blood flow only in the downstream direction. Mechanically preventing upstream blood flow within the native aorta may advantageously prevent recirculation of blood along a path of least-resistance up the native aorta and back through the MCS 100 when installed in-parallel, which may excessively damage the blood and/or disrupt downstream blood flow.

FIGS. 18A and 18B schematically depict an example of an MCS 100 installed in-parallel with the descending aorta. FIG. 18A shows the MCS 100 installed at approximately a 60 degree angle between the inlet 102 and aorta and approximately a 30 degree angle between the outlet 104 and aorta. FIG. 18B shows the MCS 100 installed at approximately a 90 degree angle between the inlet 102 and the aorta. The outlet 104 is parallel to the bottom portion of the aorta (i.e. 0 degrees) and connected via a curved outlet graft 108. In the example illustrated in FIG. 18B, the inlet and outlet grafts 106, 108 are substantially curved. Using curved grafts may allow the installation of the MCS 100 in the vasculature at sharper angles and/or may minimize the amount of space occupied by the grafts 106, 108 and the MCS 100. The curvature of the grafts may also effect vortex formation as described elsewhere herein. The grafts 106, 108 may be substantially rigid to support the MCS 100 within the vasculature. Grafts of various shapes or flexibility may be employed depending on the amount of curvature desired. Embodiments which use more moderate angles (e.g., 45 degrees) can be advantageous in that their installation can be accomplished using relatively short and/or relatively straight grafts 106, 108, which may minimize the total installation space of the MCS 100. Use of straight grafts 106, 108 may impart less turbulence on the blood flow than use of more curved grafts 106, 108.

Figure 19:
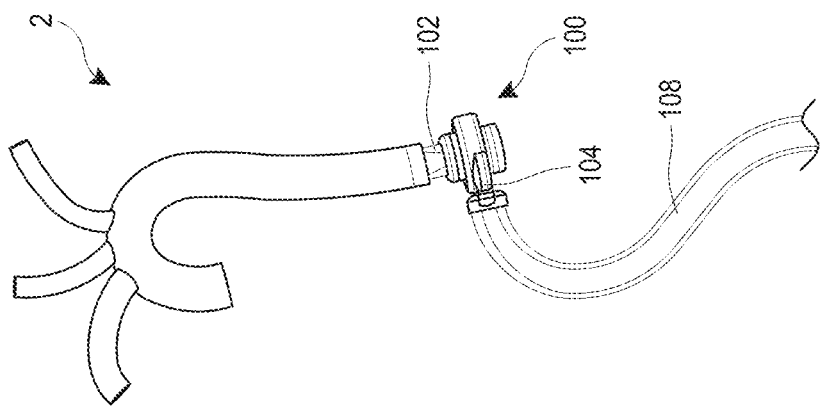
FIG. 19 schematically illustrates an example of an MCS installed collinear with a portion of the descending aorta using a question-mark shaped outlet graft.

In some embodiments, the outlet 104 of the MCS 100 is connected to a substantially curved graft 108 to return blood to the downstream portion of the aorta. The curved outlet graft 108 may extend from the outlet 104 of the MCS 100 in a direction substantially perpendicular to the inlet 102 and curve toward the downstream portion of the aorta until the graft 108 is substantially collinear with the aorta at which point the graft and downstream portion can be anastomosed. FIG. 19, schematically depicts an example of a MCS 100 installed in-series with the descending aorta, in which the inlet 102 is anastomosed to the upper portion of the descending aorta in a collinear manner or at a relatively small angle (e.g., 0-10 degrees) and the outlet 104 is anastomosed to the lower portion of the descending aorta via a generally "question mark" shaped outlet graft 108. This configuration may be advantageous in that it allows installation of the MCS 100 with both the inlet and outlet grafts 106, 108 anastomosed to the native vasculature in a generally collinear fashion. Collinear installation of the MCS 100 may minimize the amount of manipulation required in the native aorta to accommodate the MCS 100. Use of an outlet graft 108 with a large radius of curvature may minimize the amount of turbulence imparted to the blood flow through the MCS 100.

Figure 20:
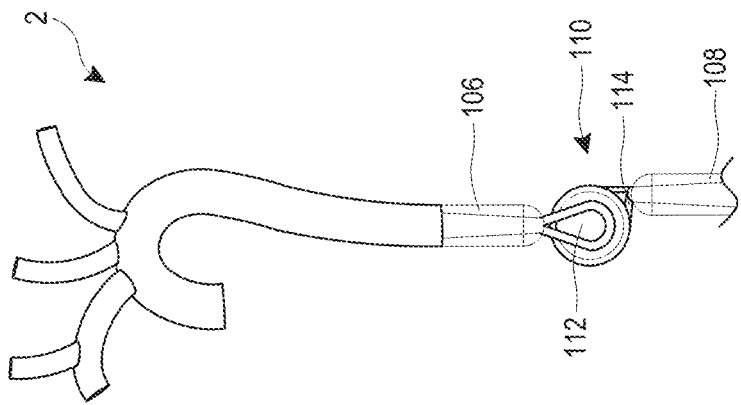
FIG. 20 schematically illustrates an example of a coaxial MCS comprising a 90 degree flow turn at the inlet installed in-series with a portion of the descending aorta.

In some embodiments, an MCS 110 may be installed within the aorta in a co-axial configuration, in which the inlet 112 and outlet 114 are not perpendicular but are coaxial, such that they inlet 112 and outlet 114 are parallel to a common axis, generally aligned with a longitudinal axis of the native aorta. FIG. 20 schematically depicts an example of a coaxial MCS 110 installed within the descending aorta. The inlet 112 includes a 90 degree bend, allowing the inlet graft 106 to remain collinear with the upper portion of the descending aorta. Blood flow enters the coaxial MCS 110 impeller from the 90 degree bend "sideways" with respect to a standing patient. The diffuser sends the blood flow vertically downward with respect to a standing patient. This configuration can result in minimal losses in pump efficiency at the inflow graft 106 as the pressure at that point is relatively low relative to other configurations. The remaining features of the MCS 110 may be the same as that of MCSs 100 installed in angled configurations. The coaxial configuration may result in the formation of a vortex at the MCS outlet 114. In embodiments comprising a sharp 90 degree bend in the inlet 112, the MCS 110 can be installed with relatively short grafts 106, 108 and with minimal installation space. The coaxial MCS 110 may be especially conducive to installation by minimally invasive surgery. In some embodiments, the downstream portion of the severed aorta may be slightly displaced upon installation, such as by 3-10 cm, for example. In other embodiments, the outlet 114 may bend to wrap partially around the body of the MCS 110 such that the inlet 114 and outlet 116 are collinear.

FIGS. 21A-21D schematically depict simulated fluid flow through MCS devices installed in-series with the aorta in various configurations. FIG. 21A shows a MCS 100 installed in an angled configuration with approximately 45 degree angles between the inlet 102 and aorta and the outlet 104 and aorta. FIG. 21B shows a MCS 100 installed in an angled configuration with an approximately 65 degree inlet 102 angle and an approximately 25 degree outlet 104 angle relative to the aorta. FIGS. 21C and 21D show MCSs 100 installed in angled configurations with an approximately 90 degree inlet 102 angles and approximately collinear (0 degree) outlets 104 relative to the aorta. The simulations depicted in FIGS. 21C and 21D may be used to approximate the fluid flow through a coaxial MCS 110 comprising a 90 degree bend in the MCS inlet 112. The example shown in FIG. 21C has a 25 mm radius at the inlet 112 and the example shown in FIG. 21D has a 15 mm radius at the inlet 112. The coaxial MCSs 110 shown in FIGS. 21C and 21D show no discernible vortices in the outflow. The angled MCSs 100 shown in FIGS. 21A and 21B show discernible vortex formation in the outflow of each. The simulation results suggest that bending in the outlet may create more fluid vortices than does bending in the inlet. The relatively low pressure at the inlet 102 and the relatively high pressure at the outlet 104, of the angled MCS devices 100, may stimulate vortex formation. The size of the diffuser at the outlet may also effect vortex formation.

Vortex formation in the outflow of the MCS 100, 110 may be beneficial. For instance, vortex flow may enhance the perfusion of side arteries branching from the aorta and/or may enhance washout in the descending aorta. Using the MCS to recreate physiological flow conditions may reduce the risk of thrombosis or other pathological conditions. Studies have shown the identification of right-handed helix formation through the ascending aorta and aortic arch into the descending aorta during systolic outflow in healthy individuals. See Markl, M. et al. (July 2004). Time-Resolved 3-Dimensional Velocity Mapping in the Thoracic Aorta: Visualization of 3-Directional Blood Flow Patterns in Healthy Volunteers and Patients, *Journal of Computer Assisted Tomography,* 28(4), 459-468 (incorporated herein by reference). In some embodiments, the MCS and/or the installation of the device may be configured to optimize vortex formation (e.g., to form a right-handed helix) in the outflow of the device. For example, the direction of impeller rotation, orientation of the diffuser, inflow angle, outflow angle, inlet diameter, and/or outlet diameter may be selected to emulate optimal physiological conditions, including a weak vortex. Depending on the geometry of the MCS, these parameters may be used to either increase or decrease the amount of vortex formation to mimic that of the native aorta. Prior MCS devices have aimed to eliminate any vortex formation altogether.

Figure 22A:
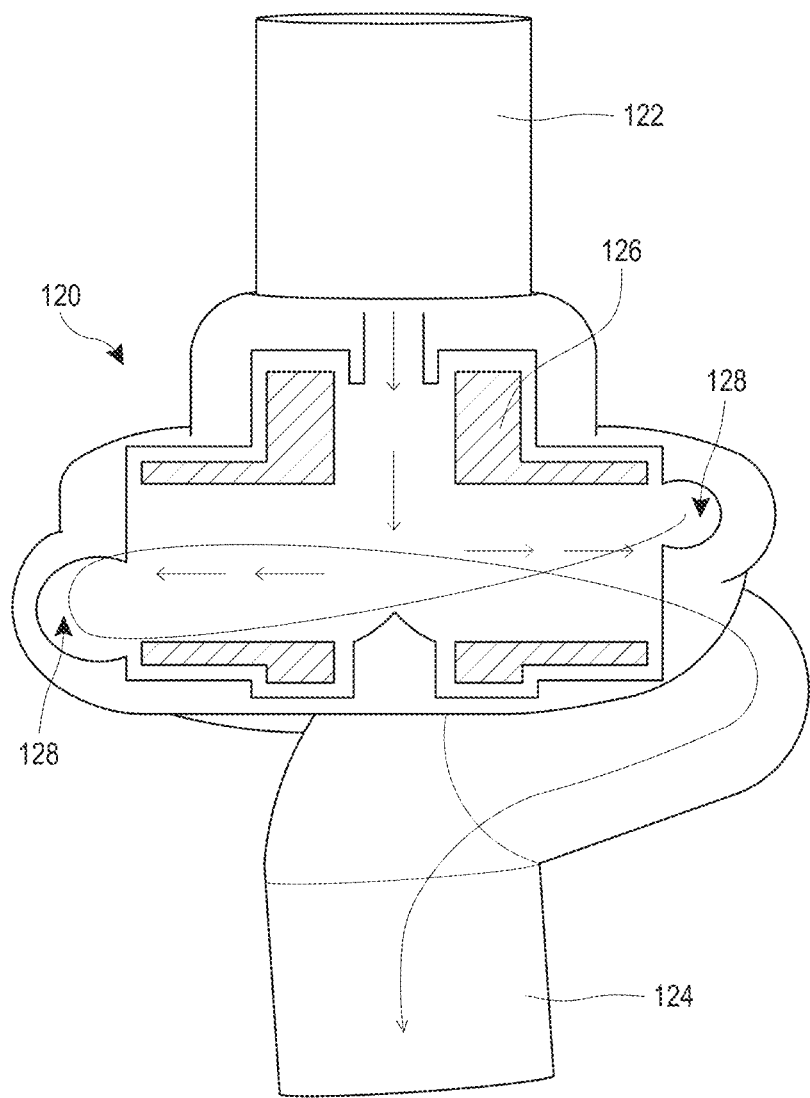
FIGS. 22A-22C schematically illustrate an example of a collinear MCS with a wrap-around diffuser and volute passage.
Figure 22C:
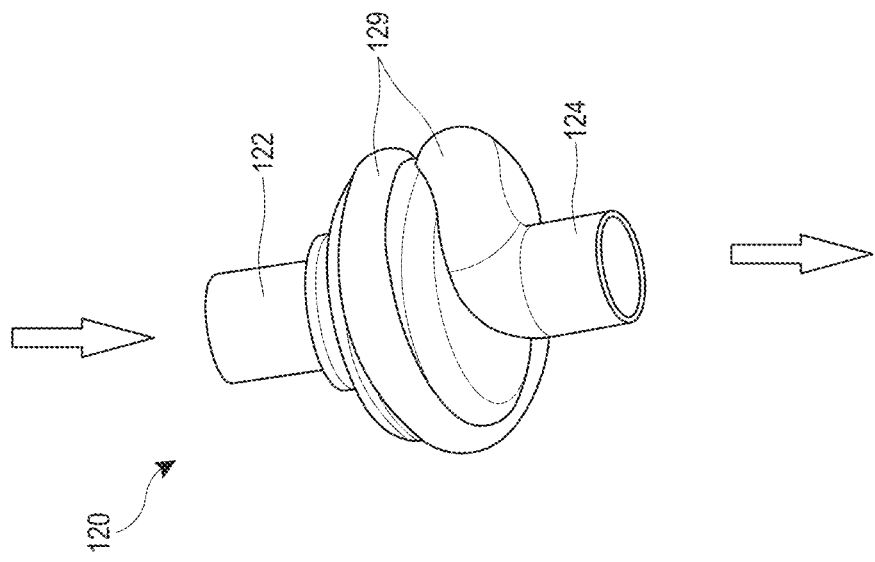
Figure 22B:
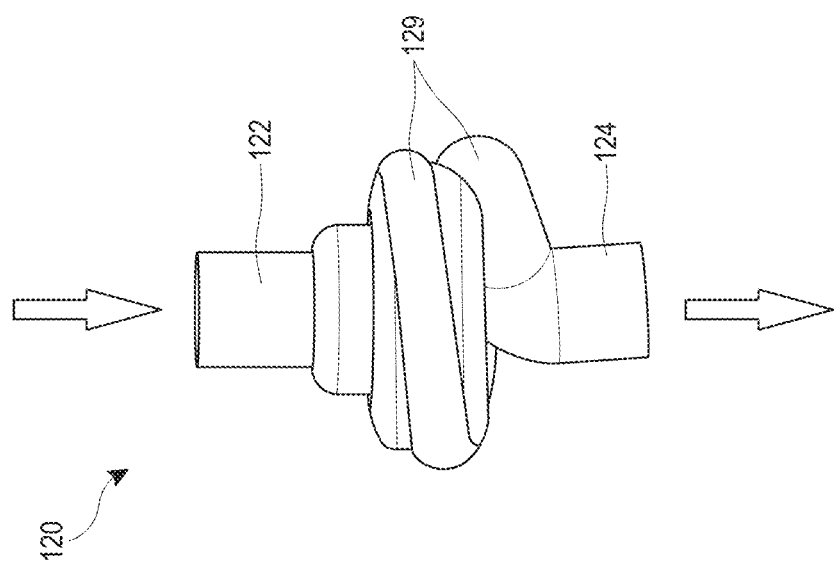

In some embodiments, the MCS is collinear with both the upper portion and the lower portion of the aorta, so that there is no axial or angular displacement in the inflow or outflow. FIGS. 22A-22C illustrate an example of a collinear MCS 120. FIG. 22A schematically illustrate a cross section of an example of a collinear MCS 120, including an impeller 126 and diffuser 128. FIGS. 22B and 22C illustrate perspective views of an example of a collinear MCS 120. The inlet 122 of the MCS 120 may be grafted directly in-line with the upper portion of the descending aorta. In some variations, the inlet 122 may include pre-swirl stationary vanes (not shown) above the impeller 126, described elsewhere herein. Blood may be pushed by the impeller 126 in a radially outward direction into the diffuser 128. The diffuser 128 may reorient the outflow from a radial direction, aligned 90 degrees relative to the inflow, to an axial direction, aligned collinear with the inflow and with the lower portion of the descending aorta. The diffuser scroll 129 may wrap-around the casing of the MCS 120. The diffuser scroll 129 may extend inward toward the longitudinal axis of the MCS 120 once it extends below the bottom of the MCS 120 casing.

The diffuser scroll 129 may extend in a spiral/helical fashion. In some implementations, the diffuser scroll 129 may progressively turn toward the axial direction as it wraps around the casing. The diffuser scroll 129 may gradually shift flow from a circumferential to an axial direction or may turn to the axial direction primarily near the outlet 124. The wrap-around diffuser 128 sends flow vertically downward and may terminate in a funnel-like shape at the outlet 124 with an expanding diameter. The diameter of the diffuser scroll 129 may increase as it extends from the impeller 126 toward the outlet 124. As seen in the cross-section of FIG. 22A, the cross-section of the diffuser scroll 129 may be smaller on one side of the MCS 120 (e.g., the right side of the figure) than the other side (e.g., the left side of the figure). Blood may travel through the diffuser scroll 129 along the direction of the diffuser's increasing size. The helical direction of blood flow through the diffuser 128 is schematically illustrated by the continuous arrow in FIG. 22A. The increasing diameter of the diffuser 128 may promote vortex formation in the outflow.

The diffuser 128 may perform only a partial revolution around the axis of the MCS 120, a single revolution, multiple revolutions, or any degree of revolutions there between. For example, the diffuser 128 may make a half turn, a three-quarter turn, a whole turn, one and a half turns, two turns, two and a half turns, three turns, etc., before terminating at the outlet 124. The azimuthal turning in the scroll 129 from point 321 of the diffuser 320 to the end of the turning in the scroll 129 could be any angle or could be at a varying angle. The diffuser 128 may make a sharp bend in the axial direction just before reaching the outlet 124. The wrap-around design may be useful for inducing vortex formation in the outflow of the MCS 120. The design parameters of the diffuser 128 may be altered to optimize helix formation. These may include the diameter of the diffuser 128, the change in the diameter of the diffuser 128, the number of revolutions made by the diffuser 128, the pitch of the turns, and the sharpness in the bend toward the axial direction, particularly toward the outlet. The configuration of the collinear MCS 120 may be relatively compact. The wrap-around diffuser 128 may minimize the overall diameter of the MCS 120. The collinear configuration may reduce the length of inlet and/or outlet grafts 106, 108, thus reducing the overall axial length of the MCS 120. The generally small size of the collinear MCS 120 may make it particularly conducive for installation via minimally invasive surgery.

The MCS 100 (and other MCSs disclosed herein) may employ stationary vanes to further alter the inflow and/or outflow of blood through the device. In some embodiments, the MCS 100 may include stationary pre-swirl vanes 323 (also known as inlet guide vanes). FIG. 23A schematically depicts a side view of an inlet 102 comprising stationary pre-swirl vanes 323. FIG. 23B schematically depicts an opened/flattened circumferential portion of inlet 102 comprising stationary pre-swirl vanes 323. One or more of these vanes 323 may extend from the inner circumference of the inlet 102 into the axial flow path of the introduced blood. The vanes 323 may be substantially flat. In other embodiments, the vanes 323 may have a curved surface. The vanes 323 may curve the blood flow in the direction of impeller rotation. In some implementations, the curves may curve the flow in the direction of the native aortic passage vortex. As shown in FIG. 23A, the vanes 323 may decrease in width as they extend from the inner diameter of the inlet 102 toward the longitudinal axis of the inlet 102. In some embodiments, the vanes may extend to the longitudinal axis. The decreasing width may allow the accommodation of adjacent vanes 323 around the circumference of the inlet 102. As shown in FIG. 23B, the vanes 323 may be angled with respect to the circumference of the inlet such that they extend partially in a circumferential direction and partially in an axial direction. The vanes 323 may all be identical in shape or they may vary in shape. The vanes 323 may all extend at the same angle relative the circumference and longitudinal axis or they may extend at different angles. In some implementations, as shown in FIG. 23A, the vanes 323 may be configured such they cumulatively occupy the entire cross section of the inlet 102, but because they are angled blood may flow between the vanes 323. In some embodiments, the vanes 323 may partially overlap each other in the axial direction. In some embodiments, the vanes 323 do not occupy the entire cross section of the inlet 102, such that blood could potentially flow in a purely axial direction between the vanes 323. The vanes 323 may pre-swirl the blood entering the MCS 100 prior to reaching the impeller 200. The vanes 323 may improve fluid dynamics of blood flow through the MCS 100 (add a rotational velocity to the blood flow) at the cost of increased friction with the blood. The improved fluid dynamics may be used to adjust the flow rate and/or improve the efficiency of the turbomachine. For example, the vanes 323 may allow increased rotational speed with reduced motor power. In some embodiments, there may be multiple rows of pre-swirl vanes 323 along the axial direction. In some embodiments, the vanes 323 may not all be positioned at the same axial position but may be axially spaced from each other (e.g., in a helical formation). In some embodiments including pre-swirl vanes 323, pre-swirl vanes 323 may be directly incorporated into the upper channel 203 of the impeller in addition to or alternatively to the inlet 102. In some embodiments, the vanes 323 may be incorporated into the outlet 104 in addition to or alternatively to the inlet 102.

In some embodiments, the MCS 100 may include a vaned diffuser 320 (and/or a vaned volute extending at the terminal end of the diffuser 320). The vaned diffuser 320 may be used to optimize fluid dynamics, such as vortex formation, in the outflow of the device. FIG. 23C schematically illustrates an example of a top cross-section of a casing 300 comprising a diffuser 320 with a single splitter vane 324 which creates a split double volute at the outlet 104, comprising two parallel fluid passages. One or more splitter vanes 324 may be used to even out flow distribution, particularly between the inner side of the volute (left side of FIG. 23C) and the outer side of the volute (right side of FIG. 23C). FIG. 23D, schematically illustrates a variation of the split diffuser shown in FIG. 23C, in which the diffuser vane 324 only extends partially or not at all into the circumferential diffuser 320 passage (the portion of the passage prior to the straight volute passage). In some embodiments, the splitter vane(s) 324 is not a wall aligned purely with the axial direction of the device. The splitter vane(s) 324 may rotate relative to the cross-sectional circumference of the passage as it extends along the diffuser and/or volute. The use of a rotating splitter vane(s) 324 may add rotational velocity to the blood outflow and may be used to help emulate the naturally occurring vortex formation in the healthy aorta. FIG. 23E schematically illustrates an example of a casing 300 with a vaned diffuser comprising a plurality of diffuser vanes 325 surrounding the inner circumference of the diffuser 320. The diffuser vanes 325 may be slightly curved in a direction configured to orient the blood toward the outlet 104. The diffuser vanes may be uniformly spaced around the circumference of the diffuser 320. In some embodiments, not all portions of the circumference of the diffuser 320 may incorporate diffuser vanes. The diffuser vanes 325 may be used to improve distribution of fluid flow within the diffuser 320. Similar to the stationary pre-swirl vanes 323, the vanes within the diffuser and/or volute may impart additional friction to the blood.

The embodiments disclosed herein may be designed with considerations from the following references in mind, each of which is hereby incorporated by reference in its entirety. Considerations for geometric optimization of centrifugal impellers related to MCSD specifications of pressure rise, flow rate, diameter and rotational speed are described by: Korakianitis, T., Rezaienia, M. A., Paul, G. M., Rahideh, A., Rothman, M. T., Mozafari, S., "Optimization of Centrifugal Pump Characteristic Dimensions for Mechanical Circulatory Support Devices" (2016) ASAIO Journal, 62 (5), pp. 545-551; and Mozafari, S., Rezaienia, M. A., Paul, G. M., Rothman, M. T., Wen, P., Korakianitis, T., "The Effect of Geometry on the Efficiency and Hemolysis of Centrifugal Implantable Blood Pumps" (2017) ASAIO Journal, 63 (1), pp. 53-59.

The machinability of centrifugal impellers is described by: Paul, G., Rezaienia, A., Avital, E., Korakianitis, T., "Machinability and optimization of shrouded centrifugal impellers for implantable blood pumps" (2017) Journal of Medical Devices, Transactions of the ASME, 11 (2), art. no. 021005. The effects of a patient's motion on device operation are described by: Paul, G., Rezaienia, A., Shen, X., Avital, E., Korakianitis, T., "Slip and turbulence phenomena in journal bearings with application to implantable rotary blood pumps" (2016) Tribology International, 104, pp. 157-165; and Paul, G., Rezaienia, M. A., Rahideh, A., Munjiza, A., Korakianitis, T., "The Effects of Ambulatory Accelerations on the Stability of a Magnetically Suspended Impeller for an Implantable Blood Pump" (2016) Artificial Organs, 40 (9), pp. 867-876.

The effects of device implantation in the descending aorta are described by Rezaienia, M. A., Paul, G., Avital, E. J., Mozafari, S., Rothman, M., Korakianitis, T. "In-vitro investigation of the hemodynamic responses of the cerebral, coronary and renal circulations with a rotary blood pump installed in the descending aorta" (2017) Medical Engineering and Physics, 40, pp. 2-10; Rezaienia, M. A., Paul, G., Avital, E., Rahideh, A., Rothman, M. T., Korakianitis, T., "In-vitro investigation of cerebral-perfusion effects of a rotary blood pump installed in the descending aorta" (2016) Journal of Biomechanics, 49 (9), pp. 1865-1872; Rezaienia, M. A., Rahideh, A., Alhosseini Hamedani, B., Bosak, D. E. M., Zustiak, S., Korakianitis, T., "Numerical and In Vitro Investigation of a Novel Mechanical Circulatory Support Device Installed in the Descending Aorta" (2015) Artificial Organs, 39 (6), pp. 502-513; and Rezaienia, M. A., Rahideh, A., Rothman, M. T., Sell, S. A., Mitchell, K., Korakianitis, T., "In vitro comparison of two different mechanical circulatory support devices installed in series and in parallel" (2014) Artificial Organs, 38 (9), pp. 800-809.

Considerations for MCSD electric motor design are described by: Rahideh, A., Mardaneh, M., Korakianitis, T., "Analytical 2-D calculations of torque, inductance, and back-EMF for brushless slotless machines with surface inset magnets" (2013) IEEE Transactions on Magnetics, 49 (8), art. no. 6418033, pp. 4873-4884; Rahideh, A., Korakianitis, T., "Analytical calculation of open-circuit magnetic field distribution of slotless brushless PM machines" (2013) International Journal of Electrical Power and Energy Systems, 44 (1), pp. 99-114; Rahideh, A., Korakianitis, T., "Analytical magnetic field distribution of slotless brushless PM motors. Part 2: Open-circuit field and torque calculations" (2012) IET Electric Power Applications, 6 (9), pp. 639-651; Rahideh, A., Korakianitis, T., "Analytical magnetic field distribution of slotless brushless permanent magnet motors—Part I. Armature reaction field, inductance and rotor eddy current loss calculations" (2012) IET Electric Power Applications, 6 (9), pp. 628-638; Rahideh, A., Korakianitis, T., "Analytical magnetic field calculation of slotted brushless permanent-magnet machines with surface inset magnets" (2012) IEEE Transactions on Magnetics, 48 (10), art. no. 6203591, pp. 2633-2649; Rahideh, A., Korakianitis, T., "Subdomain Analytical Magnetic Field Prediction of Slotted Brushless Machines with Surface Mounted Magnets" (2012) International Review of Electrical Engineering, 7 (2), pp. 3891-3909; Rahideh, A., Korakianitis, T., "Analytical armature reaction field distribution of slotless brushless machines with inset permanent magnets" (2012) IEEE Transactions on Magnetics, 48 (7), art. no. 6126045, pp. 2178-2191; Rahideh, A., Korakianitis, T., "Brushless DC motor design using harmony search optimization" (2012) Proceedings—2011 2nd International Conference on Control, Instrumentation and Automation, ICCIA 2011, art. no. 6356628, pp. 44-50; Rahideh, A., Korakianitis, T., "Analytical open-circuit magnetic field distribution of slotless brushless permanent-magnet machines with rotor eccentricity" (2011) IEEE Transactions on Magnetics, 47 (12), art. no. 5893946, pp. 4791-4808; Rahideh, A., Korakianitis, T., "Analytical magnetic field distribution of slotless brushless machines with inset permanent magnets" (2011) IEEE Transactions on Magnetics, 47 (6 PART 2), art. no. 5706366, pp. 1763-1774; and Rahideh, A., Korakianitis, T., Ruiz, P., Keeble, T., Rothman, M. T., "Optimal brushless DC motor design using genetic algorithms" (2010) Journal of Magnetism and Magnetic Materials, 322 (22), pp. 3680-3687.

Numerical simulations of the cardiovascular system with implanted MCSDs are described by: Shi, Y., Korakianitis, T., Bowles, C., "Numerical simulation of cardiovascular dynamics with different types of VAD assistance" (2007) Journal of Biomechanics, 40 (13), pp. 2919-2933; Korakianitis, T., Shi, Y., "Numerical comparison of hemodynamics with atrium to aorta and ventricular apex to aorta VAD support" (2007) ASAIO Journal, 53 (5), pp. 537-548; Shi, Y., Korakianitis, T., "Numerical simulation of cardiovascular dynamics with left heart failure and in-series pulsatile ventricular assist device" (2006) Artificial Organs, 30 (12), pp. 929-948; Korakianitis, T., Shi, Y., "Effects of atrial contraction, atrioventricular interaction and heart valve dynamics on human cardiovascular system response" (2006) Medical Engineering and Physics, 28 (8), pp. 762-779; Korakianitis, T., Shi, Y., "A concentrated parameter model for the human cardiovascular system including heart valve dynamics and atrioventricular interaction" (2006) Medical Engineering and Physics, 28 (7), pp. 613-628; and Korakianitis, T., Shi, Y., "Numerical simulation of cardiovascular dynamics with healthy and diseased heart valves" (2006) Journal of Biomechanics, 39 (11), pp. 1964-1982.

Devices for emulating the human cardiovascular system for in-vitro testing of VADs and MCSD are described by: Ruiz, P., Rezaienia, M. A., Rahideh, A., Keeble, T. R., Rothman, M. T., Korakianitis, T., "In vitro cardiovascular system emulator (Bioreactor) for the simulation of normal and diseased conditions with and without mechanical circulatory support" (2013) Artificial Organs, 37 (6), pp. 549-560.

Although the present invention has been described in terms of certain preferred embodiments, it may be incorporated into other embodiments by persons of skill in the art in view of the disclosure herein. The scope of the invention is therefore not intended to be limited by the specific embodiments disclosed herein, but is intended to be defined by the full scope of the following claims.

What is claimed is:

1. A method of treating cardiovascular function in a patient, the patient having a native aorta comprising an ascending aorta, an aortic arch, and a descending aorta, the method comprising:
installing a mechanical circulation support within the descending aorta of the patient, wherein the mechanical circulation support comprises an impeller positioned within an internal volume of a mechanical body of the mechanical circulation support, wherein the impeller comprises a plurality of blades for pumping blood, the blades being arranged around a longitudinal axis and defining an outer circumference, wherein the mechanical circulation support is configured to provide a pressure rise between 20 mmHg and 50 mmHg in blood flow, wherein an inlet of the mechanical circulation support is in the descending aorta and an outlet of the mechanical circulation support is further downstream in the descending aorta, and the blood flow is continuously from upstream to downstream inside the mechanical circulatory support, wherein the mechanical circulation support is configured to maintain a continuous flow rate.

2. The method of claim 1, wherein the mechanical circulation support is configured to maintain a flow rate of 5 L/min.

3. The method of claim 1, wherein the mechanical circulation support does not mimic the pulsatile flow imparted by the native heart.

4. The method of claim 1, wherein the mechanical circulation support is configured to create a vortex in an outflow of blood exiting the outlet to emulate a naturally-occurring vortex in the native aorta of a healthy human heart.

5. The method of claim 1, wherein the mechanical circulation support is configured to be installed in series with a portion of the descending aorta.

6. The method of claim 1, wherein the mechanical circulation support is configured for assisting native heart function in cases of congestive heart failure.

7. The method of claim 1, wherein the inlet of the mechanical circulation support comprises a vane altering an inflow of blood through the mechanical circulation support.

8. The method of claim 1, wherein the inlet of the mechanical circulation support comprises a vane altering an outflow of blood through the mechanical circulation support.

9. A method of treating cardiovascular function in a patient, the patient having a native aorta comprising an ascending aorta, an aortic arch, and a descending aorta, the method comprising:
installing a mechanical circulation support within the descending aorta of the patient, wherein the mechanical circulation support comprises an impeller positioned within an internal volume of a mechanical body of the mechanical circulation support, wherein the impeller comprises a plurality of blades for pumping blood, the blades being arranged around a longitudinal axis and defining an outer circumference, wherein the mechanical circulation support is configured to provide a pressure rise between 40 mmHg and 80 mmHg in blood flow, wherein an inlet of the mechanical circulation support is in the descending aorta and an outlet of the mechanical circulation support is further downstream in the descending aorta, and the blood flow is continuously from upstream to downstream inside the mechanical circulatory support, wherein the mechanical circulation support is configured to replicate a naturally occurring vortex formation within the aorta.

10. The method of claim 9, wherein the mechanical circulation support is configured to maintain a flow rate equivalent to the normal cardiac output.

11. The method of claim 9, wherein the mechanical circulation support is configured to provide continuous flow.

12. The method of claim 9, wherein the mechanical circulation support is configured to provide pulsatile flow.

13. The method of claim 9, wherein the mechanical circulation support is installed in series with the descending aorta.

14. The method of claim 9, wherein the mechanical circulation support is configured for replacing native heart function in cases of congestive heart failure.

15. A method of treating cardiovascular function in a patient, the patient having a native aorta comprising an ascending aorta, an aortic arch, and a descending aorta, the method comprising:
installing a mechanical circulation support within the descending aorta of the patient, wherein the mechanical circulation support comprises an impeller positioned within an internal volume of a mechanical body of the mechanical circulation support, wherein the impeller comprises a plurality of blades for pumping blood, the blades being arranged around a longitudinal axis and defining an outer circumference, wherein the mechanical circulation support is configured to provide a pressure rise between 20 mmHg and 80 mmHg in blood flow, wherein an inlet of the mechanical circulation support is in the descending aorta and an outlet of the mechanical circulation support is further downstream in the descending aorta, and the blood flow is continuously from upstream to downstream inside the mechanical circulatory support, wherein the mechanical circulation support is installed with the inlet and the outlet oriented collinear with the native aorta.

16. The method of claim 15, wherein the mechanical circulation support is configured to maintain a continuous flow rate of 5 L/min.

17. The method of claim 15, wherein the mechanical circulation support is configured to replicate a naturally occurring vortex.

* * * * *